United States Patent
Ruchti et al.

(10) Patent No.: US 9,375,170 B2
(45) Date of Patent: Jun. 28, 2016

(54) MULTIPLEXED PATHLENGTH RESOLVED NONINVASIVE ANALYZER APPARATUS WITH STACKED FILTERS AND METHOD OF USE THEREOF

(71) Applicants: Timothy Ruchti, Gurnee, IL (US); Alan Abul-Haj, Mesa, AZ (US); Kevin Hazen, Gilbert, AZ (US)

(72) Inventors: Timothy Ruchti, Gurnee, IL (US); Alan Abul-Haj, Mesa, AZ (US); Kevin Hazen, Gilbert, AZ (US)

( * ) Notice: Subject to any disclaimer, the term of this patent is extended or adjusted under 35 U.S.C. 154(b) by 0 days.

(21) Appl. No.: 14/938,688

(22) Filed: Nov. 11, 2015

(65) Prior Publication Data

US 2016/0058340 A1 Mar. 3, 2016

Related U.S. Application Data

(63) Continuation of application No. 14/493,266, filed on Sep. 22, 2014, which is a continuation-in-part of application No. 13/963,925, filed on Aug. 9, 2013, which is a continuation-in-part of application No. 13/941,411, filed on Jul. 12, 2013, which is a continuation-in-part of application No. 13/941,389, filed on Jul. 12, 2013, which is a continuation-in-part of application No. 13/941,369, filed on Jul. 12, 2013.

(60) Provisional application No. 61/672,195, filed on Jul. 16, 2012, provisional application No. 61/700,291, filed on Sep. 12, 2012, provisional application No. 61/700,294, filed on Sep. 12, 2012.

(51) Int. Cl.
| | |
|---|---|
| *G01N 5/02* | (2006.01) |
| *A61B 5/1455* | (2006.01) |
| *A61B 5/145* | (2006.01) |
| *A61B 5/00* | (2006.01) |

(52) U.S. Cl.
CPC ............ *A61B 5/1455* (2013.01); *A61B 5/14532* (2013.01); *A61B 5/6801* (2013.01); *A61B 2562/04* (2013.01); *A61B 2562/046* (2013.01)

(58) Field of Classification Search
CPC ............... A61B 5/1455; A61B 5/6801; A61B 5/14532; A61B 2562/046
USPC ..................................................... 250/339.02
See application file for complete search history.

(56) References Cited

U.S. PATENT DOCUMENTS

| | | |
|---|---|---|
| 5,057,695 A | 10/1991 | Hirao |
| 5,086,229 A | 2/1992 | Rosenthal |
| 5,229,841 A | 7/1993 | Taranowski et al. |
| 5,237,178 A | 8/1993 | Rosenthal |
| 5,324,979 A | 6/1994 | Rosenthal |
| 5,459,317 A | 10/1995 | Small et al. |
| 5,636,633 A | 6/1997 | Messerschmidt et al. |
| 5,655,530 A | 8/1997 | Messerschmidt |
| 5,747,806 A | 5/1998 | Khalil et al. |
| 5,750,994 A | 5/1998 | Schlager |
| 5,823,951 A | 10/1998 | Messerschmidt |

(Continued)

*Primary Examiner* — David Porta
*Assistant Examiner* — Gisselle Gutierrez
(74) *Attorney, Agent, or Firm* — Kevin Hazen

(57) ABSTRACT

A noninvasive analyzer apparatus and method of use thereof is described using a plurality of sample illumination zones optically coupled to at least two optically stacked two-dimensional optical filter arrays. Sectioned pixels and/or zones of a detector array are optionally filtered for different light throughput and/or are passed through various pathlengths using the stacked two-dimensional optical filter arrays. Resulting pathlength resolved/wavelength controlled groups of spectra are subsequently analyzed to determine an analyte property.

15 Claims, 25 Drawing Sheets

(56) References Cited

U.S. PATENT DOCUMENTS

| | | |
|---|---|---|
| 5,945,676 A | 8/1999 | Khalil et al. |
| 5,957,841 A | 9/1999 | Maruo et al. |
| 6,040,578 A | 3/2000 | Malin et al. |
| 6,061,582 A | 5/2000 | Small et al. |
| 6,115,673 A | 9/2000 | Malin et al. |
| 6,152,876 A | 11/2000 | Robinson et al. |
| 6,188,705 B1 | 2/2001 | Krainak |
| 6,236,047 B1 | 5/2001 | Malin et al. |
| 6,240,306 B1 | 5/2001 | Rohrscheib et al. |
| 6,280,381 B1 | 8/2001 | Malin et al. |
| 6,353,226 B1 | 3/2002 | Khalil et al. |
| 6,405,065 B1 | 6/2002 | Malin et al. |
| 6,411,373 B1 | 6/2002 | Garside et al. |
| 6,415,167 B1 | 7/2002 | Blank et al. |
| 6,442,408 B1 | 8/2002 | Wenzel et al. |
| 6,456,870 B1 | 9/2002 | Rennert et al. |
| 6,475,800 B1 | 11/2002 | Hazen et al. |
| 6,487,429 B2 | 11/2002 | Hockersmith et al. |
| 6,493,566 B1 | 12/2002 | Ruchti et al. |
| 6,501,982 B1 | 12/2002 | Ruchti et al. |
| 6,512,936 B1 | 1/2003 | Monfre et al. |
| 6,512,937 B2 | 1/2003 | Blank et al. |
| 6,534,012 B1 | 3/2003 | Hazen et al. |
| 6,571,117 B1 | 5/2003 | Marbach |
| 6,574,490 B2 | 6/2003 | Abbink et al. |
| 6,587,196 B1 | 7/2003 | Stippick et al. |
| 6,587,199 B1 | 7/2003 | Luu |
| 6,587,702 B1 | 7/2003 | Ruchti et al. |
| 6,594,513 B1 | 7/2003 | Jobsis et al. |
| 6,640,117 B2 | 10/2003 | Makarewicz et al. |
| 6,668,181 B2 | 12/2003 | Wenzel et al. |
| 6,671,542 B2 | 12/2003 | Rennert et al. |
| 6,675,029 B2 | 1/2004 | Monfre et al. |
| 6,697,654 B2 | 2/2004 | Lorenz et al. |
| 6,704,662 B2 | 3/2004 | Gulati |
| 6,718,189 B2 | 4/2004 | Rohrscheib et al. |
| 6,728,560 B2 | 4/2004 | Kollias |
| 6,738,652 B2 | 5/2004 | Mattu et al. |
| 6,777,240 B2 | 8/2004 | Hazen et al. |
| 6,788,965 B2 | 9/2004 | Ruchti et al. |
| 6,816,241 B2 | 11/2004 | Grubisic |
| 6,839,584 B2 | 1/2005 | Makarewicz et al. |
| 6,864,978 B1 | 3/2005 | Hazen et al. |
| 6,871,169 B1 | 3/2005 | Hazen et al. |
| 6,876,931 B2 | 4/2005 | Lorenz et al. |
| 6,956,649 B2 | 10/2005 | Acosta et al. |
| 6,990,364 B2 | 1/2006 | Ruchti et al. |
| 6,998,247 B2 | 2/2006 | Monfre et al. |
| 7,009,180 B2 | 3/2006 | Sterling |
| 7,010,336 B2 | 3/2006 | Lorenz et al. |
| 7,015,782 B2 | 3/2006 | Kincaid et al. |
| 7,038,774 B2 | 5/2006 | Hazen et al. |
| 7,039,446 B2 | 5/2006 | Ruchti et al. |
| D526,719 S | 8/2006 | Richie, Jr. et al. |
| D529,616 S | 10/2006 | Deros et al. |
| 7,133,710 B2 | 11/2006 | Acosta et al. |
| 7,147,153 B2 | 12/2006 | Rowe et al. |
| 7,183,102 B2 | 2/2007 | Monfre et al. |
| 7,206,623 B2 | 4/2007 | Blank et al. |
| 7,233,816 B2 | 6/2007 | Blank et al. |
| 7,299,080 B2 | 11/2007 | Acosta et al. |
| 7,317,938 B2 | 1/2008 | Lorenz et al. |
| 7,333,843 B2 | 2/2008 | Monfre et al. |
| 7,356,364 B1 | 4/2008 | Bullock et al. |
| 7,383,069 B2 | 6/2008 | Ruchti et al. |
| 7,395,158 B2 | 7/2008 | Monfre et al. |
| 7,436,511 B2 | 10/2008 | Ruchti et al. |
| 7,440,786 B2 | 10/2008 | Hockersmith et al. |
| 7,488,930 B2 | 2/2009 | Ajgaonkar |
| 7,505,801 B2 | 3/2009 | Monfre et al. |
| 7,508,524 B2 | 3/2009 | Mahadevan-Jansen et al. |
| 7,509,153 B2 | 3/2009 | Blank et al. |
| 7,519,406 B2 | 4/2009 | Blank et al. |
| 7,567,876 B2 | 7/2009 | Gulati |
| 7,571,056 B2 | 8/2009 | Ben-Menahem et al. |
| 7,593,230 B2 | 9/2009 | Abul-Haj et al. |
| 7,606,608 B2 | 10/2009 | Blank et al. |
| 7,620,212 B1 | 11/2009 | Allen et al. |
| 7,620,674 B2 | 11/2009 | Ruchti et al. |
| 7,640,140 B2 | 12/2009 | Ruchti et al. |
| 7,697,966 B2 | 4/2010 | Monfre et al. |
| 7,698,105 B2 | 4/2010 | Ruchti et al. |
| RE41,333 E | 5/2010 | Blank et al. |
| 7,738,085 B2 | 6/2010 | Braig |
| 7,751,192 B2 | 7/2010 | Abul-Haj et al. |
| 7,787,924 B2 | 8/2010 | Acosta et al. |
| 7,872,734 B2 | 1/2011 | Braig |
| 8,082,015 B2 | 12/2011 | Yodh et al. |
| 8,160,666 B2 | 4/2012 | Rebec |
| 8,170,326 B2 | 5/2012 | Gulati et al. |
| 8,315,681 B2 | 11/2012 | Kanayama et al. |
| 8,380,268 B2 | 2/2013 | Georgakoudi |
| 2002/0041166 A1 | 4/2002 | Grubisic |
| 2002/0042558 A1 | 4/2002 | Mendelson |
| 2002/0084417 A1 | 7/2002 | Khalil |
| 2003/0060693 A1 | 3/2003 | Monfre |
| 2003/0078504 A1 | 4/2003 | Rowe |
| 2003/0208113 A1 | 11/2003 | Mault |
| 2004/0162470 A1 | 8/2004 | Tu |
| 2005/0010090 A1 | 1/2005 | Acosta et al. |
| 2005/0054908 A1 | 3/2005 | Blank et al. |
| 2005/0124869 A1 | 6/2005 | Hefti et al. |
| 2005/0261560 A1 | 11/2005 | Ridder |
| 2005/0267342 A1 | 12/2005 | Blank |
| 2006/0116562 A1 | 6/2006 | Acosta et al. |
| 2006/0157640 A1* | 7/2006 | Perlman .............. H04N 5/2254 250/208.1 |
| 2006/0173254 A1 | 8/2006 | Acosta et al. |
| 2006/0173255 A1 | 8/2006 | Acosta et al. |
| 2006/0183983 A1 | 8/2006 | Acosta et al. |
| 2006/0195023 A1 | 8/2006 | Acosta et al. |
| 2006/0200017 A1* | 9/2006 | Monfre ................ A61B 5/061 600/344 |
| 2006/0206018 A1 | 9/2006 | Abul-Haj |
| 2006/0211927 A1 | 9/2006 | Acosta et al. |
| 2006/0234386 A1 | 10/2006 | Burns |
| 2007/0149868 A1 | 6/2007 | Blank et al. |
| 2007/0255141 A1 | 11/2007 | Esenaliev |
| 2007/0278389 A1 | 12/2007 | Ajgaonkar |
| 2008/0221410 A1 | 9/2008 | Campbell |
| 2008/0232653 A1 | 9/2008 | Rowe |
| 2008/0291394 A1 | 11/2008 | Ishak |
| 2008/0319286 A1 | 12/2008 | Ridder |
| 2009/0003764 A1 | 1/2009 | Ridder |
| 2009/0098587 A1 | 4/2009 | Hetzel et al. |
| 2009/0185191 A1 | 7/2009 | Boppart |
| 2009/0225277 A1* | 9/2009 | Gil ..................... A61B 5/1455 351/206 |
| 2009/0247840 A1 | 10/2009 | Blank et al. |
| 2010/0010325 A1 | 1/2010 | Ridder |
| 2010/0016689 A1 | 1/2010 | Kanayama et al. |
| 2010/0113899 A1 | 5/2010 | Robinson et al. |
| 2010/0160747 A1 | 6/2010 | Robinson et al. |
| 2011/0184260 A1 | 7/2011 | Robinson |
| 2012/0059232 A1 | 3/2012 | Gross |
| 2012/0129269 A1 | 5/2012 | Choi |
| 2012/0130215 A1 | 5/2012 | Fine |
| 2015/0011849 A1 | 1/2015 | Ruchti |
| 2015/0011850 A1 | 1/2015 | Ruchti |
| 2015/0015888 A1 | 1/2015 | Gulati |
| 2015/0018642 A1 | 1/2015 | Gulati |
| 2015/0018644 A1 | 1/2015 | Gulati |
| 2015/0018646 A1 | 1/2015 | Gulati |
| 2015/0041656 A1 | 2/2015 | Novotny |
| 2015/0045636 A1 | 2/2015 | Novotny |

* cited by examiner

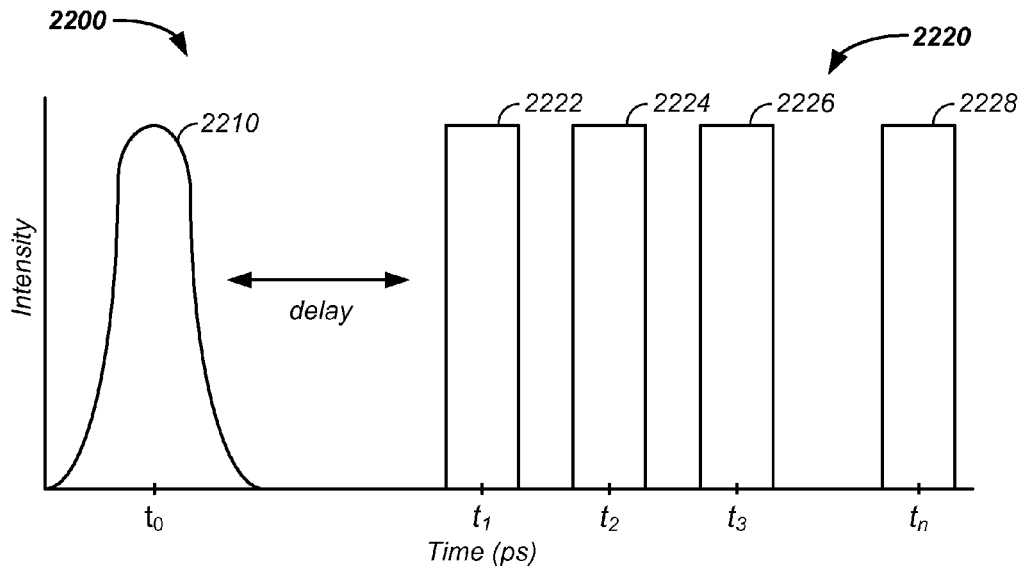
FIG. 22A
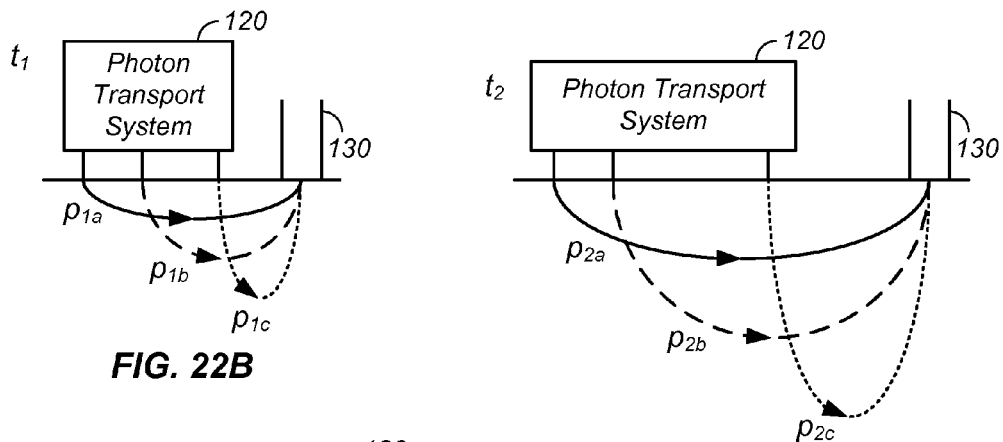
FIG. 22B
FIG. 22C
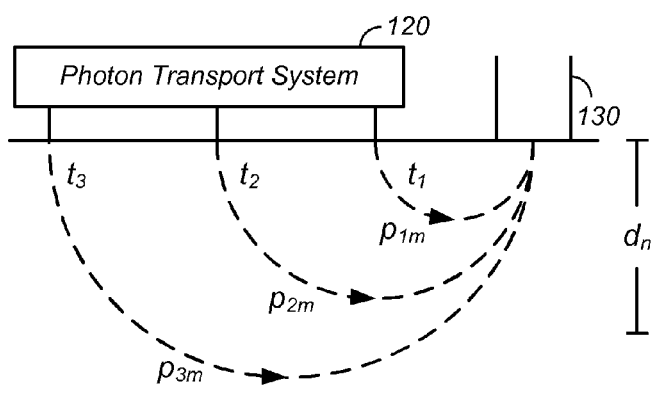
FIG. 22D

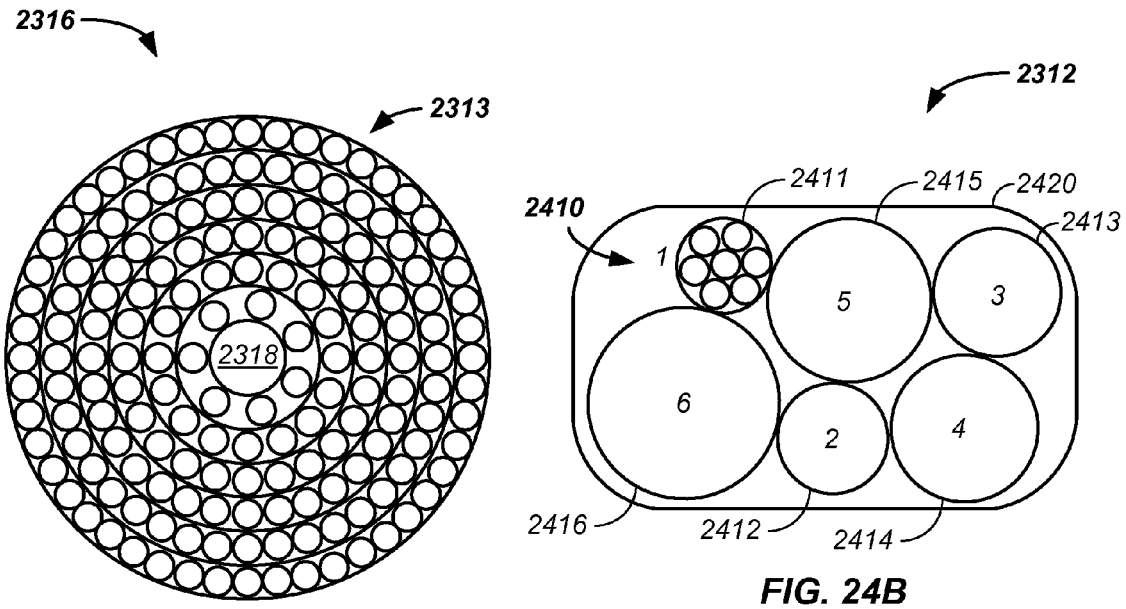
FIG. 24A
FIG. 24B
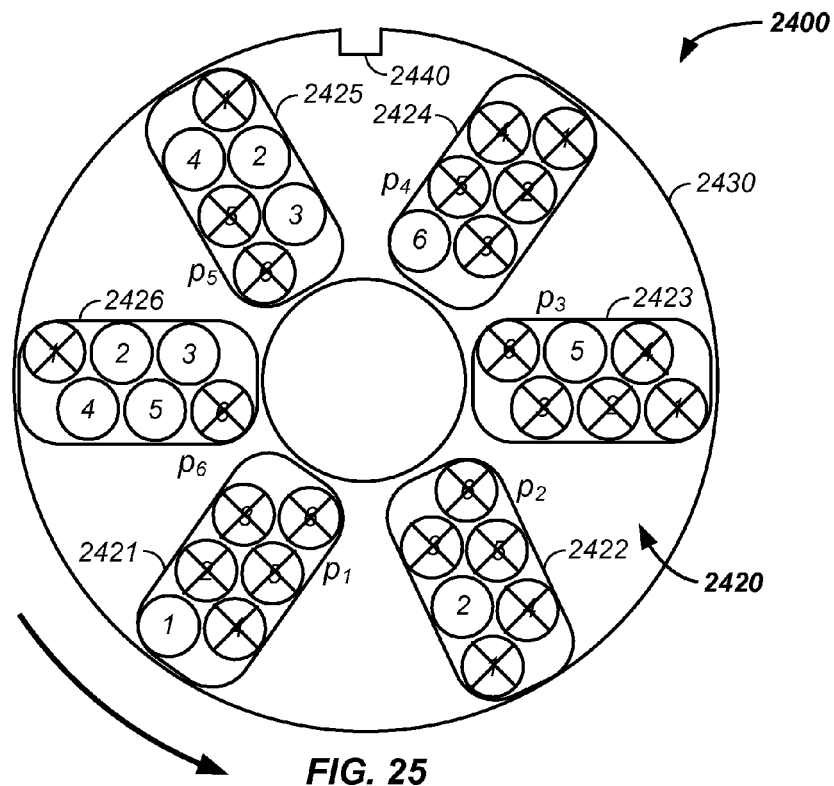
FIG. 25

MULTIPLEXED PATHLENGTH RESOLVED NONINVASIVE ANALYZER APPARATUS WITH STACKED FILTERS AND METHOD OF USE THEREOF

CROSS REFERENCES TO RELATED APPLICATIONS

This application is a continuation of U.S. patent application Ser. No. 14/493,266 filed Sep. 22, 2014, which is a continuation-in-part of U.S. patent application Ser. No. 13/963,925 filed Aug. 9, 2013, which is a continuation-in-part of U.S. patent application Ser. No. 13/941,411 filed Jul. 12, 2013, which is a continuation-in-part of U.S. patent application Ser. No. 13/941,389 filed Jul. 12, 2013, which is a continuation-in-part of U.S. patent application Ser. No. 13/941,369 filed Jul. 12, 2013, which claims the benefit of:
 U.S. provisional patent application No. 61/672,195 filed Jul. 16, 2012;
 U.S. provisional patent application No. 61/700,291 filed Sep. 12, 2012; and
 U.S. provisional patent application No. 61/700,294 filed Sep. 12, 2012,
 all of which are incorporated herein in their entirety by this reference thereto.

TECHNICAL FIELD OF THE INVENTION

The present invention relates to a near-infrared noninvasive analyzer using a two-dimensional detector array.

DESCRIPTION OF THE RELATED ART

Patents and literature related to the current invention are summarized herein.
Diabetes Diabetes mellitus or diabetes is a chronic disease resulting in the improper production and/or use of insulin, a hormone that facilitates glucose uptake into cells. Diabetes is broadly categorized into four forms grouped by glucose concentration state: hyperinsulinemia (hypoglycemia), normal physiology, impaired glucose tolerance, and hypoinsulinemia (hyperglycemia).

Diabetics have increased risk in three broad categories: cardiovascular heart disease, retinopathy, and/or neuropathy. Complications of diabetes include: heart disease, stroke, high blood pressure, kidney disease, nerve disease and related amputations, retinopathy, diabetic ketoacidosis, skin conditions, gum disease, impotence, and/or fetal complications.

Diabetes is a common and increasingly prevalent disease. Currently, diabetes is a leading cause of death and disability worldwide. The World Health Organization estimates that the number of people with diabetes will grow to three hundred million by the year 2025.

Long term clinical studies show that the onset of diabetes related complications is significantly reduced through proper control of blood glucose concentrations. The Diabetes Control and Complications Trial Research Group, "The Effect of Intensive Treatment of Diabetes on the Development and Progression of Long-Term Complications in Insulin-Dependent Diabetes Mellitus", N. Eng. J. of Med., 1993, vol. 329, pp. 977-986.
Skin The structure of skin varies widely among individuals as well as between different skin sites on a single individual. The skin has layers, including: (1) a stratum corneum of flat, dehydrated, biologically inactive cell about 10 to 20 micrometers thick; (2) a stratified epidermis, of about 10 to 150 micrometers thickness, formed and continuously replenished by slow upward migration of keratinocyte cells from the germinative basal layer of the epidermis; (3) an underlying dermis of connective fibrous protein, such as collagen, and a blood supply, which form a layer of 0.5 to 4.0 millimeters in thickness with an average thickness of about 1.2 millimeters; and (4) a underlying fatty subcutaneous layer or adipose tissue.
Fiber Optic Sample Bundle Garside, J., et. al., "Fiber Optic Illumination and Detection Patterns, Shapes, and Locations for use in Spectroscopic Analysis", U.S. Pat. No. 6,411,373 (Jun. 25, 2002) describe software and algorithms to design fiber optic excitation and/or collection patterns in a sample probe.

Maruo, K., et. al., "Device for Non-Invasive Determination of Glucose Concentration in Blood", European patent application no. EP 0843986 B1 (Mar. 24, 2004) describe the use of light projecting fiber optics in the range of 0.1 to 2 millimeters from light receiving fiber optics at the contacted fiber optic bundle/sample interface.
Skin Thickness Rennert, J., et. al., "Non-Invasive Method of Determining Skin Thickness and Characterizing Layers of Skin Tissue In Vivo", U.S. Pat. No. 6,456,870 B1 (Sep. 24, 2002) describe the use of near-infrared absorbance spectra to determine overall thickness of skin tissue and layer-by-layer thickness of skin tissue.

Ruchti, T. L., et. al., "Classification System for Sex Determination and Tissue Characterization", U.S. Pat. No. 6,493,566 B1 (Dec. 10, 2002) describe the near-infrared tissue measurements to yield predictions consisting of gender and one or more of thickness of a dermis, collagen content, and amount of subcutaneous fat.

Mattu, M., et. al., "Classification and Screening of Test Subjects According to Optical Thickness of Skin", U.S. Pat. No. 6,738,652 B2 (May 18, 2004) describe the use of near-infrared reflectance measurements of skin to determine the optical thickness of skin through analysis of water, fat, and protein marker bands.
Sample Probe/Tissue Contact Abul-Haj, A., et. al., "Method and Apparatus for Noninvasive Targeting", U.S. patent application no. US 2006/0217602 A1 (Sep. 28, 2006) describe a sample probe interface method and apparatus for targeting a tissue depth and/or pathlength that is used in conjunction with a noninvasive analyzer to control spectral variation.

Welch, J. M., et. al., "Method and Apparatus for Noninvasive Probe/Skin Tissue Contact Sensing", WIPO international publication no. WO 2008/058014 A2 (May 15, 2008) describe a method and apparatus for determining proximity and/or contact of an optical probe with skin tissue.
Problem Statement What is needed is a noninvasive glucose concentration analyzer having precision and accuracy suitable for treatment of diabetes mellitus.

SUMMARY OF THE INVENTION

The invention comprises a noninvasive analyzer apparatus having at least two optical filter arrays yielding a range of wavelength groups transmitted to a detector array.

BRIEF DESCRIPTION OF THE DRAWINGS

A more complete understanding of the present invention is derived by referring to the detailed description and claims when considered in connection with the Figures, wherein like reference numbers refer to similar items throughout the Figures.

FIGS. 22(A-D) illustrate temporal resolution gating, FIG. 22A; probabilistic optical paths for a first elapsed time, FIG. 22B; probabilistic optical paths for a second elapsed time, FIG. 22C; and a temporal distribution method, FIG. 22D;

FIG. 24A illustrates a third example sample interface end of the fiber optic bundle and FIG. 24B illustrates a mask;

FIG. 25 illustrates a mask selection wheel;

Figure 1:
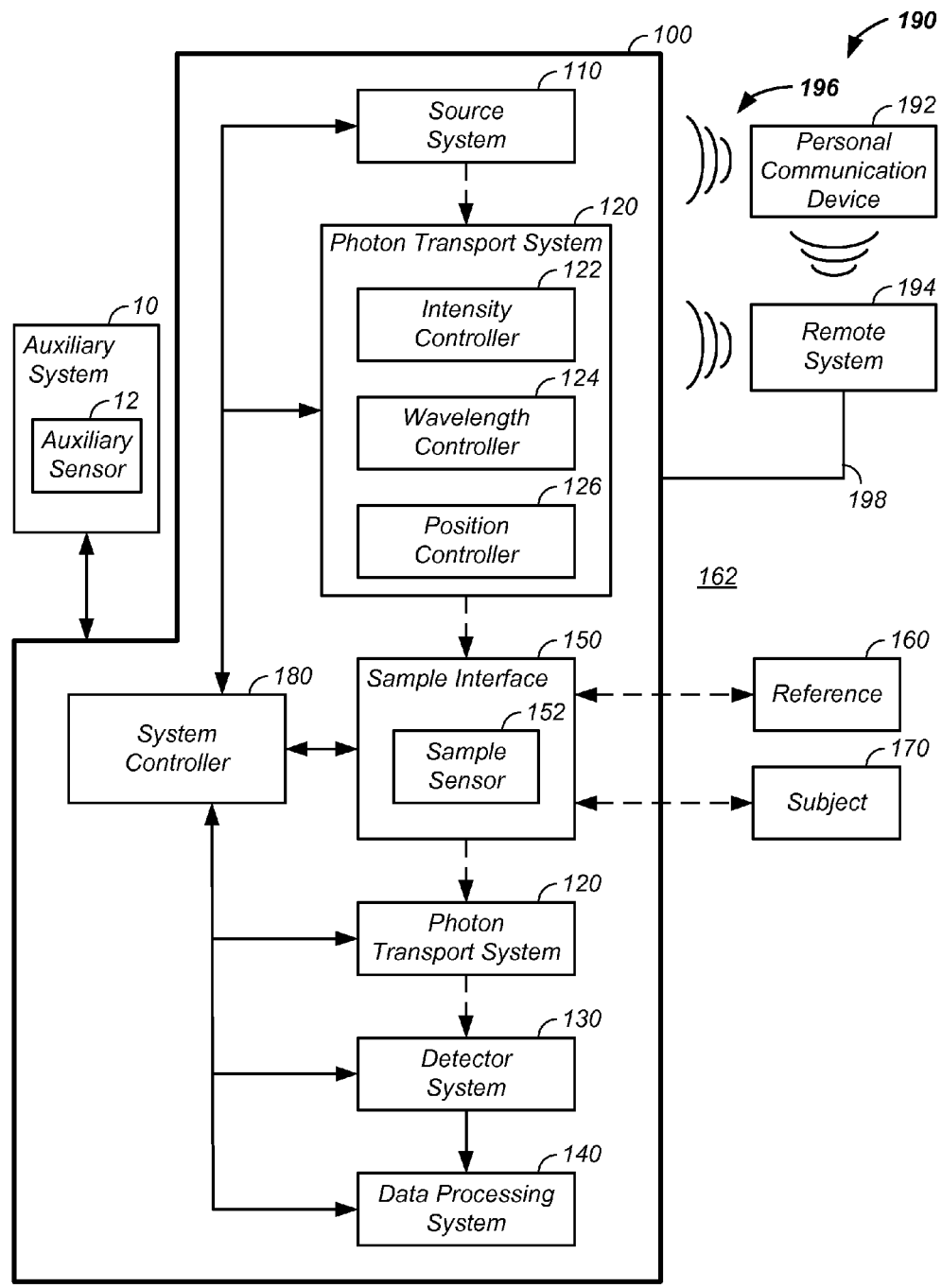
FIG. 1 illustrates an analyzer.

Elements and steps in the figures are illustrated for simplicity and clarity and have not necessarily been rendered according to any particular sequence. For example, steps that are performed concurrently or in a different order are illustrated in the figures to help improve understanding of embodiments of the present invention.

DETAILED DESCRIPTION OF THE PREFERRED EMBODIMENTS

The invention comprises two optically stacked arrays of optical filters as a portion of a noninvasive analyzer apparatus and method of use thereof. The stacked arrays of optical filters are optionally configured to pass multiple distinct and/or overlapping wavelength ranges to an array of detectors, where the filter combination—detector array distance resolves diffusely reflected/partially absorbed optical pathlengths through skin.

In another embodiment, a noninvasive analyzer apparatus and method of use thereof using a plurality of two-dimensional near-infrared detector arrays is described.

In yet another embodiment, subsets of signals from one or more two-dimensional detector array are used to determine at least one of: sampled pathlengths, internal consistency, precision enhancement, skin type, photon path information, outlier analysis, and state of the subject tested.

In still another embodiment, an apparatus and method of use thereof is described using acquisition of noninvasive mapping spectra of skin and subsequent optical/optical path reconfiguration for subsequent subject specific data collection.

For example, a near-infrared noninvasive analyzer is configured with a first optical configuration used to map an individual and/or group of individuals through use of mapping spectra. The mapping spectra are analyzed and used to reconfigure the optical setup of the analyzer to a second optical configuration suited to the individual and/or group of individuals. Subsequently, collection of noninvasive spectra of the individual and/or group of individuals is performed using the second optical configuration, which is preferably optimized to yield additional information based on the skin of the individual and/or group of individuals.

In yet another embodiment, a data processing system analyzes data from an analyzer to estimate and/or determine an analyte property, such as concentration using multiple types of data, such as from an external sensor, from two or more radial positions, and/or with two or more focusing depths.

In still another embodiment, an analyzer using light interrogates the sample using one or more of:
 a spatially resolved system;
  an incident light radial distance resolved system;
  a controllable and variable incident light solid angle system; and
  a controllable and variable incident light angle system;
 a time resolved system, where the times are greater than about 1, 10, 100, or 1000 microseconds;
 a picosecond timeframe resolved system, where times are less than about 1, 10, 100, or 1000 nanoseconds;

collection of spectra with varying radial distances between incident light entering skin and detected light exiting the skin;

an incident angle resolved system; and a collection angle resolved system.

Data from the analyzer is analyzed using a data processing system capable of using the information inherent in the resolved system data.

In yet another embodiment, a data processing system uses interrelationships of chemistry based a-priori spectral information related to absorbance of a sample constituent and/or the effect of the environment, such as temperature, on the spectral information.

In yet still another embodiment, a data processing system uses a first mapping phase to set instrument control parameters for a particular subject, set of subjects, and/or class of subjects. Subsequently, the control parameters are used in a second data collection phase to collect spectra of the particular subject or class of subjects.

In still yet another embodiment, a data processing system uses information related to contact pressure on a tissue sample site.

In another embodiment, a data processing system uses a combination of any of:

spatially resolved information;

temporally resolved information on a time scale of longer than about one microsecond;

temporally resolved information on a sub one hundred picosecond timeframe;

incident photon angle information;

photon collection angle information;

interrelationships of spectral absorbance and/or intensity information;

environmental information;

temperature information; and information related to contact pressure on a tissue sample site.

In still yet another embodiment, a temporal resolution gating noninvasive analyzer is used to determine an analyte property of a biomedical sample, such as a glucose concentration of a subject using light in the near-infrared region from 1000 to 2500 nanometers.

In yet still another embodiment, an apparatus and method of use thereof is described using a plurality of time resolved sample illumination zones coupled to at least one two-dimensional detector array monitoring a plurality of detection zones linked to the sample illumination zones.

Axes

Herein, axes systems are separately defined for an analyzer and for an interface of the analyzer to a patient, where the patient is alternatively referred to as a subject and/or a person.

Herein, when referring to the analyzer, an x, y, z-axes analyzer coordinate system is defined relative to the analyzer. The x-axis is in the direction of the mean optical path. The y-axis crosses the mean optical path perpendicular to the x-axis. When the optical path is horizontal, the x-axis and y-axis define a x/y horizontal plane. The z-axis is normal to the x/y plane. When the optical path is moving horizontally, the z-axis is aligned with gravity, which is normal to the x/y horizontal plane. Hence, the x, y, z-analyzer coordinate system is defined separately for each optical path element. If necessary, where the mean optical path is not horizontal, the optical system is further defined to remove ambiguity.

Herein, when referring to the patient, an x, y, z-axes patient coordinate system is defined relative to a body part interfaced to the analyzer. Hence, the x, y, z-axes body coordinate system moves with movement of the body part. The x-axis is defined along the length of the body part, the y-axis is defined across the body part. As an illustrative example, if the analyzer interfaces to the forearm of the patient, then the x-axis runs longitudinally between the elbow and the wrist of the forearm and the y-axis runs across the forearm. Together, the x,y plane tangentially touches the skin surface at a central point of the interface of the analyzer to the body part, which is referred to as the center of the sample site, sample region, or sample site. The z-axis is defined as orthogonal to the x,y plane. Rotation of an object is further used to define the orientation of the object to the sample site. For example, in some cases a sample probe of the analyzer is rotatable relative to the sample site. Tilt refers to an off z-axis alignment, such as an off z-axis alignment of a probe of the analyzer relative to the sample site.

Analyzer

Referring now and throughout to FIG. 1, an analyzer 100 is illustrated. The analyzer comprises at least: a light source system 110, a photon transport system 120, a detector system 130, and a data processing system 140, where the data processing system is optionally remotely located from the source/sample/detector system. In use the analyzer 100 estimates and/or determines a physical property, a sample state, a constituent property, and/or a concentration of an analyte.

Patient/Reference

Still referring to FIG. 1, an example of the analyzer 100 is presented. In this example, the analyzer 100 includes a sample interface 150, which interfaces to a reference material 160 and/or to a subject 170. Herein, for clarity of presentation a subject 170 in the examples is representative of a person, animal, a prepared sample, and/or a patient. In practice, the analyzer 100 is used by a user to analyze the user, referred to as the subject 170, and/or is used by a medical professional to analyze a patient.

Controller

Figure 4:
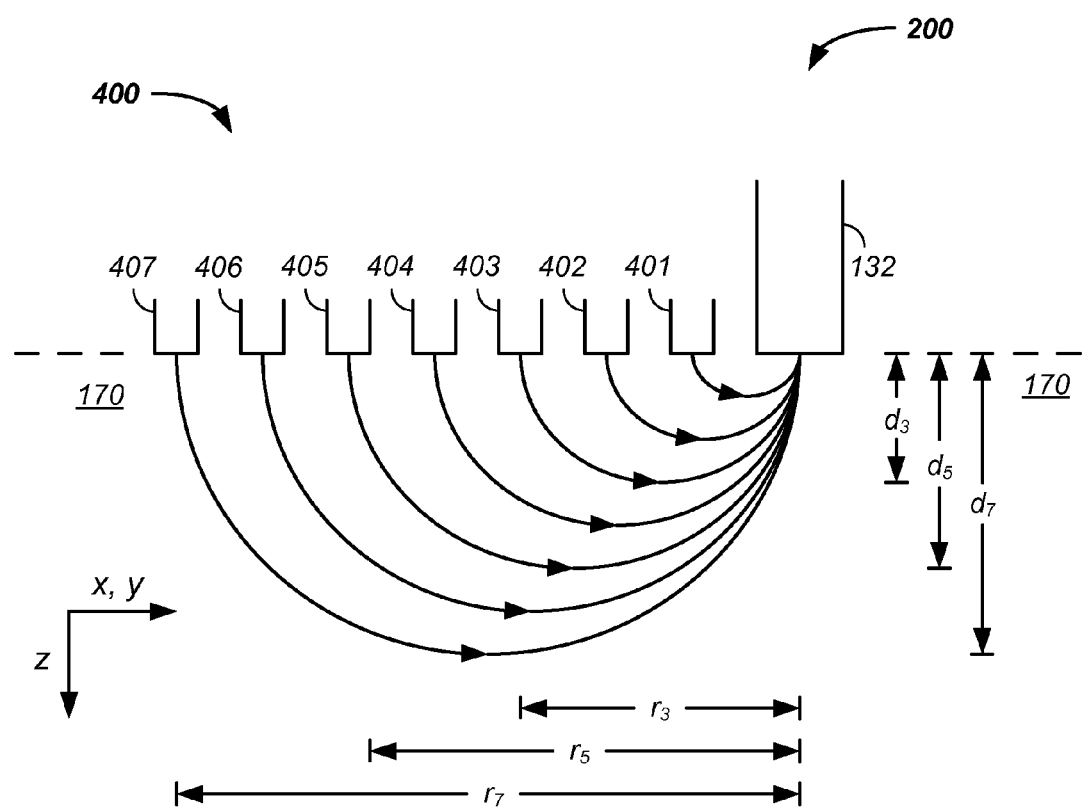
FIG. 4 illustrates varying illumination zones relative to a detector.
Figure 5:
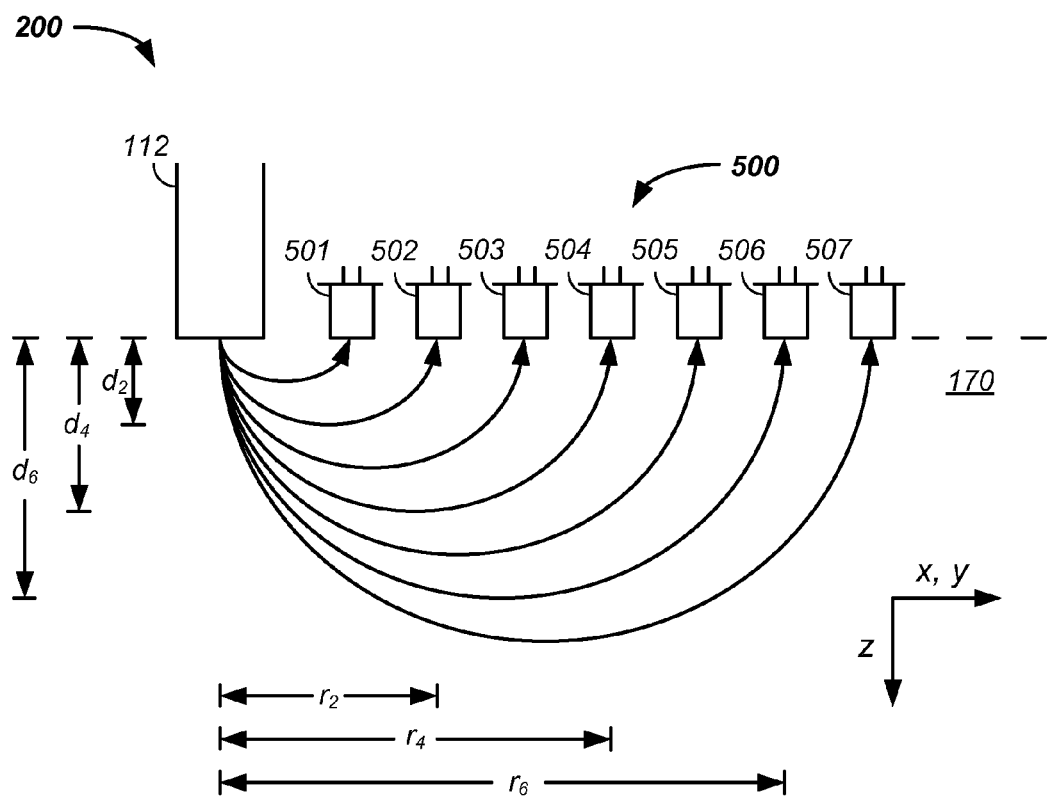
FIG. 5 illustrates varying detection zones relative to an illuminator.

Still referring to FIG. 1 and referring now to FIGS. 4 and 5, the analyzer 100 optionally includes a system controller 180 or controller. The system controller 180 is used to control one or more of: the light source system 110 or a light source 112 thereof, the photon transport system 120, the detector system 130 or a detector 132 thereof, the sample interface 150, position of the reference 160 relative to the sample interface 150, position of the subject 170 relative to the sample interface 150, and/or communication to an outside system 190, such as a personal communication device 192, a smart phone, and/or a remote system 194 using a wireless communication system 196 and/or a hard wired communication system 198. For example, the remote system includes a data processing system, a data storage system, a data transfer system, and/or a data organization system.

Still referring to FIG. 1, the optional system controller 180 operates in any of a predetermined manner or in communication with the data processing system 140. In the case of operation in communication with the data processing system 140, the controller generates control statements using data and/or information about the current state of the analyzer 100, current state of a surrounding environment 162 outside of the analyzer 100, information generated by the data processing system 140, and/or input from a sensor, such as a sample interface sensor 152 or an auxiliary system 10 or an auxiliary sensor 12 thereof. Herein, the auxiliary system 10 is any system providing input to the analyzer 100.

Still referring to FIG. 1, the optional system controller 180 is used to control:

photon intensity of photons from the source using an intensity controller 122, wavelength distribution of photons from the source 110 using a wavelength controller 124, physical routing of photons from the source 110 using a position controller 126. and/or timing of photon delivery.

Still referring to FIG. 1, for clarity of presentation the optional outside system 190 is illustrated as using a personal communication device 192, such as a smart phone. However, the personal communication device 192 is optionally a cell phone, a tablet computer, a phablet, a computer network, a personal computer, and/or a remote data processing center. Similarly, the smart phone also refers to a feature phone, a mobile phone, a portable phone, and/or a cell phone. Generally, the personal communication device 192 includes hardware, software, and/or communication features carried by an individual that is optionally used to offload requirements of the analyzer 100. For example, the personal communication device 192 includes a user interface system, a memory system, a communication system, and/or a global positioning system. Further, the personal communication device 192 is optionally used to link to the remote system 194, such as a data processing system, a medical system, and/or an emergency system. In another example at least one calculation of the analyzer 100 in noninvasively determining a glucose concentration of the subject 170 is performed using the personal communication device 192. In yet another example, the analyzer gathers information from at least one auxiliary sensor 12 and relays that information and/or a processed form of that information to the personal communication device 192, where the auxiliary sensor is not integrated into the analyzer 100. Optionally data from the analyzer 100 is processed in the cloud or a remote computing facility. Optionally, the personal communication device 192 is used as a portal between the analyzer 100 and the cloud. Optionally, the remote system 194 is a data processing center configured to receive signal from more than one analyzer and to return a calculated analyte concentration and/or an analyte property to the corresponding analyzer and/or to a communication device of the user of the corresponding analyzer.

Source

Herein, the source system 110 generates photons in any of the visible, infrared, near-infrared, mid-infrared, and/or far-infrared spectral regions. In one case, the source system generates photons in the near-infrared region from 1100 to 2500 nm or any range therein, such as within the range of about 1200 to 1800 nm; at wavelength longer than any of 800, 900, 1000, and 1100 nm; and/or at wavelengths shorter than any of 2600, 2500, 2000, or 1900 nm.

Photon/Skin Interaction

Light interacts with skin through laws of physics to scatter and transmit through skin voxels also referred to as volume pixels or skin volumes.

Figure 2:
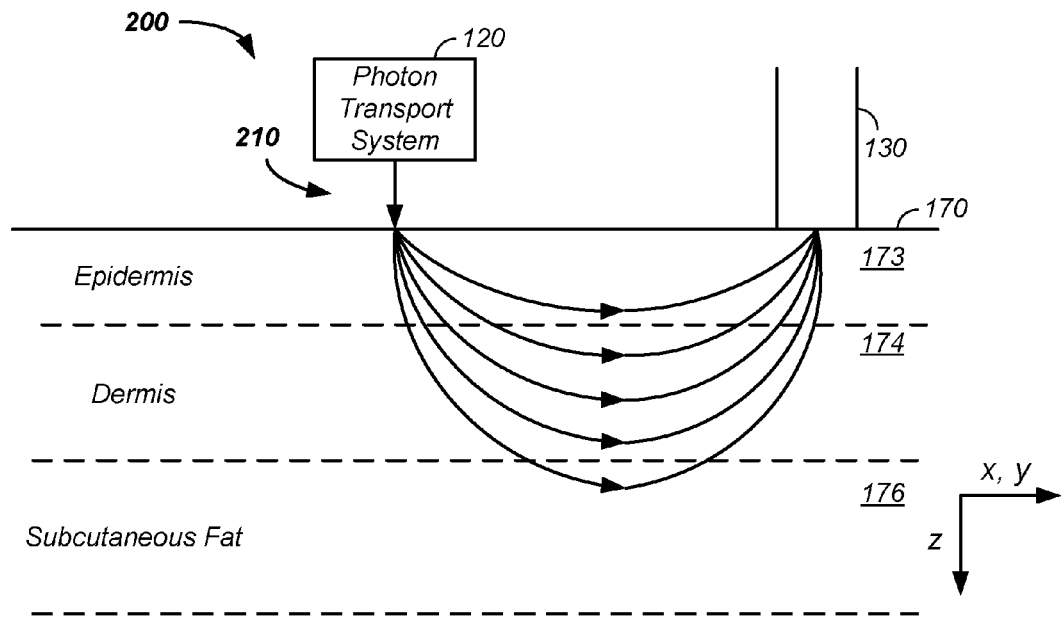
FIG. 2 illustrates diffusely reflecting optical paths.

Referring now to FIG. 2, for clarity of presentation and without limitation, in several examples provided herein a simplifying and non-limiting assumption is made, for some wavelengths, for some temperatures, and for some optical configurations, that a mean photon depth of penetration, with subsequent detection at the incident surface of the subject, increases with mean radial distance between a photon illumination zone and a photon detection zone. For example, for photons transmitting from a sample illumination zone, through the subject, and through a photon detection zone, such as at a subject/analyzer interface:

at a first radial distance, photons penetrate with a mean maximum depth of penetration into an epidermal layer of a subject;

at a second larger radial distance, photons penetrate with a mean maximum depth of penetration into a dermal layer of the subject; and at a third still larger radial distance, photons penetrate with a mean maximum depth of penetration into a subcutaneous fat layer of the subject.

Referring still to FIG. 2 and referring again to FIG. 5, a photon transit system 200 through skin layers of the subject 170 is illustrated. In this example, the photon transport system 120 guides light from a source 112 of the source system 110 to the subject 170, optionally with an air gap 210 between a last optic of an illumination system and skin of the subject 170. Further, in this example, the photon transport system 120 irradiates skin of the subject 170 over a narrow illumination zone, such as having an area of less than about 9, 4, 1, 0.25, 0.1, and/or 0.01 mm². Optionally, the photons are delivered to the skin of the subject 170 through an optic or set of optics proximately contacting, but not actually contacting, the skin, such as within about 0.5, 1.0, or 2.0 millimeters of the skin. Optionally, the distance between the analyzer and the skin of the subject 170 is maintained with a vibration and/or shake reduction system, such as is used in a vibration reduction camera or lens. For instance, shake of the sample site is monitored and the optical system is dynamically adjusted to compensate for movement of the sample site. For clarity of presentation, the photons are depicted as entering the skin at a single point. A portion of the photons traverse, or more particularly traverse through, the skin to a detection zone. The detection zone is a region of the skin surface where the detector system 130 gathers the traversing or diffusely reflected photons. Various photons traversing or diffusely scattering through the skin encounter a stratum corneum, an epidermis 173 or epidermis layer, a dermis 174 or dermis layer, and subcutaneous fat 176 or a subcutaneous fat layer. As depicted in FIG. 2, the diffuse reflectance of the various photons through the skin detected by the detection system 130 follow a variety of optical paths through the tissue, such as shallow paths through the epidermis 173, deeper paths through the epidermis 173 and dermis 174, and still deeper paths through the epidermis 173, dermis 174, and subcutaneous fat 176. However, for a large number of photons, there exists a mean photon path for photons from a point entering the skin until exiting the skin and being detected by the detection system 130. In the illustrations, optical pathlengths are illustrated as straight lines and/or curved lines for clarity of presentation; in practice light travels in straight lines between multiple scattering events.

Pathlength

Herein, for clarity, without loss of generality and without limitation, Beer's Law is used to describe photon interaction with skin, though those skilled in the art understand deviation from Beer's Law result from sample scattering, index of refraction variation, inhomogeneity, turbidity, anisotropy, and/or absorbance out of a linear range of the analyzer 100.

Beer's Law, equation 1, states that:

$$A \alpha b C \qquad (eq. 1)$$

where A is absorbance, b is pathlength, and C is concentration. Typically, spectral absorbance is used to determine concentration. However, the absorbance is additionally related to pathlength. Hence, determination of the optical pathlength traveled by the photons is useful in reducing error in the determined concentration. Two methods, described infra, are optionally used to estimate pathlength: (1) spatial resolution of pathlength and (2) temporal resolution of pathlength.

Algorithm

The data and/or derived information from each of the spatial resolution method and temporal resolution method are each usable with the data processing system 140. Examples provided, infra, illustrate: (1) both cases of the spatial resolution method and (2) the temporal resolution method. However, for clarity of presentation and without limitation, the photons in most examples are depicted as radially traversing from a range of input zones to a range of detection zones. Similarly, photons are optionally delivered, simultaneously and/or as a function of time, from an input zone to a range of detection zones. Still further, photons are optionally directed to a series of input zones, as a function of time, and one or more detection zones are used to detect the photons directed to the series of input zones, simultaneously and/or as a function of time. Yet still further, sets of photons of controlled wavelengths are delivered to corresponding incident positions on the skin and filters and/or detectors are configured at additional locations on the skin.

Spatial Resolution

The first method of spatial resolution contains two cases. Herein, in a first case photons are depicted traversing from a range of input points on the skin to a radially located detector to derive photon interrogated sample path and/or depth information. However, in a second case, similar systems optionally use a single input zone of the photons to the skin and a plurality of radially located detector zones to determine optically sampled photon paths and/or depth information. Still further, a combination of the first two cases, such as multiple sources or multiple illumination zones, and/or multiple detectors, is optionally used to derive photon path information in the skin.

Figure 3:
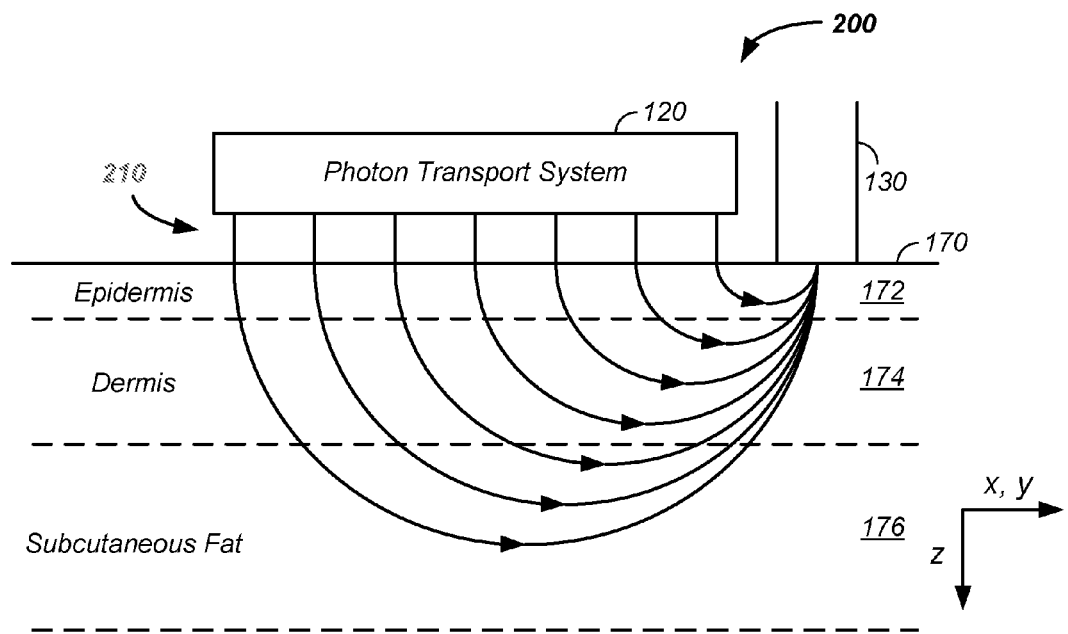
FIG. 3 illustrates probing tissue layers using a spatial distribution method.

In a first system, still referring to FIG. 2 and referring now to FIG. 3, the photon transit system 200 of FIG. 2 is illustrated where the photon transport system 120 irradiates the skin of the subject 170 over a wide range of radial distances from the detection zone, such as at least about 0.1, 0.2, 0.3, 0.4, or 0.5 millimeters from a center or edge of the detection zone to less than about 1.0, 1.2, 1.4, 1.6, or 1.8 millimeters from a center or edge of the detection zone. In this example, a mean photon path is provided as a function of radial distance from the illumination zone to the detection zone. Generally, over a range of about zero to less than about two millimeters from the detection zone and in the range of 1100 to 2500 nm, the mean optical path of the detected diffusely scattered photons increases in depth as a function of radial distance.

In the first case of the spatial resolution method, referring now to FIG. 4, the photon transit system 200 uses a vector or array of illumination sources 400, of the source system 110, in a spatially resolved pathlength determination system. For example, the illumination sources are an array of fiber optic cables, an array of light emitting diodes, light passing through an array of optical filters, and/or an array of illumination zones. In this example, a set of seven fiber optics 401, 402, 403, 404, 405, 406, 407 are positioned, radially along the x,y plane of the subject 170 to provide a set of illumination zones, relative to a detection fiber at a detection zone. As illustrated the third illumination fiber optic 403/detector 132 combination yields a mean photon path having a third mean depth of penetration, $d_3$, for a third fiber optic-to-detector radial distance, $r_3$; the fifth illumination fiber optic 405/detector 132 combination yields a mean photon path having a fifth mean depth of penetration, $d_5$, for a fifth fiber optic-to-detector radial distance, $r_5$; and the seventh illumination fiber optic 407/detector 132 combination yields a mean photon path having a seventh mean depth of penetration, $d_7$, for a seventh fiber optic-to-detector radial distance, $r_7$. Generally, for photons in the near-infrared region from 1100 to 2500 nanometers, both a mean depth of penetration of the photons and a total optical pathlength increases with increasing illumination zone-to-detection zone distance, where the illumination zone-to-detection zone distance is less than about three millimeters.

In the second case of the spatial resolution method, referring now to FIG. 5, the photon transit system 200 uses a vector or array of detectors 500 in the detection system 130. For example, an illumination zone source, such as a single fiber optic source, sends radially distributed light to an array of staring detectors or collection optics coupled to a set of detectors. In this example, a set of seven detectors 501, 502, 503, 504, 505, 506, 507 are positioned radially along the x,y plane to provide a set of detection zones relative to the illumination zone. As illustrated the source 112/second detector 502 combination yields a mean photon path having a second mean depth of penetration, $d_2$, for a second illumination zone-to-detection zone radial distance, $r_2$; the source 112/fourth detector 504 combination yields a mean photon path having a fourth mean depth of penetration, $d_4$, for a fourth illumination zone-to-detection zone radial distance, $r_4$; and the source 112/sixth detector 506 combination yields a mean photon path having a sixth mean depth of penetration, $d_6$, for a sixth illumination-to-detection zone radial distance, $r_6$. Again, generally for photons in the near-infrared region from 1400 to 2500 nanometers both the mean depth of penetration of the photons into skin and the total optical pathlength in skin increases with increasing illumination zone-to-detection zone distance, where the illumination zone-to-detection zone distance, such as a fiber optic-to-detector distance, is less than about three millimeters. Hence, data collected with an analyzer configured with a multiple detector design generally corresponds to the first case of a multiple source design, albeit with different sample volumes due to tissue layers, tissue inhomogeneity, and tissue scattering properties.

Referring again to FIGS. 4 and 5, the number of illumination zones, where light enters skin of the subject 170, from one or more source elements, is optionally 1, 2, 3, 4, 5, 10, 20, 50, 100 or more and the number of detection zones, where light exiting the skin of the subject 170 is detected by one or more detection elements and/or systems, such as 1, 2, 3, 4, 5, 10, 20, 50, 100, 500, 1000, 5000, 10,000, 50,000 or more detection elements.

Two Dimensional Detector Array System

Figure 6A:
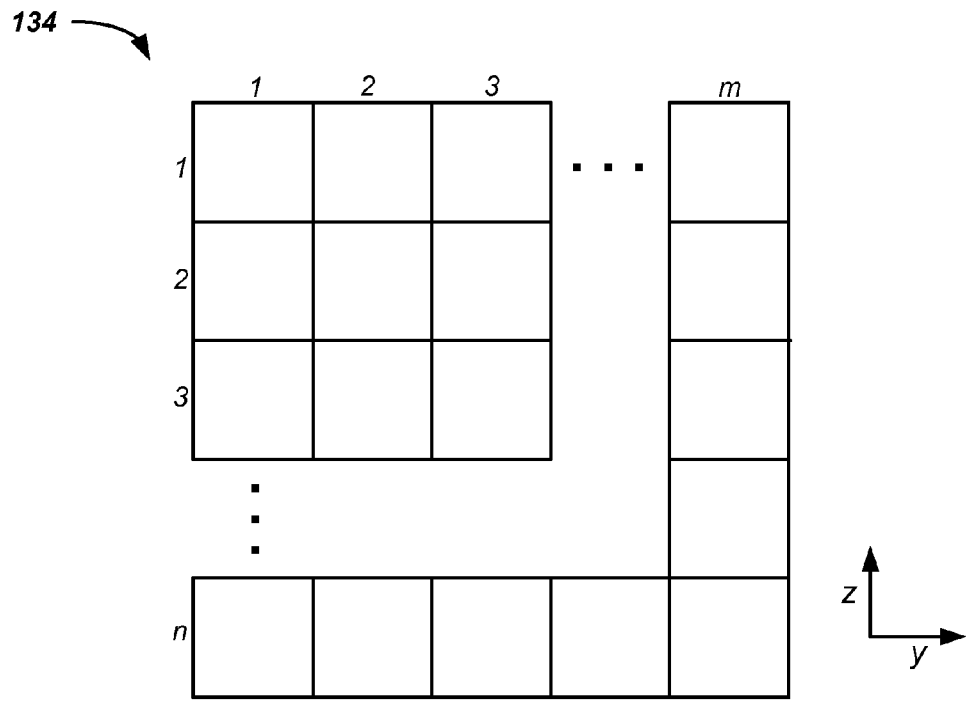
FIG. 6A illustrates an end view of a detector array and FIG. 6B illustrates a side view of the detector array.

Referring now to FIG. 6A, a m×n two-dimensional detector array 134 is illustrated, which is an example of the detector 132 in the detection system 130. Herein, the m×n two-dimensional detector array 134 is illustrated as a matrix of m columns by n rows, where m and n are each, not necessarily equal, positive integers, such as greater than 1, 2, 3, 4, 5, 10, 20, 50, 100. Optionally, the two-dimensional detector array 134 is of any geometric configuration, shape, or pattern. Preferably, but optionally, the two-dimensional detector array 134 is positioned perpendicular and axial to the optical light path at the detector. Optionally, the two-dimensional detector array 134 or a portion thereof is tilted off of the perpendicular axis, such as less than 1, 2, 3, 5, 10, or 15 degrees toward the skin of the subject 170, which yields a range of applied pressures between the two-dimensional detector array and the skin when the two-dimensional detector array 134 or a layer thereon contacts the skin.

Figure 6B:
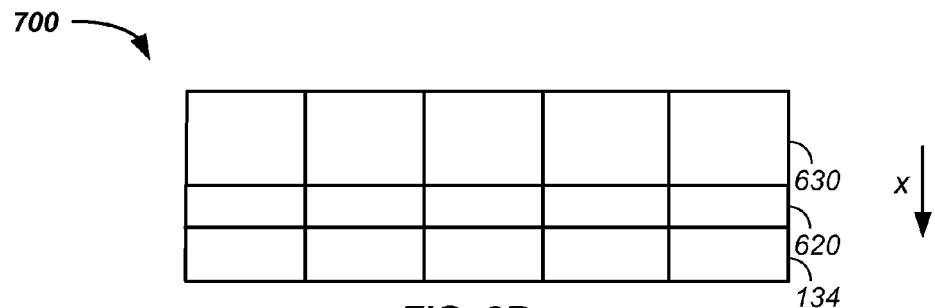

Referring now to FIG. 6B, an optional configuration of the two-dimensional detector array 134 is further described. Optionally, one or more elements of the two-dimensional detector array 134 are coated or coupled with an optical detector filter 620. In a first case, the optical detector filter 620 is uniform across the two-dimensional detector array 134. In a second case, the optical detector filter 620 comprises an array of filters, where individual elements, grids, or zones of the optical filter correspond to individual elements of the two-dimensional detector array 134. For example, a group of at least 1, 2, 4, 9, 16, or 25 elements of the two-dimensional detector array 134 are optically coupled with a first optical filter and a group of at least 1, 2, 4, 9, 16, or 25 elements of the two-dimensional detector array 134 are optically coupled to a second filter. Optionally, any number of filter types are used with a single detector array, such as 1, 2, 3, 4, 5, 10, 20 or more filter types. In a preferred embodiment, a first, second, third, fourth, and fifth filter type correspond with peak transmittance in ranges in the 1100 to 1450 nm range, 1450 to 1900 nm range, 1100 to 1900 nm range, 1900 to 2500 nm range, or 1100 to 2500 nm range, respectively, with lower transmittances, such as less than 50, 25, or 10 percent at higher and/or lower frequencies. In a third case, the optical filter 134 comprises a repeating pattern of transmittances and/or absorbances as a function of y, z-position.

Still referring to FIG. 6B, the two-dimensional detector array 134 is optionally coupled to a detector optic/micro-optic layer 630. In a first case, individual optical elements of the micro-optic layer 630 optionally:

- alter a focal depth of incident light onto the two-dimensional detector array 134;
- alter an incident angle of incident light onto the two-dimensional detector array 134;
- focus on an individual element of the two-dimensional detector array 134; and/or
- focus on groups of detection elements of the two-dimensional detector array 134.

In a second case, individual lines, circles, geometric shapes covering multiple detector elements, and/or regions of the micro-optic layer optionally:

- alter a focal depth of incident light onto a line, circle, geometric shape, and/or region of the two-dimensional detector array 134;
- alter an incident angle of incident light onto a line, circle, geometric shape, and/or region of the two-dimensional detector array 134; and/or
- focus onto a line, circle, geometric shape, and/or region of a group of elements of two-dimensional detector array 134.

Further the individual optical elements of the micro-optic layer 630 and/or the individual lines, circles, geometric shapes, or regions of the micro-optic layer 630 optionally are controlled by the system controller 180 to change any of the focal depth and/or an incident angle of incident light as a function of time within a single data collection period for a particular subject and/or between subjects.

Still referring to FIG. 6B, the optical detector filter 620 is:

- optionally used with or without the detector optic/micro-optic layer 630; and/or
- optionally contacts, proximately contacts, or is separated by a detector filter/detector gap distance from the two-dimensional detector array 134.

Similarly, the detector optic/micro-optic layer 630 is:

- optionally used with or without the optical detector filter 620; and/or
- optionally contacts, proximately contacts, or is separated by a micro-optic/detector gap distance 632 from the two-dimensional detector array 134.

Referring now to FIGS. 7(A-E), optionally and preferably an incident optic/two-dimensional detector array system 700 is enclosed in a housing. For example, optionally and preferably, the detector array, first optical filter array, second optical filter array, and/or focusing optic array are sandwiched together, where two or more of the stacked layers are substantially contacting along an interfacing plane. The first and/or second optical filter arrays are optionally placed along the optical axis on either side of the focusing optic/light gathering array. The housing serves a number of purposes, such as the ability to prevent dust/particulate infiltration; is an enclosure sealed against moisture, allowing the detectors to be operated below a dew point, such as via use of 2, 3, or four layers of Peltier coolers; allows use of a partial vacuum within the enclosure; and/or allows a substantially non-water containing gas to be placed in the housing to minimize condensation.

Referring still to FIGS. 7(A-E), for clarity of presentation, the incident optic/two-dimensional detector array system 700 is illustrated in multiple representative configurations, without loss of generality or limitation.

Figure 7A:
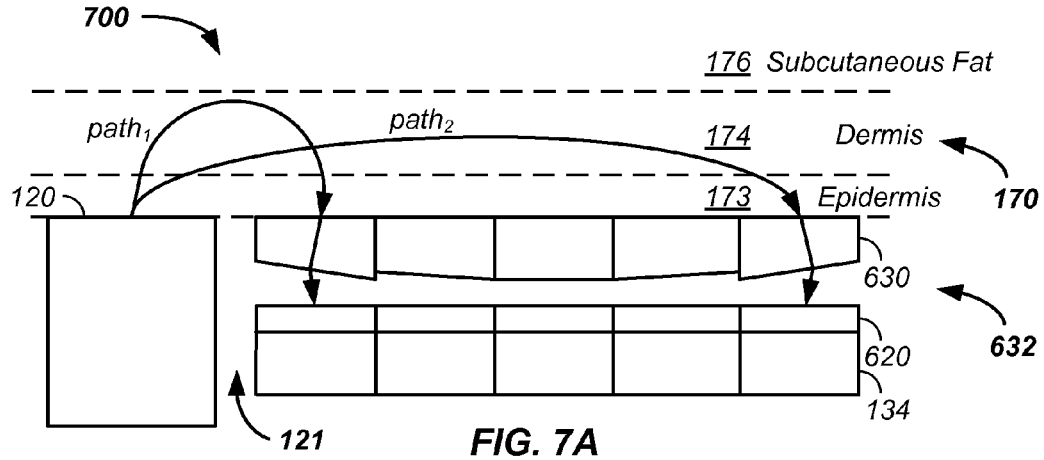
FIGS. 7(A-E) illustrate a coupled source detector array system, FIG. 7A; a side illuminated/detector array system, FIG. 7B; a corner illuminated/detector array system, FIG. 7C; a within array illumination system, FIG. 7D; and an illuminated array/detector array system, FIG. 7E.

Referring now to FIG. 7A, a first example of the incident optic/two-dimensional array system 700 is illustrated with the photon transport system 120 used to deliver photons to the subject 170 proximate the two-dimensional detector array 134. In a first example, a portion of photons from the photon transport system diffusely scatter through skin of the subject 170 and after radial movement emerge from the skin of the subject 170 where a portion of the incident photons are detected by elements of the two-dimensional detector array 134. In a first example, photons are illustrated travelling along: (1) a first mean path, $path_1$, and are detected by a first detector element of the two-dimensional detector array 134 at a first, smaller, mean radial distance from a tissue illumination zone of the photon transport system and (2) a second mean path, $path_2$, are detected by a second detector element of the two-dimensional detector array 134 at a second, longer, mean radial distance from a tissue illumination zone of the photon transport system relative to $path_1$. In this first example, optionally:

- a first element of the optical detector filter 620 is preferably a filter designed for a shorter mean tissue pathlength, such as about 0 to 1.5 millimeters, such as a combination band optical filter with a peak transmittance in a range of 2000 to 2500 nm;
- a second element of the optical detector filter is preferably a filter designed for a longer mean tissue pathlength, such as about 5.0 to 10 millimeters, such as a second overtone optical filter with a peak transmittance in a range of 1100 to 1450 nm; and
- a third element of the optical detector filter is preferably a filter designed for an intermediate mean tissue pathlength, such as about 1.5 to 5.0 millimeters, such as a first overtone optical filter with a peak transmittance in a range of 1450 to 1900 nm.

In the first example,

- a first element of the detector optic/micro-optic layer 630 is optionally configured to preferably collect incident skin interface light having an angle aimed back toward the photon transport system, which yields a slightly shorter mean tissue pathlength, such as about 0.2 to 1.7 millimeters compared to an optic that is flat/parallel relative to the skin of the subject 170;
- a first element of the detector optic/micro-optic layer 630 is optionally configured to redirect collected incident skin interface light back away from the photon transport system 120 as illustrated, such as onto a center of a detector or detector array element closer to the illumination zone;
- a second element of the detector optic/micro-optic layer 630 is optionally configured to preferably collect incident skin interface light having an angle aimed away from the incident illumination zone of the skin, which yields a slightly shorter mean tissue pathlength compared to an optic that is flat/parallel relative to the skin of the subject 170;

a second element of the detector optic/micro-optic layer 630 is optionally configured to redirect collected incident skin interface light back toward the incident skin illumination zone, such as onto a center of a detector or detector array element further from the illumination zone;

a third element of the detector optic/micro-optic layer 630 is optionally flat/parallel relative to a mean plane between the skin of the subject 170 and the two-dimensional detector array 134.

As described, supra, the individual optical elements of the micro-optic layer 630 and/or the individual lines, circles, geometric shapes, or regions of the micro-optic layer 630 are optionally dynamically controlled by the system controller 180 to change any of a detector layer incidence acceptance angle, the focal depth, an incident angle, and/or an emittance angle or exit angle as a function of time within a single data collection period for a particular subject and/or between subjects.

Still referring to FIG. 7A, an optional micro-optic layer/detector array gap 632 is illustrated between the detector optic/micro-optic layer 630 and elements of the two-dimensional detector array 134, such as a gap less than 0.2, 0.5, 1, 2, 5, or 10 millimeters. Further, an optional spacer gap 121 is illustrated between a final incident optic of the photon transport system 120 and any of the two-dimensional detector array 134, the optical detector filter 620, and/or the detector optic/micro-optic layer 630, such as a gap of less than about 0.1, 0.2, 0.3, 0.4, 0.5, 0.75, and/or 1.0 millimeter.

Figure 7B:
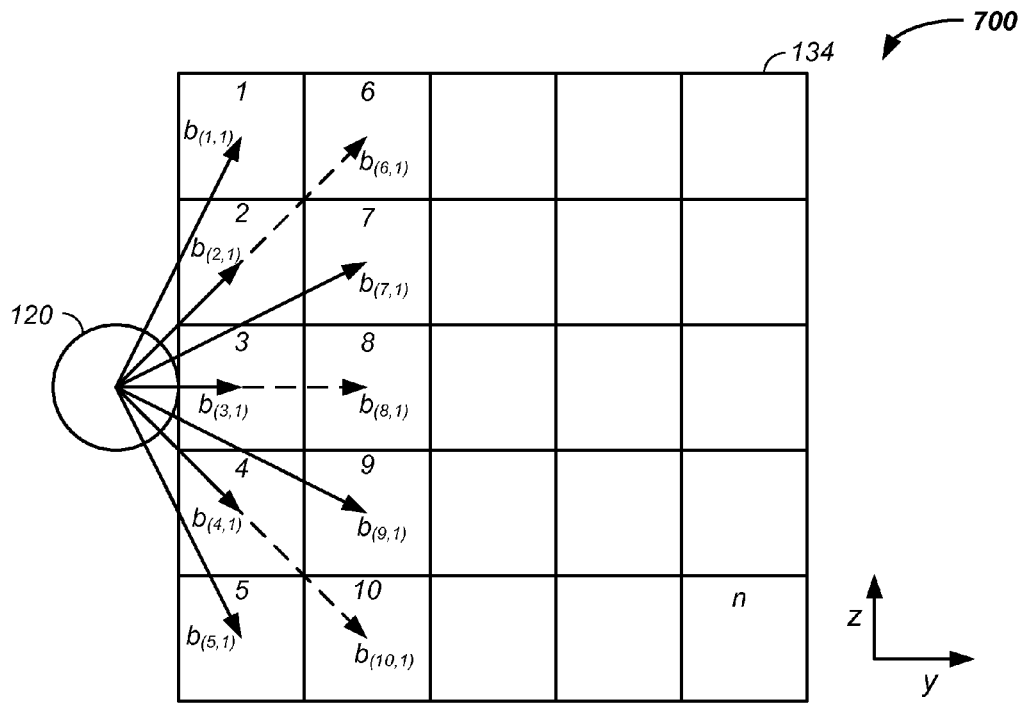

Referring now to FIG. 7B, a second non-limiting example of the incident optic/two-dimensional detector array system 700 is illustrated with the photon transport system 120 used to deliver photons to the subject 170 proximate a first side of the two-dimensional detector array 134, where the array has n detector elements, where n is a positive integer greater than three. In this second example, ten radial distances to ten detector elements are illustrated. In this example, some radial distances are equal, such as a first radial distance to detector elements 1 and 5 and a second radial distance to detector elements 2 and 4. Generally, detector elements are optionally grouped or clustered into radial distances relative to an illumination zone of 1, 2, 3, or more incident light directing elements where each group or cluster is individually associated with an average mean optical probed tissue pathlength, subsequently used in pathlength resolution, and/or analyte concentration estimation.

Still referring to FIG. 7B, optionally, different clusters of radial distances are treated optically differently, such as with a different optical detector filter 620. Representative and non-limiting examples include:

a combination band filter for filtering photons having mean radial distances of 0 to 1 millimeter, the combination band filter comprising:
  a transmittance greater than seventy percent at 2150 nm, 2243, and/or 2350 nm, and/or
  an average transmittance of greater than seventy percent from 2100 to 2400 nm and an average transmittance of less than twenty percent from 1100 to 1900 nm and/or from 2400 to 2600 nm;

a first overtone band filter for filtering photons having mean radial distances of 0.3 to 1.5 millimeters, the first overtone filter comprising:
  a transmittance greater than seventy percent at 1550 nm, 1600, and/or 1700 nm, and/or
  an average transmittance of greater than seventy percent from 1500 to 1800 nm and an average transmittance of less than twenty percent from 1100 to 1400 nm and/or from 2000 to 2600 nm;

a combination band/first overtone band filter for filtering photons having mean radial distances of 0 to 1.5 millimeters, the combination/first overtone filter comprising:
  a transmittance greater than seventy percent at 1600 and 2100 nm, and/or
  an average transmittance of greater than seventy percent from 1500 to 2300 nm and an average transmittance of less than twenty percent from 700 to 1400 nm and/or from 2500 to 2800 nm;

a second overtone band filter for filtering photons having mean radial distances of 0.5 to 3.0 millimeters, the second overtone filter comprising:
  a transmittance greater than seventy percent at 1200 nm, 1300, and/or 1400 nm, and/or
  an average transmittance of greater than seventy percent from 1100 to 1400 nm and an average transmittance of less than twenty percent from 700 to 1000 nm and/or from 1500 to 2000 nm;

a first overtone band/second overtone band filter for filtering photons having mean radial distances of 0.5 to 3.0 millimeters, the first overtone band/second overtone band filter comprising:
  a transmittance greater than seventy percent at 1300 and 1600 nm, and/or
  an average transmittance of greater than seventy percent from 1200 to 1700 nm and an average transmittance of less than twenty percent from 700 to 1000 nm and/or from 2000 to 3000 nm;

a sloping overtone band filter or step function overtone band filter for filtering photons having mean radial distances of 0.5 to 3.0 millimeters, the sloping overtone band filter comprising:
  a mean transmittance greater than ten percent at 1300 nm, less than fifty percent at 1300 nm, and greater than seventy percent at 1600 nm, and/or
  an average transmittance between 1100 and 1300 nm in the range of ten to fifty percent and an average transmittance between 1500 and 1700 nm of greater than seventy percent with optional out of band blocking from 700 to 1000 nm and/or from 2500 to 3000 nm of greater than ninety percent; and/or a luminance filter for filtering photons having mean radial distances of 0 to 5 millimeters, the luminance filter comprising:
  an optical spacing element designed to maintain focal length;
  a mean transmittance greater than seventy percent from 1100 to 1800 nm, and/or
  a mean transmittance greater than seventy percent from 1100 to 2400 nm and an average transmittance of less than twenty percent from 700 to 1100 nm and/or from 2000 to 2600 nm.

Figure 7C:
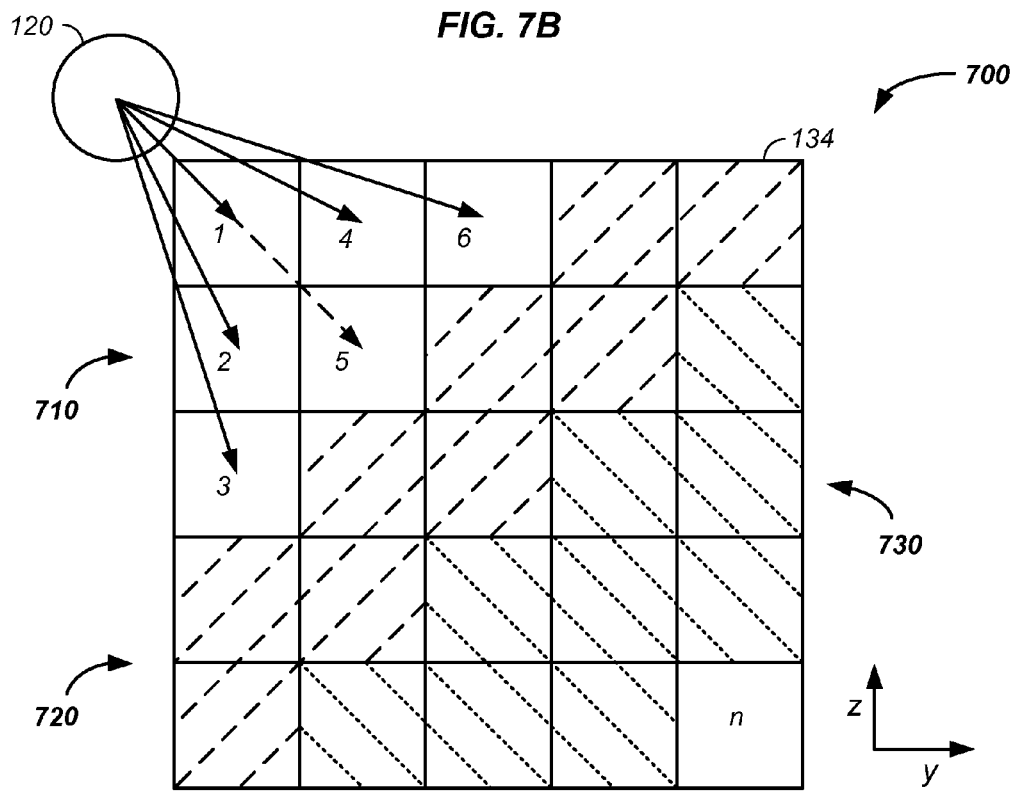
Figure 7D:
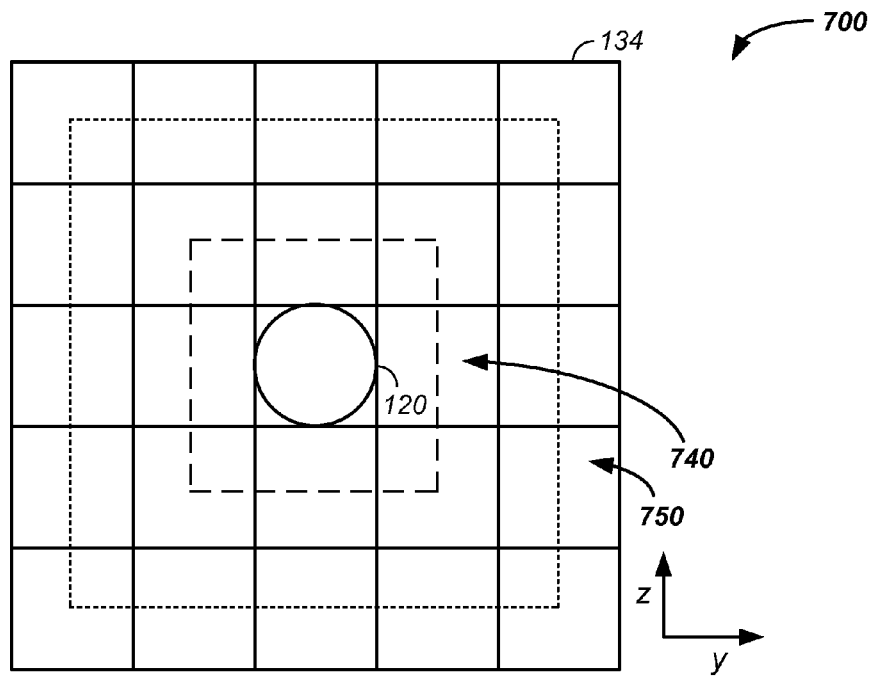

Referring now to FIGS. 7B, 7C, and 7D, the photon transport system 120 is illustrated as delivering light to an edge, corner, and interior region of the two-dimensional detector array 134, respectively. Descriptions, herein, to the edge, corner, or interior illumination options optionally apply to the other cases.

Referring again to FIG. 7B, the photon transport system 120 is illustrated delivering photons using at least one fiber optic and/or through one or more optics to a point or illumination zone along an edge of the two-dimensional detector array 134. For clarity of presentation, in a first case, the photon transport system 120 is illustrated delivering photons to a center of an edge of the two-dimensional detector array 134; however, the photon transport system 120 optionally delivers photons to any point along the edge of the two-dimensional detector array 134 and/or at any distance from an edge or corner of the two-dimensional detector array.

Still referring to FIG. 7B, as illustrated the photon transport system delivers photons that are detected with an array of mean pathlengths and associated mean depths of penetration into the tissue of the subject 170, at each detector element. For example, the first detector element, 1, detects photons having a first mean pathlength for a first illumination point, herein denoted $b_{(pathlength, illuminator)}$. In the first case, using a simplifying assumption of tissue homogeneity for clarity of presentation, the mean probed pathlength is the same at the first and fifth detector elements. Similarly, the mean probed pathlength is similar and/or tightly grouped at the second and fourth detector element. In addition, groups of detector elements observe photons traversing similar or grouped pathlengths. For example, a first sub-group of the first, sixth, and seventh detector elements observe similar probed tissue pathlengths and depths of penetration. Similarly, a second sub-group of the fifth, ninth, and tenth detector elements observe similar probed tissue pathlengths and depths of penetration. In this case, the first sub-group and second sub-group are optionally placed into a single group as the first sub-group and second sub-group observe similar, exact if the tissue is homogenous, probed tissue pathlengths. Similarly, a first sub-group is optionally one, two, three, or more elements of a first column of detector elements and a second sub-group is optionally one, two, three, or more elements of a second column of the detector elements. Generally, the detector elements are optionally treated individually or in sub-groups, such as by distance from a mean sample illumination point, sub-groups of one or more rows of detector element, sub-groups of one or more columns of detector elements, and/or groups of sub-groups.

Still referring to FIG. 7B, any two-dimensional detector array 134 element, sub-group, column, row, region, and/or group is optionally individually coated or coupled to any filter, such as the filters described supra, and/or is optionally individually coupled with a focusing optic and/or a dynamic focusing optic, as further described, infra.

Referring now to FIG. 7C, a second case of an illumination optic and/or a group of illumination optics of the photon transport system 120 used to illuminate an illumination zone relative to a corner of the two-dimensional detector array 134 is illustrated. As with the first side illumination case, individual elements, sub-groups, and/or groups of detector elements observe at differing radial distances from the illumination zone where the differing radial distances have corresponding average observed tissue pathlengths, depths of penetration, and/or sampled regions of skin of the subject 170. Here, three groups or detection zones are illustrated. The first group 710 is illustrated as detection elements 1, 2, 3, 4, 5, and 6, where the commonality is a short radial distance between the illumination zone and the detection zone, such as used for the combination band spectral region and/or for small mean depths of penetration of the photons into the tissue of the subject 170. The second group 720 is illustrated with long rising dashes, where the commonality is a medium radial distance between the illumination zone and the detection zone, such as used for the first overtone spectral region. The third group 730 is illustrated with short falling dashes, where the commonality is a long radial distance between the illumination zone and the detection zone, such as used for the second overtone spectral region. As described, supra, any detector element, sub-group, and/or group is optionally associated with an individual filter, an individual optic, an individual dynamic optic, and/or a group of optics. Further, any detector element, sub-group, and/or group is optionally associated with any position and/or wavelength of illuminators, such as with a light-illuminating diode illumination array.

Referring now to FIG. 7D, a third case of an illumination optic and/or a group of illumination optics of the photon transport system 120 used to illuminate an illumination zone within a section within the two-dimensional detector array 134 is illustrated. As with the first side illumination case and the second corner illumination case, individual elements, sub-groups, and/or groups of detector elements observe at differing radial distances from the illumination zone where the differing radial distances have corresponding average observed tissue pathlengths, depths of penetration, and/or sampled regions of skin of the subject 170. Here, two groups or detection zones are illustrated. The third group 740 is a first section, arc, quadrant, zone, ring, square, rectangle, and/or polygon of detection elements at a first range of distances from the illumination zone, illustrated here with detector elements intersecting with a long-dashed/square shape. The fourth group 750 is a second section, arc, quadrant, zone, ring, square, rectangle, and/or polygon of detection elements at a second range of distances from the illumination zone, shown here with detector elements intersecting with a short-dashed/square shape. The fourth group 740 and fifth group 750 are illustrative of n groups where n is a positive integer of 2, 3, 4, 5, 10 or more where individual groups differ by 1, 2, 3, 4 or more cross-sectional distances of a detector element. As described, supra, any detector element, group, sub-group, and/or group is optionally associated with an individual filter, an individual optic, and/or an individual dynamic optic.

Still referring to FIG. 7D, in one optional filter arrangement, optical filters are stacked. For example, a first optical filter is a first long pass or a first short pass filter covering a wide range of first detector elements; a second optical filter is stacked relative to the first optical filter along the x-axis, which is the optical axis. The second optical filter is a second long pass, a second short pass, or a band pass filter covering a subset of the first detector elements. For example, the first optical filter is a long pass filter passing wavelengths longer than 1100 nm covering all of the fourth group 740 and fifth group 750, and the second optical filter is a long pass filter passing wavelength longer than 1450 nm covering all of the fifth group, which yields a first overtone filter for the fourth group 740 and a first and second overtone filter for the fifth group 750. Combinations of stacked filters for various groups include any of 2, 3, 4, or more filters described herein, such as the combination band filter, the first overtone band filter, the combination band/first overtone band filter, the second overtone band filter, the first overtone band/second overtone band filter, the sloping overtone bands filter, and the luminance filter described, supra, in the description of FIG. 7B. The inventor notes that cutting larger stackable filters reduces costs and more importantly light loss associated with placing individual filters over individual detector elements of the two-dimensional detector array 134.

Figure 7E:
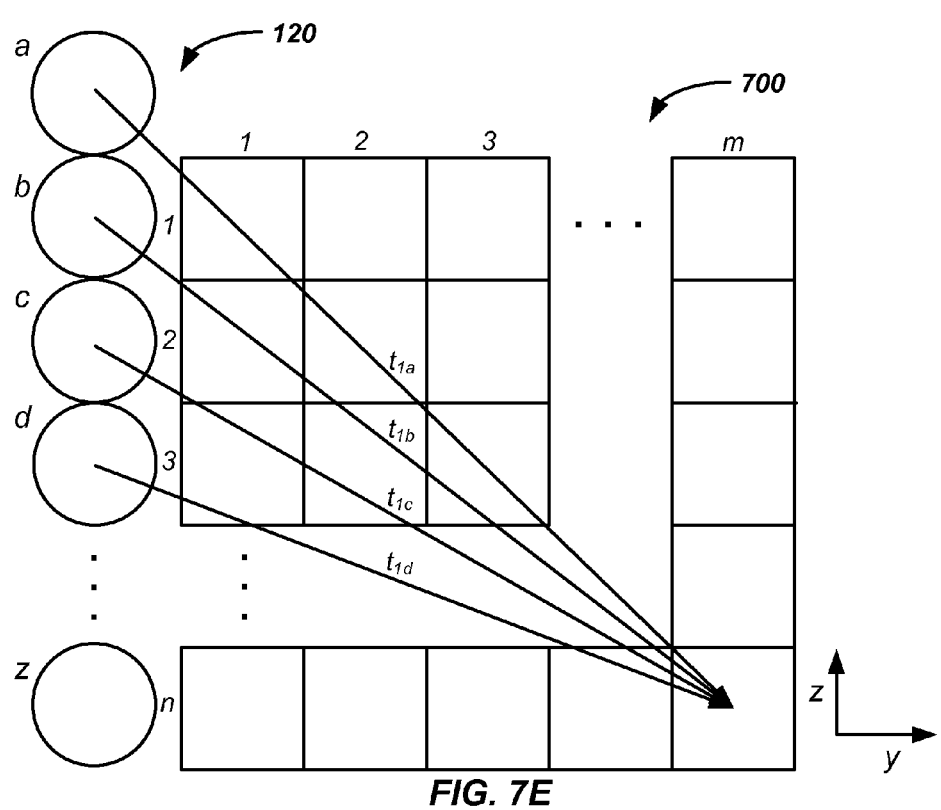

Referring now to FIG. 7E, a fourth example of multiple illumination zones from the photon transport system 120 positioned about and within, not illustrated, the two-dimensional detector array 134 is illustrated. In this fourth example, a matrix of illuminators, herein represented by a single column for clarity of presentation, are denoted as illuminators a-z. At a given point in time, any set or subset of the matrix of illuminators are used to deliver photons to the tissue of the subject 170. For example, at a first point in time, illuminators a-b are used; at a second point in time illuminators a-d are used; at a third point time illuminators d-g are used, and so on.

As illustrated, illuminators a-d are used and a detection element m,n is used. Generally, sets of illuminators are optionally used as a function of time where the illuminators define the number of photons delivered and provide a first part of a illumination zone-to-detection zone distance and selected detector elements as the same function of time define the second part of the illumination zone-to-detection zone distance. Optionally, the illumination array a light-emitting diode (LED) array used in combination with a filter array allowing an analyzer without use of a time-domain interferometer and/or a grating.

Referring again to FIGS. 7B-E, notably, detector elements associated with a first sub-group or first group at a first point in time are optionally associated with an $n^{th}$ sub-group or $n^{th}$ group at $n^{th}$ point in time when the same and/or a different set of illuminators are used, where n is a positive integer of 2, 3, 4, 5, 10 or more.

Multiple Two-Dimensional Detector Arrays

Referring now to FIGS. 8A-D, a multiple luminance/multiple detector array system 800 is described. Generally, one and preferably two or more illumination zones are provided by the photon transport system within and/or about two or more detector arrays, such as two or more of the two-dimensional detector arrays 134. For clarity of presentation and without loss of generality, several examples are provided, infra, of the multiple luminance/multiple detector array system 800.

Figure 8A:
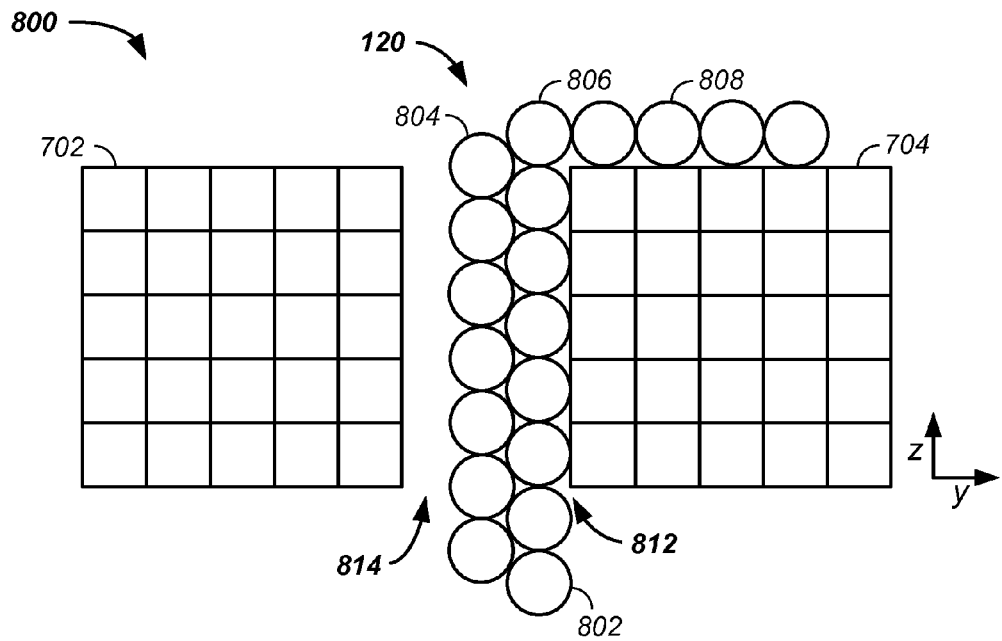
FIG. 8A and FIG. 8B illustrate a first example of a multiple two-dimensional detector array system and a second example of a multiple two-dimensional detector array system, respectively.

Referring now to FIG. 8A, a first example of the photon transport system 120 delivering light to the skin of the subject 170 at multiple illumination positions relative to two or more detector arrays, such as a first detector array 702 and a second detector array 704, is provided. In this first example, the photon transport system delivers light: (1) by the side 802, (2) removed from the side 804, (3) at the corner 806, and/or (4) around the corner 808 of a detector array, such as the second detector array 704. As illustrated, illumination zones are provided in a first column and in a second column relative to the side of the second detector. The first column 802 and the second column 804 of illuminators are illustrated proximately touching, with a first illuminator/detector gap 812, an edge of the second detector array 704 and with a second illuminator/detector gap 814 from the first detector array 702, where the first illuminator/detector gap 812 and the second illuminator/detector gap 814 are optionally different by greater than ten percent and are, respectively, less than and greater than, about 1, ½, ¼, ⅛, 1/16, or 1/32 of a millimeter.

Referring again to FIGS. 7(A-E) and 8A, any detector array is optionally tilted along the y- and/or z-axes to yield varying degrees of force applied to a sampled tissue sample as a function of detector position when directly contacting the tissue or indirectly contacting the tissue via a fronting detector layer during sampling. The varying pressure results in data comprising varying and/or controllable pressure for ease in subsequent data processing, such as via binning, grouping, correlations, and/or differential measures.

Still referring to FIGS. 7(A-E) and 8A, any detector array is optionally differentially cooled along the y- and/or z-axes, such as with a Peltier cooler on one side of the detector array, to yield varying degrees of temperature as a function of detector position when directly contacting the tissue or indirectly contacting the tissue via a fronting detector layer during sampling. The varying temperature results in data comprising varying and/or controllable temperature for ease in subsequent data processing, such as via binning, grouping, correlations, and/or differential measures, such as for analysis of temperature sensitive absorbance bands and/or water absorbance bands.

Multiple Pathlengths

Figure 8B:
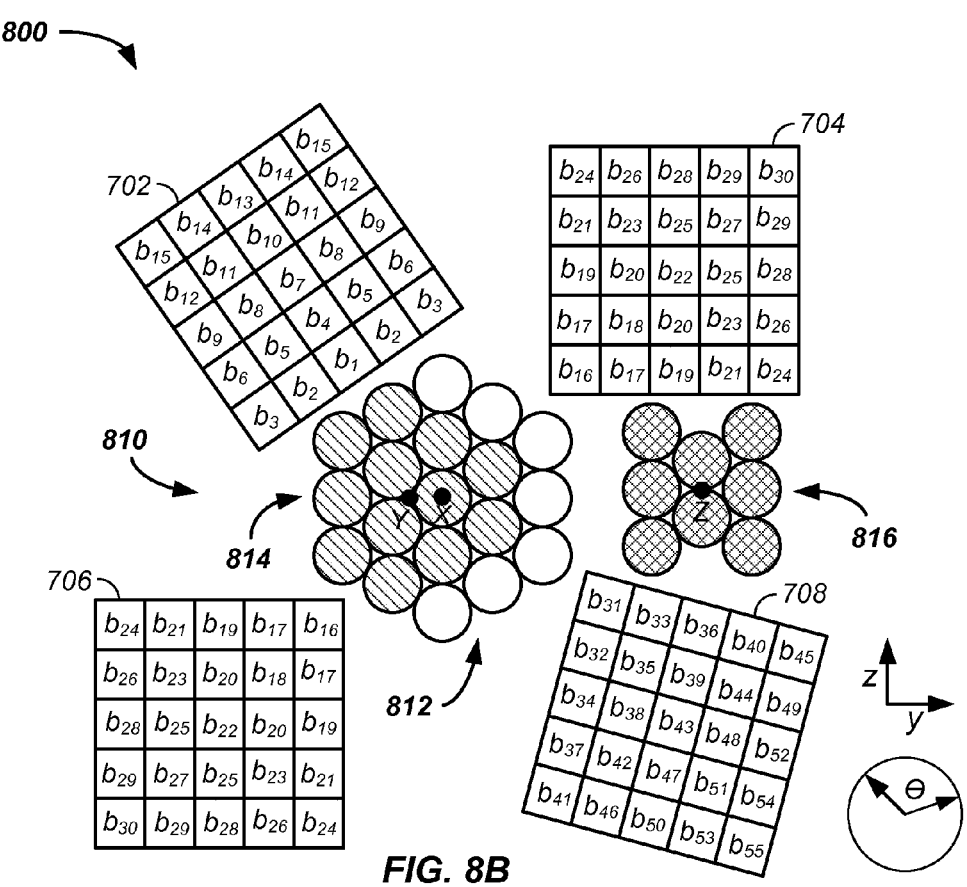

Referring now to FIG. 8B, a second example of the photon transport system 120 delivering light to the skin of the subject 170 at multiple illumination positions relative to two or more detector arrays is provided.

Illuminator Arrays

In this example, an illuminator array 810 is illustrated. Generally, the illuminator array 810 is a set of illumination points and/or an illumination area of any geometric cross-sectional shape along the y-, z-axes. Referring still to FIG. 8B, three examples of illuminator arrays 810 are illustrated: a first illuminator array 812 comprising an about circular illumination pattern, here represented as nineteen illumination areas and/or a rough circle of illumination; a second illuminator array 814, here represented as twelve illumination regions and/or a subset of the first illuminator array 812; and a third illuminator array 816, which represents an about square and/or rectangular illumination array, which does not overlap any of the first illuminator array 812. Additionally, a fourth illuminator array optionally overlaps a portion of any other illuminator array as a function of time, not illustrated.

Detector Arrays

Still referring to FIG. 8B, an illustrative example of a three illuminator area system coupled to a four area detection system is described, where the four area detection system comprises: a first detector array 702, a second detector array 704, a third detector array 706, and a fourth detector array 708. In this second example, four detector arrays are illustrated about the three illumination arrays 812, 814, 816, which are representative of any number of illumination elements and/or any number of illumination arrays. For ease of presentation, this section refers to a center mean illumination point for each of the three illumination arrays 812, 814, 816, which in the present case is the center of the symmetrically illustrated light illumination arrays labeled X, Y, and Z, respectively.

Still referring to FIG. 8B and now referring to the first detector array 702 and the first illumination array 812 having center X, the inventor notes that the first row of the detector array contains detector elements at three optical pathlengths from the center of the illumination array. A first pathlength, $b_1$, is observed at the center element of the first row of detector elements. A second pathlength, $b_2$, is observed with each of the detector elements, in the first row of the detector array, adjacent the center detector element in the first row of the first detector array 702. Data collected at the redundant pathlengths comprise multiple uses, such as precision determination, outlier detection, tissue variation estimation, and/or tissue mapping, as described infra. A third pathlength, $b_3$, is observed with each of the detector elements at the outer ends of the first row of the first detector array 702. Similarly, the second row of the detector array observes three additional pathlengths, described here as the fourth, fifth, and sixth pathlengths, $b_4$, $b_5$, $b_6$. Similarly, the third, fourth, and fifth rows of the detector array contains fifteen additional detector elements observing an additional three pathlengths per row or nine additional pathlengths, $b_7$-$b_{15}$. The inventor notes that the first detector array 702, represented as a 5×5 matrix of detector elements, is optionally an m×n array of detector elements, as described in relation to FIG. 6A, with a corresponding number of observed mean optical pathlengths and mean optical depths.

Still referring to FIG. 8B, as described, supra, in relation to FIG. 5 and further described, infra, as the median pathlength of the probing photons increases, the depth of penetration of the mean photon increases for each wavelength in the range of 1100 to 2500 nm until an absorbance limit of detection is reached. Thus, as illustrated, the first detector array 702 is configured to observe fifteen pathlengths, three per row, where ten of the pathlengths are observed twice with intentionally separated sample tissue volumes.

Still referring to FIG. 8B and referring now to the second detector array 704 and still referring to the first illuminator array 812, the second detector array 704 is rotated about the x-axis relative to the first detector array 702 placing a corner of the second detector array closet to the mean illumination point of the first illumination array, X, as opposed to the first detector array 702 having a side closest to the mean illumination point, X. Rotation of the second detector array 704 allows another set of observed pathlengths, even when a duplicate detector array design is used. For example, as illustrated the corner of the second detector array 704 represents a sixteenth pathlength, $b_{16}$. Similarly, the second diagonal of the second detector array 704 contains two additional detector elements observing a seventeenth pathlength, $b_{17}$, in duplicate due to symmetry about a line through the center of the first illuminator array 812 and nearest corner of the second detector array 704. Similarly, the third to ninth diagonal of the second detector array 704 contain twenty-two additional detector elements observing thirteen additional pathlengths, $b_{18}$-$b_{30}$.

Still referring to FIG. 8B and referring now to the third detector array 706 and still referring to the first illuminator array 812, the third detector array 706 is positioned opposite the second detector array 704. The symmetrical positioning of the third detector array 704 relative to the second detector array 704 and the first illuminator array 812 yields pathlengths mirroring those observed using the second detector array; particularly, pathlengths sixteen to thirty, $b_{16}$-$b_{30}$. The mirrored pathlengths allows repetitive data for an internal check of results, validation of results, outlier detection, concentration estimation bounding, and/or additional algorithmic uses. Notably, by merely shifting a detector array and/or a source array along the y-z-axes, instead of repeated pathlengths, the new illuminator/detector combination will observe new pathlengths; twenty-five new pathlengths for the illustrated 5×5 detector element array.

Still referring to FIG. 8B and referring now to the fourth detector array 708 and still referring to the first illuminator array 812, the fourth detector array 708 is rotated an angle theta relative to the first detector array 702. The rotation of the fourth detector array 708 breaks symmetry along a line from the center of the first illuminator array 812, X, and a center of the fourth detector array 708. Now, intentionally, lacking rotational symmetry the fourth 5×5 detector array observes twenty-five additional pathlengths, $b_{31}$-$b_{55}$, compared with the fifteen pathlengths observed by the first detector array 702 and fifteen distinct pathlengths observed using the second detector array 704.

Still referring to FIG. 8B and now referring to the second illuminator array 814, the center of the second illuminator array 814, Y, is offset along the y-z-axes relative to the center of the first illuminator array, X, which breaks symmetry relative to each of the four detector arrays 702, 704, 706, 708. The intentional breaking of the symmetry allows the four detector arrays 702, 704, 706, 708 to observe one hundred (25×4) new pathlengths by merely changing an optical illumination configuration. Similarly, now referring to the third illuminator array 816, moving the center of illumination to a third point, Z, yields an additional one hundred new observed pathlengths (25×4). To illustrate the number of observed pathlengths still further, use of four 50×50 detector arrays without symmetry relative to five illumination patterns yields 50,000 (2500 detectors/array×4 arrays×5 illumination zones) observed pathlengths. Detector arrays of m×n dimension where m and/or n are independently any positive integer of 1, 2, 3, 5, 10, 100, 500, 100 or more thus yields tens, hundreds, thousands, and/or millions of detector elements. Hence, with a two-dimensional detector array, even using one detector design, and an illumination source, even statically positioned, may readily yield hundreds of thousands or millions of observed pathlengths in a period of less than 1, 2, 3, 4, 5, 10, 20, or 30 seconds as the detectors are optionally used in parallel.

Filters

Herein, optical filters optically coupled with elements of the detector arrays are described.

Longpass Filters

Figure 9A:
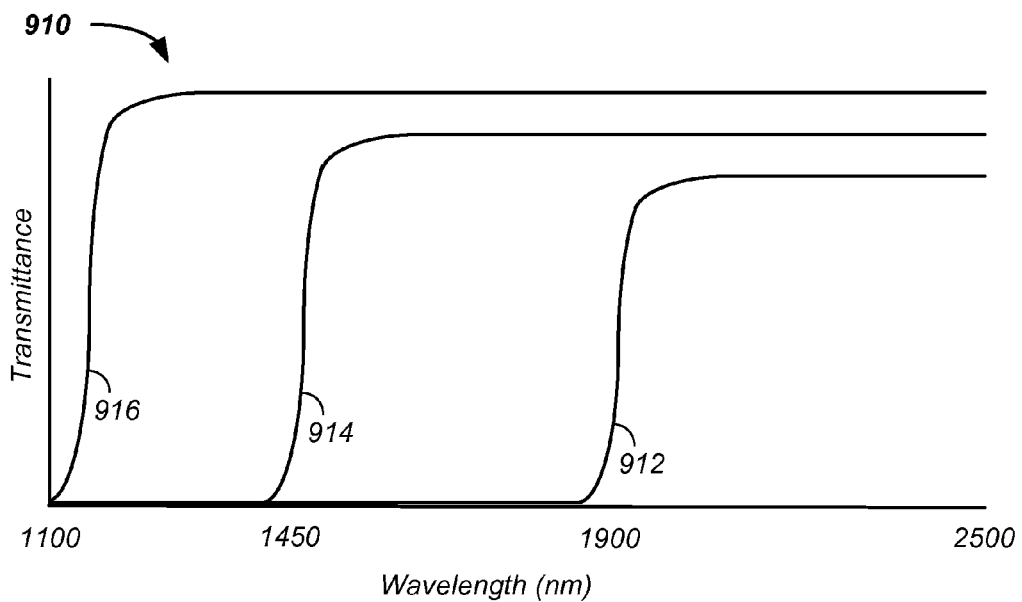
FIG. 9A illustrates transmission spectra of longpass optical filters and FIG. 9B relates longpass filters to water absorbance.

Referring now to FIG. 9A, a series of longpass filters are described. A longpass filter is an optical interference and/or coloured glass filter that attenuates and/or blocks shorter wavelengths and transmits and/or passes longer wavelengths over a range of wavelengths. Longpass filters optionally have a high slope described by a cut-on wavelength at a wavelength passing fifty percent of peak transmission. Herein, longpass filters refer to filters comprising a fifty percent cut-on wavelength in the range of 900 to 2300 nm. More preferably, for analysis of tissue spectra, the inventor has determined that longpass filters complementing water absorbance bands offer multiple advantages relating to detector dynamic range.

Figure 9B:
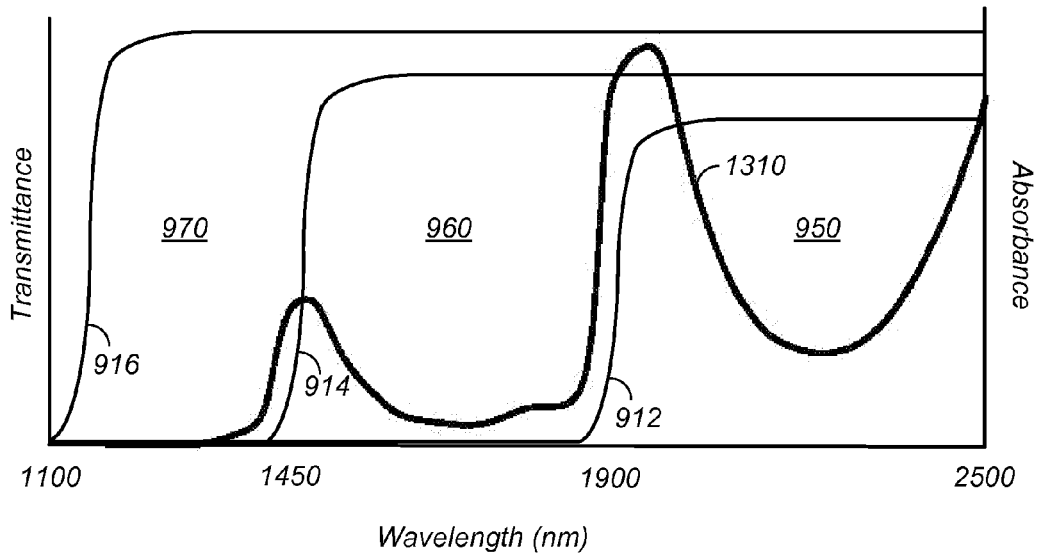

Referring still to FIG. 9A and referring now to FIG. 9B, a first longpass filter 912 is illustrated comprising a fifty percent cut-on wavelength in the range of 1850 to 2050 nm, such as at about 1900, 1950, or 2000 nm. The first longpass filter 912 is designed to transmit photons in a region referred to herein as a 'combination band region' 950, which comprises a first region of low water absorbance and three glucose absorbance bands. The inventor has determined that by having the sharp, often temperature sensitive and/or difficult to analyze region due to rapid changes in transmittance as a function of wavelength, cut-on wavelength in the wavelength range of the large water absorbance band spectral feature, that the filter weaknesses are masked by the water absorbance band while the filter strengths are optimize, as described herein. First, the first longpass filter 912 transmits a high percentage of light, such as greater than 70, 80, or 90 percent, in the desirable range of 2100 to 2350 nm where water absorbance 1310 and scattering combine to yield detected photons in the glucose rich dermis layer of skin and where glucose has three prominent absorbance bands at 2150, 2272, and 2350 nm. Second, the first longpass filter 912 has a transition cut-on range, that hinders analysis due to the rapid change in transmittance as a function of wavelength and is susceptible to temperature induced spectral shifts, that is placed in a region where water absorbance prevents detection of photons penetrating into the dermis, thereby eliminating the problem. Third, the first longpass filter 912 has a blocking range from a detector cut-on of about 700 nm to about 1900 nm, which blocks photons otherwise filling a dynamic range of an element of the detector array, which allows an enhanced signal-to-noise ratio, using proper detector gain electronics and/or integration time, in the desirable range of 2100 to 2350 nm. The inventor notes that the water absorbance band at circa 2500 nm functions as a natural shortpass filter, which combines with the first longpass filter 912 to form a combination band bandpass filter.

Referring still to FIG. 9A and FIG. 9B, a second longpass filter 914 is illustrated comprising a fifty percent cut-on wavelength in the range of 1350 to 1490 nm, such as at about 1375, 1400, 1425, 1450, or 1475 nm. The second longpass filter 914 is designed to transmit photons in a region referred to herein as a 'first overtone region' 960, which comprises a second region of low water absorbance and three glucose absorbance bands. As with the first longpass filter 912, the second longpass filter 914 is designed to function in a complementary manner with water absorbance of tissue. Particularly, the second longpass filter 914 transmits three prominent glucose bands in the first overtone region centered at circa 1640, 1692, and 1730 nm, which are in a region where the dominant absorber water and tissue scattering combine to yield detectable photons having sampled the glucose rich dermal layer of tissue in diffuse reflectance mode. Further, the second longpass filter blocks/substantially blocks light from about 700, 800, 900, 1000, and/or 1100 to 1450 nm, which would otherwise contribute to filling a dynamic range of a detector array element. Blocking the second overtone light, described infra, thus allows full use of a dynamic range of a detector in the first overtone region and a correlated enhancement in a signal-to-noise ratio of the three first overtone glucose absorbance bands. Still further, the second longpass filter 914 benefits from the water absorbance band at 1950 nm, which functions as a natural shortpass filter to the second longpass filter 914 forming a first overtone bandpass filter from about 1450 to 2000 nm or a spectral region therein.

The inventor notes that traditional spectroscopic analysis of tissue using near-infrared light does not: (1) combine light from the combination band region 950 with light from the first overtone region 960 using separate detectors, which are optionally individually optimized for a spectral region, or (2) use separate longpass filters, bandpass filters, or optics coupled to the multiple detectors to simultaneously enhance spectral quality of the first overtone region and combination band region.

The inventor has determined that the three glucose absorbance bands in the combination band region are linked at an atomic/chemical energy level to the three glucose absorbance bands in the first overtone region. Hence, detection of signals from corresponding bands of the combination band region and first overtone region are optionally compared to enhance glucose concentration estimations.

Referring still to FIG. 9A and FIG. 9B, a third longpass filter 916 is illustrated comprising a fifty percent cut-on wavelength in the range of 700 to 1200 nm, such as at about 800, 900, 1000, or 1100 nm. The third longpass filter 916 is designed to transmit photons in a region referred to herein as a 'second overtone region' 970 from about 1000 or 1100 to 1400 nm. Similar to the first and second longpass filters 912, 914, the third longpass filter 916 is designed to optimize signal-to-noise ratios in the second overtone region, function with the use of water absorbance bands at 1450 and 1900 nm as natural shortpass filters, and to be used with detector array elements observing photons having sampled at least the dermis skin layer. It is noted that the first, second, and third longpass filters 912, 914, 916 are illustrated with differing maximum light throughput for clarity of presentation, but each optionally function as a longpass filter as described supra.

Shortpass Filters

Figure 10:
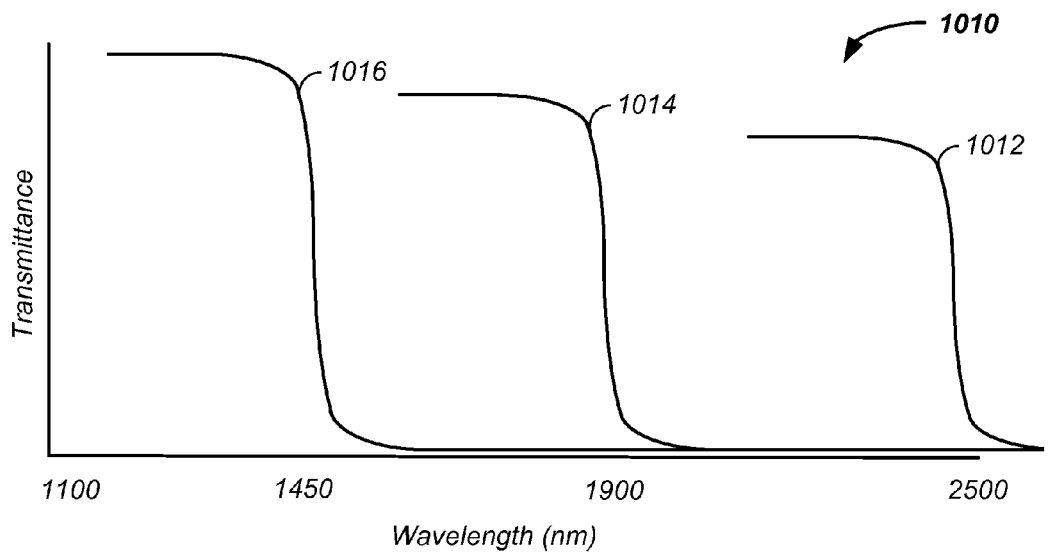
FIG. 10 illustrates shortpass filter transmission spectra.

Referring now to FIG. 10, a series of shortpass filters are illustrated. A shortpass filter is an optical interference and/or coloured glass filter that attenuates and/or blocks longer wavelengths of light and transmits and/or passes shorter wavelengths of light over a spectral range. Herein, shortpass filters refer to filters comprising a fifty percent cut-off wavelength in the range of 1400 to 3000 nm. More preferably, for analysis of tissue spectra, the inventor has determined that shortpass filters complementing water absorbance bands offer multiple advantages relating to detector dynamic range. A shortpass filter preferable passes greater than 60, 70, 80, or 90 percent of light in the passed spectral region and transmits less than 1, 5, 10, 20, 30, or 40 percent of the light in the attenuated spectral region.

Figure 11A:
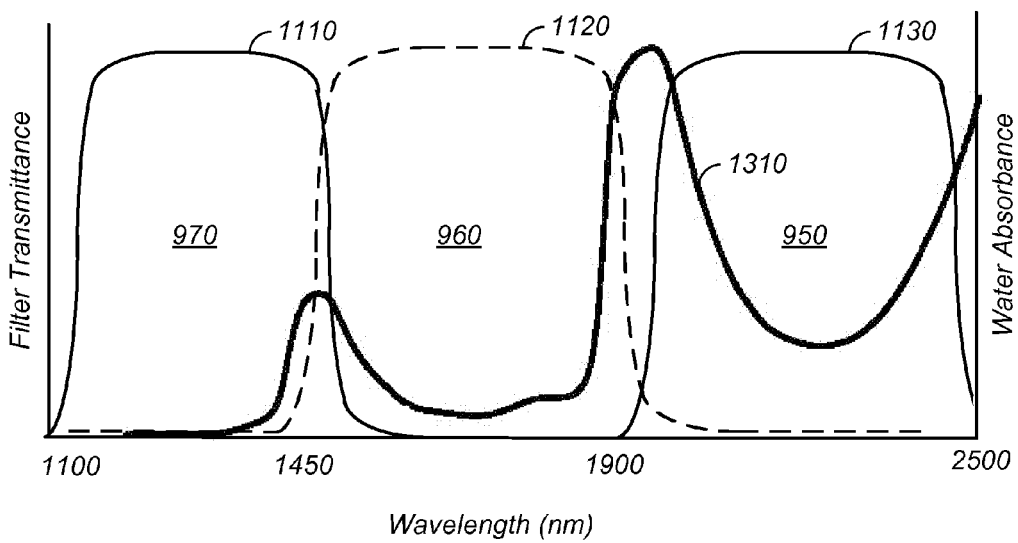
FIG. 11A illustrates bandpass filters relative to near-infrared spectral regions and FIG. 11B illustrates specialized bandpass filters.

Referring again to FIG. 10 and referring now to FIG. 11A, a first shortpass filter 1012 is illustrated comprising a fifty percent cut-off wavelength in the range of 2350 to 3000 or more nanometers. The first shortpass filter 1012 is designed to transmit photons in the second overtone 970, first overtone 960, and/or combination band region 950. The first shortpass filter 1012 is designed to block infrared heat at wavelengths greater than about 2350 nm, where otherwise transmitted heat would alter temperature of parts of the tissue and result in shifting of oxygen-hydrogen water band positions. Preferably, the first shortpass filter 1012 is combined with a longpass filter, such as with the first longpass filter 912 to form a combination band bandpass filter 1130 for the combination band region, with the second longpass filter 914 to form a bandpass filter for the first overtone/combination band spectral region, or with the third longpass filter 916 to form a second overtone/first overtone/combination band bandpass filter.

Referring again to FIG. 10 and FIG. 11A, a second shortpass filter 1014 is illustrated comprising a fifty percent cut-off wavelength in the range of 1800 to 2100 nm, such as at about 1900, 1950, or 2000 nanometers. The second shortpass filter 1014 is designed to transmit photons in the second overtone 970 and first overtone 960 regions. The second shortpass filter 1014 is designed to block infrared heat at wavelengths greater than about 2000 nm, where otherwise transmitted heat would alter temperature of parts of the tissue and result in shifting of oxygen-hydrogen water band absorbance positions of molecules in the skin. Preferably, the second shortpass filter 1014 is combined with a longpass filter, such as with the second longpass filter 914 to form a first overtone bandpass filter 1120 for the first overtone region or with the third longpass filter 916 to form a second overtone/first overtone bandpass filter.

Referring again to FIG. 10 and FIG. 11A, a third shortpass filter 1016 is illustrated comprising a fifty percent cut-off wavelength in the range of 1300 to 1600 nm, such as at about 1400, 1450, or 1500 nanometers. The third shortpass filter 1016 is designed to transmit photons in the second overtone 970 and optionally part of the first overtone 960 spectral regions. The third shortpass filter 1130 is designed to block photons from about 1600 to 2500 nm than would otherwise contribute to filling a detector well depth and/or dynamic range of a near-infrared detector, such as an indium/gallium/arsenide detector. Preferably, the third shortpass filter 1016 is combined with a longpass filter, such as with the third longpass filter 916, to form a second overtone bandpass filter 1110 for the second overtone region and/or a portion of the first overtone region, such as about 1500 to 1580 nm.

As illustrated in FIG. 11A, the fifty percent cut-off of the shortpass filter is preferably in a region of strong water absorbance to maximize transmitted photons while minimizing detection of out of band photons by using the water absorbance properties of skin.

Figure 11B:
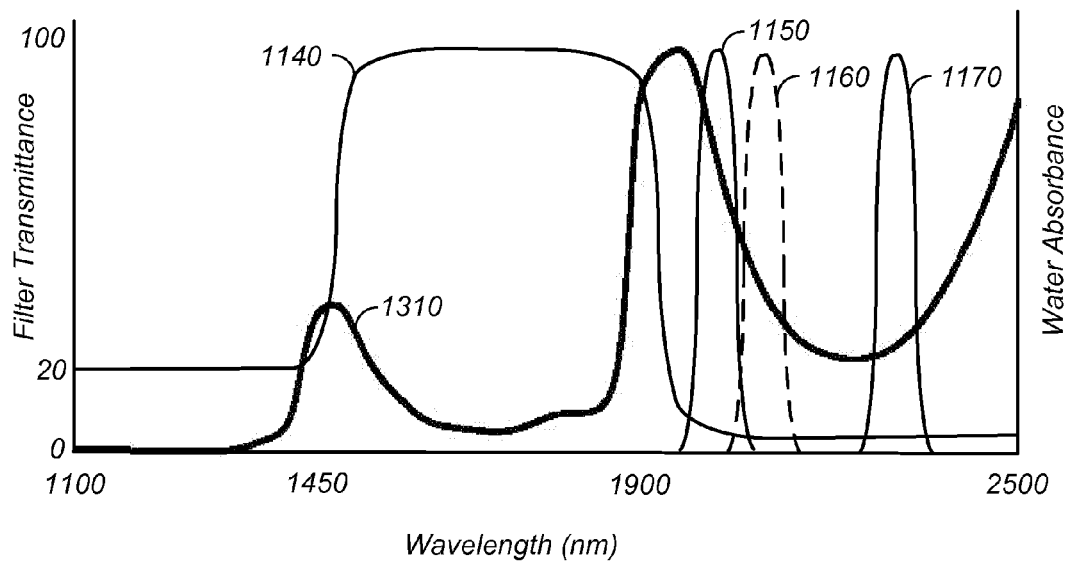

Referring now to FIG. 11B, narrowband bandpass filters or bandpass filters are optionally used to enhance the signal-to-noise ratio in a narrow spectral region, such as about 25, 50, 100, 150, or 200 nm wide. Optionally, the bandpass filters are associated with a light intensity limiting sample constituent, such as water. For example, in the combination band spectral region 950, a minimum water absorbance is observed at about 2270 with higher water absorbances observed at both longer and shorter wavelengths, such as at about 2150 or 2350 nm. Without an optical filter or an independent wavelength selection device, a multiplexed signal, such as obtained using a Fourier transform near-infrared spectrometer, will dominantly fill a well of a detector with photons from the spectral region transmitting more light, such as at about the water absorbance minimum, while obtaining fewer photons from spectral regions of higher absorbance. Thus, the signal-to-noise ratio in regions of higher water absorbance is degraded compared to use of the narrowband bandpass filter in a region of higher water absorbance and/or total observed absorbance. A narrowband bandpass filter or a set of narrowband bandpass filters in combination with multiple detectors, such as a two-dimensional detector array allows for each region to fully use a dynamic range of the detector elements, if properly matched with amplifier circuitry and integration time. For example, a first narrowband bandpass filter 1150 is optionally used at a first set of wavelengths correlated with a larger water absorbance. Similarly, a second narrowband bandpass filter 1160 and/or a third narrowband bandpass filter 1170 are optionally used at spectral regions of intermediate and low water absorbance, respectively. Generally, n narrowband bandpass filters are optionally used, where n is a positive integer of 2, 3, 4, 5, 6, 7, 8, 9, 10, 15, 20, 30, 50 or more. Combined, signals collected, preferably simultaneously, with the set of narrowband bandpass filters allows coverage of large regions of the near-infrared region where signal-to-noise ratios are significantly enhanced for given subsets of the near-infrared spectral region associated with each narrowband bandpass filter.

The narrowband filters are optionally used in combination with an array of LEDs, where LED wavelength regions are optionally radially configured relative to the associated filter in the filter arrays as a function of water absorbance. For instance, a first LED illuminating at a wavelength where water absorbance in skin is high is positioned close to one or more filters passing light emitted by the first LED, such as within about 0.2 to 0.75 millimeters. Similarly, a second LED illuminating at a wavelength where water in skin has medium absorbance is positioned at an intermediate distance from the one or more filters passing light emitted by the second LED, such as within about 0.5 and 1.5 millimeters. Similarly, a third LED illuminating at a wavelength where water in skin has low absorbance is positioned at a still further distance from the one or more filters passing light emitted by the third LED, such as within about 1.0 and 2.5 millimeters. Generally, the distance between an LED and a filter configuration passing light of the LED is a function of absorbance and/or scattering, such as according to equation 2, $$\text{distance} \sim \frac{1}{\text{abs}} * \frac{1}{\text{scattering}} \quad (\text{eq. 2})$$

where a correlation with the function is at least 0.4, 0.5, 0.6, 0.7, 0.8, or 0.9, where abs is absorbance of the sample at the given wavelength, such as approximated by water absorbance at the given wavelength, and scattering is the scattering coefficient and/or relative scattering coefficient at the given wavelength relative to neighboring wavelengths.

Figure 12:
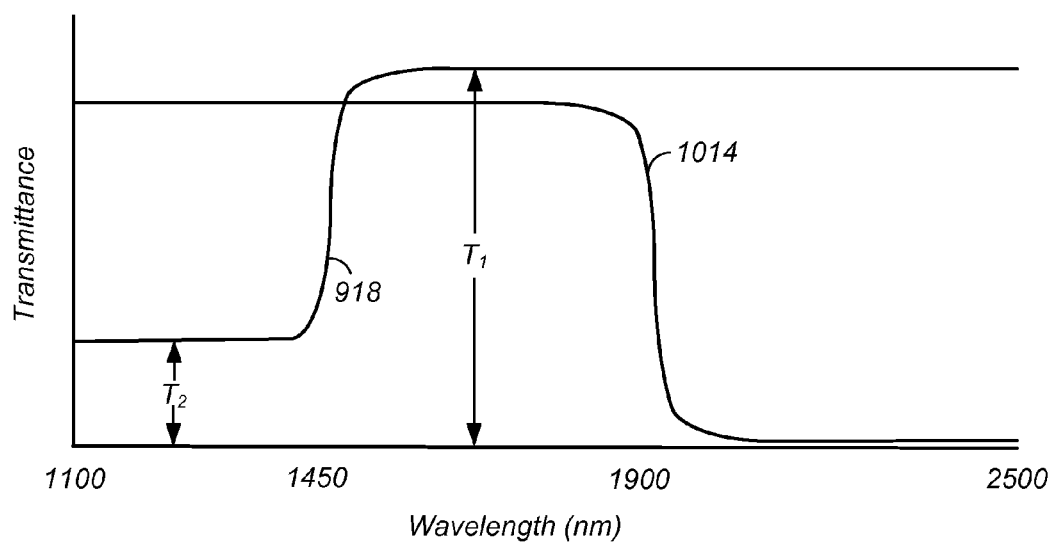
FIG. 12 illustrates elements of a bimodal optical filter.

Referring now to FIG. 12 and referring again to FIG. 11B, a step-function bandpass filters is described. In this example, a first step-function bandpass filter 1140 is illustrated with a large percent transmittance in the first overtone spectral region 960 and a lower transmittance, such as about 10, 20, 30, 40, or 50 percent transmittance, in the second overtone spectral regions 970. A major benefit of the first step-function bandpass filter 1140 is simultaneous collection of light from the first and second overtone spectral regions 960, 970, where the lower transmittance of the first overtone region 960, relative to the second overtone region 970, is compensated for by the greater transmittance in the first overtone region 960, relative to the second overtone region 970, of the first step-function bandpass filter and the difference in detectivity, D*, between the two regions. As illustrated in FIG. 12, the first step-function bandpass filter is optionally a combination of a shortpass and longpass filter, such as the second shortpass filter 1014 and a fourth longpass filter 918, where the fourth longpass filter 918 intentionally leaks light, such as less than 30, 20, 10, or 5 percent, at wavelengths shorter than about 1450 nm. Generally, the step-function bandpass filter has any transmittance profile. However, preferably, sections of 25, 50, 100, 200, or more nanometers of the step-function bandpass filter are anti-correlated with water absorbance, scattering, or a combination thereof, with a correlation coefficient of less than about −0.9, −0.8, −0.7, or −0.6.

Figure 13A:
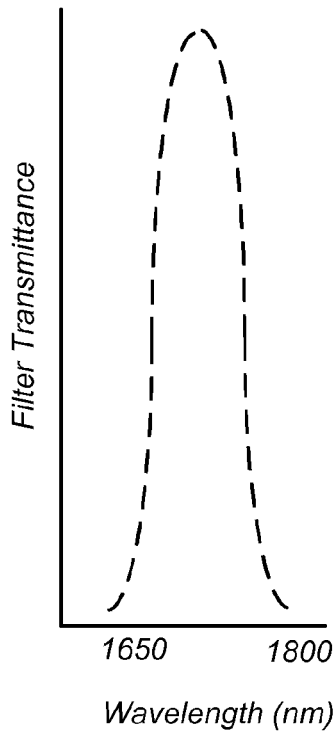
FIG. 13A and FIG. 13B illustrate a fat band filter and fat band absorbance, respectively.
Figure 13B:
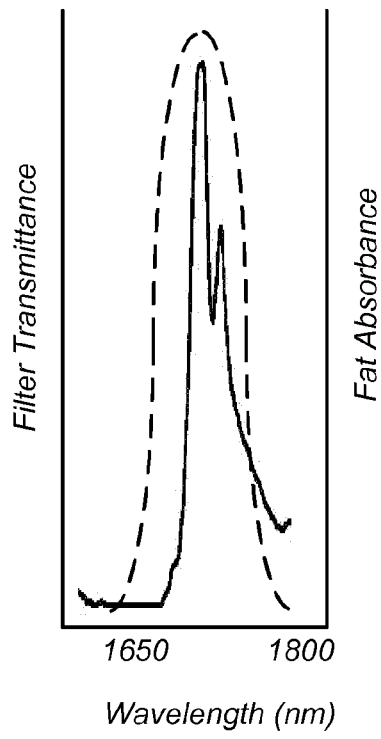
Figure 14A:
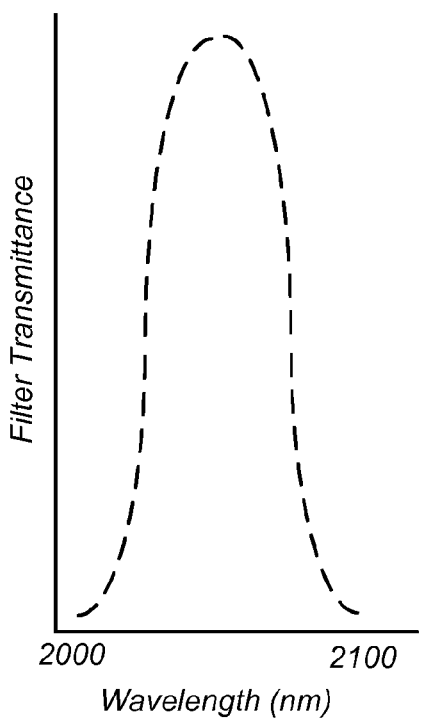
FIG. 14A and FIG. 14B illustrate a glucose filter and glucose absorbance, respectively.
Figure 14B:
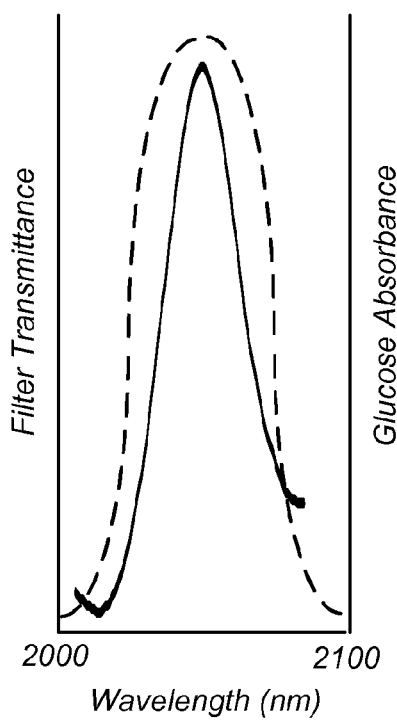

Referring now to FIGS. 13A, 13B, 14A, and 14B, narrowband filters are illustrated relative to absorbance features of blood and/or skin constituents. In FIG. 13A, a first analyte narrowband bandpass filter is illustrated; overlaid with fat absorbance bands in FIG. 13B. In FIG. 14A, a second analyte narrowband bandpass filter is illustrated; overlaid with a glucose absorbance bands in FIG. 14B. Generally, a set of n individual filters, where each filter passes wavelengths dominated by a limited number of sample constituents, are optionally used. Optionally and preferably the n individual filters are associated with individual detectors or groups of detectors of the two-dimensional detector array 134, as described infra. Notably, since the analyte narrowband filters, such as in FIGS. 13A, 13B, 14A, and 14B, occur at different wavelengths where the total absorbance, dominated by water absorbance and/or scattering, varies, preferably the detector array uses different gain settings and/or integration times for different detector elements, within the two-dimensional detector array 134, associated with different optical filters.

Detector Array/Filter Array Combinations

Figure 15:
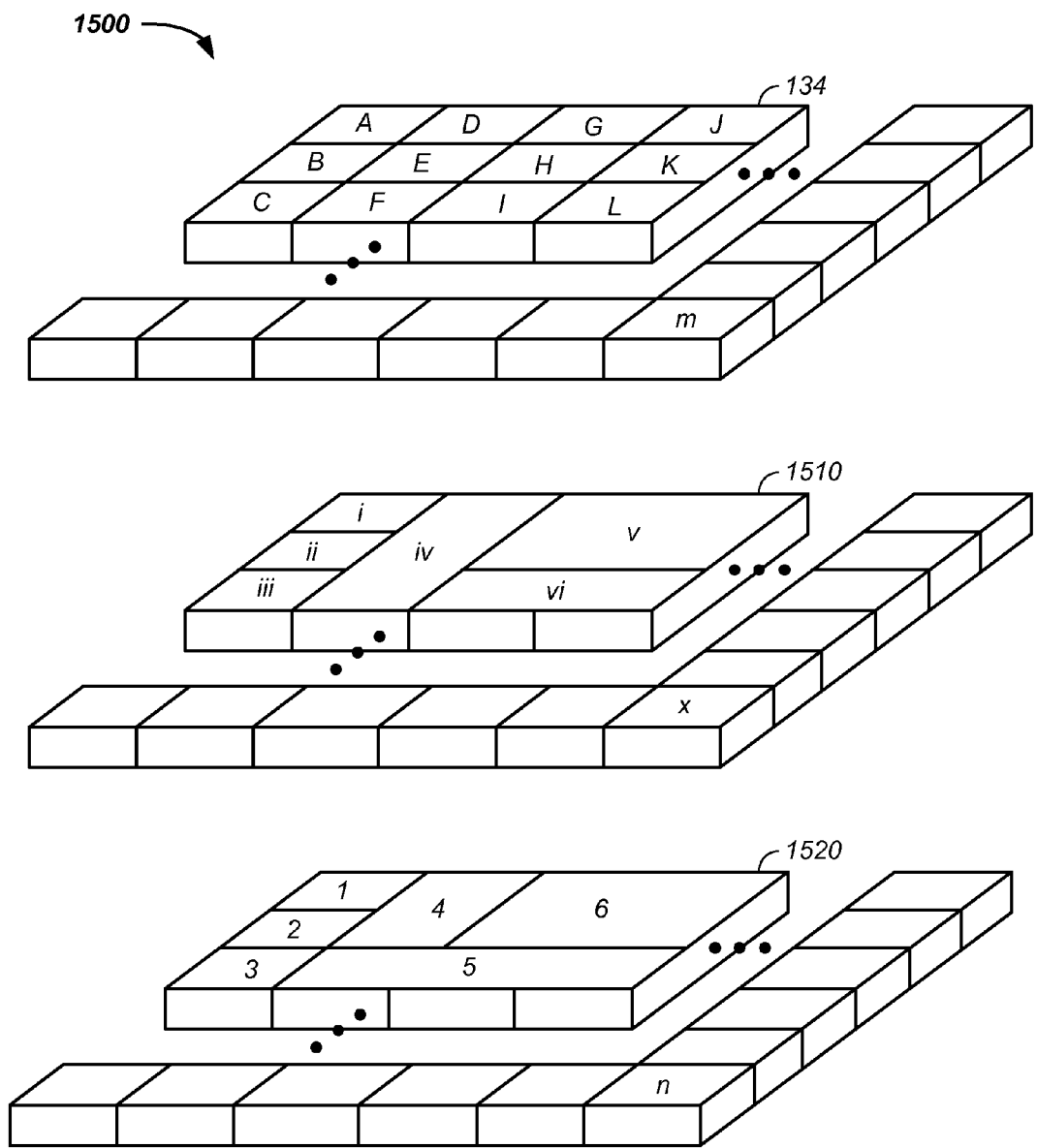
FIG. 15 illustrates a detector array with multiple filter array layers.

Referring now to FIG. 15, a detector array/filter array assembly 1500 is illustrated. For clarity of presentation and without limitation, the detector array/filter array assembly 1500 is illustrated and described as a single unit. However, optionally, the one or more two-dimensional filter arrays are optionally proximate the two-dimensional detector array 134, such as within less than 5, 2, 1, or 0.5 millimeters or are well removed from the two-dimensional detector array 134, such as at any position in the optical train between the source system 110 and the detector system 130. Further, for clarity of presentation and without limitation, two two-dimensional filter arrays are described, which are representative of 1, 2, 3, 4, 5, or more filter arrays. Still further, the two-dimensional filter arrays presented are optionally presented in reverse or any order in the optical train.

Still referring to FIG. 15, a first example of the detector array/filter array assembly 1500 is described, which is a form of the incident optic/two-dimensional array system 700. In this example, the two-dimensional detector array 134 is combined with 1, 2, 3, 4 or more two-dimensional optical filter arrays, such as a first optical filter array 1510 and a second optical filter array 1520. Several features of the detector array/filter array assembly 1500 are noted. First, optionally individual detector elements, A, B, C, optically align with individual filters of the first optical filter array 1510, i, ii, iii, and/or optically align with individual filters of the second optical filter array 1520, 1, 2, 3. Second, optionally two or more detector elements, D, E, F, optically align with a single filter element of the first optical filter array 1510, iv, which aligns with two or more elements of the second optical filter array 1520, 4, 5. Third, optionally, a single optical filter element of the first optical filter array 1510, iv, optically aligns with two or more elements of the second optical filter array 1520, 4, 5. Fourth, optionally, a single optical filter element of the second optical filter array 1520, 5, optically aligns with two or more elements of the first optical filter array 1520, iv, vi. Fifth, optionally columns and or rows of detector elements, (D, E, F), (F, I, L) align with a column optic, iv, or row optic, 5, respectively. Fifth, a single two-dimensional filter array, such as the first two-dimensional optical filter array 1510, optionally contains 2, 3, 4, 5, 10, 20, 50, or more filter types. Sixth, a single two-dimensional filter array, such as the first two-dimensional optical filter array 1510, optionally contains 2, 3, 4, 5, 10, 20, 50, or more filter shapes.

Figure 16:
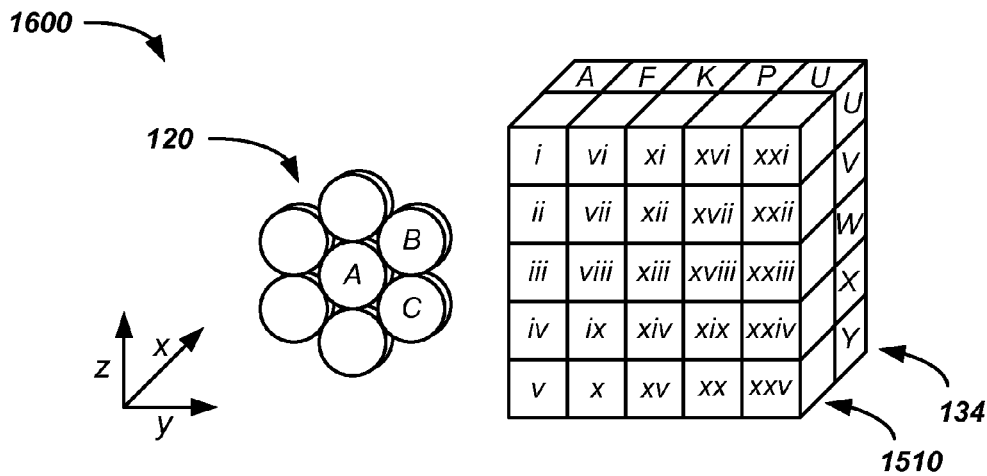
FIG. 16 illustrates a source array proximate a combined detector/filter array.

Referring now to FIG. 16, a multiple illumination zone/multiple detection zone system 1600 is illustrated. For example, an array of illumination points delivered from the photon transport system 120 is illustrated launching photons out of the page along the x-axis into the skin of the subject 170, not illustrated. An array of detection zones are achieved, monitoring photons moving into the page along the x-axis, using the two-dimensional detector array 134 and as illustrated the optional first optical filter array 1510. Similar to the systems described supra when referring to FIG. 8B, the illustrated illumination array optionally illuminates all illuminators; a single illuminator, such as element A, B, or C; and/or subsets of illuminators, such as elements A and B or A, B, and C. As described, supra, the optionally varying position of illumination coupled with the two-dimensional detector array 134 yields discrete pathlength and depth of penetration information about the optically sampled skin tissue of the subject 170 for each detector element of the two-dimensional detector array 134. As illustrated, the first two-dimensional optical filter array 1510 provides additional insight as to the sampled skin by selectively filtering: (1) regions, such as the combination band region 950, the first overtone region 960, and/or the second overtone region 970; (2) analytes, such as through use of the narrowband analyte filters; and/or (3) based on intensity of the observed signal, such as through narrowband filters designed for a narrow range of absorbances of the sample tissue, where detector gain elements and/or integration times are optionally individually configured for each element or group of elements, such as along a column or row, of the two-dimensional detector array 134.

Detector

Physical and tissue constraints limit a sample interface size between the analyzer 100 and subject 170. As such, minimizing use of non-optical parameters in the sample interface is beneficial. In one embodiment, a readout element of a CCD array is place on an outer perimeter of the sample interface area or outside of the perimeter. If two or more detector arrays are used, the readout elements of the detector arrays are optionally on opposite sides of the sample interface or on adjacent sides of the sample interface, such as at about ninety degrees from each other. Similarly, if three of more detector arrays are utilized, the readout positions of the multiple detector arrays optional circumferentially surround the sample interface area. Further, having multiple detector arrays allows a more rapid readout of the data as the readouts are optionally at least partially in parallel. Parallel readout of the gathered signal allows: (1) faster readout, (2) timing of readout corresponding to an expected signal-to-noise ratio, and/or (3) an ability to start calculations before all data is received, such as initiation of a tissue-specific tissue map and/or part of a rolling glucose concentration estimation. Still further, columns/rows of a traditional CCD array are optionally configured along arcs, chords, circles, and/or along an arc allowing detector elements to be positioned in concentric rings or other non-rectangular patterns. Still further, optionally the individual rows, columns, and/or curved sets of detector elements are optionally read out individually allowing an inner set, relative to an illuminator, where absorbance is smallest to be read out first and/or more often than outer detector sets, where larger absorbance of tissue leads to longer sample integration times.

Multiple Two-Dimensional Detector Arrays

Figure 17:
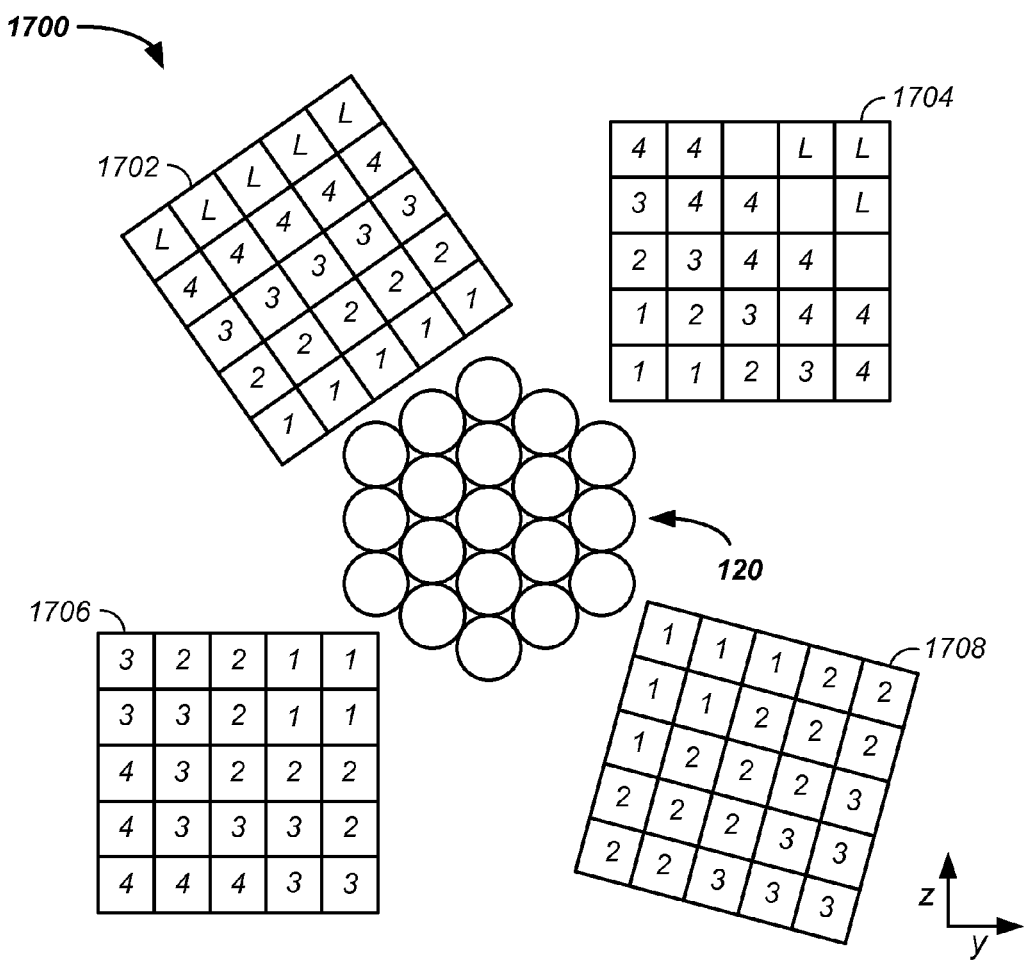
FIG. 17 illustrates a source relative to multiple two-dimensional detector arrays.

Referring now to FIG. 17, a multiple two-dimensional detector array system 1700 is illustrated. As illustrated, the photon transport system 120 delivers photons proximate a plurality of two-dimensional detector arrays denoted here as a first detector array 1702, a second detector array 1704, a third detector array 1706, and a fourth detector array 1708. Generally, any number of two-dimensional detector arrays are optionally used, such as 2, 3, 4, 5, 10, 20, or more detector arrays. Configurations of the detector arrays 1702, 1704, 1706, 1708 are described, infra.

Referring still to FIG. 17 and referring now to the first detector array 1702, the first detector array is optionally positioned with an edge of the first detector array 1702 proximate an outer border or edge of an illumination point, zone, or array of the photon transport system 120. In this example, first detector array 1702 is optically and/or physically coupled to a series of filters, such as: a first filter, 1, coupled to a first detector element row; a second filter, 2, coupled to a second detector row; a third filter, 3, coupled to a third detector row; a fourth filter, 4, coupled to a fourth detector row; and a fifth filter, L, coupled to a fifth detector row. Here the first, second, third, fourth, and fifth filter, 1, 2, 3, 4, L, are optionally a combination band filter, a first overtone filter, a first and second overtone filter, a second overtone filter, and luminance filter, respectively. Similarly, the first, second, third, fourth, and fifth filter, 1, 2, 3, 4, L, are optionally an analyte narrowband bandpass filter, a spectral region filter, a first overtone filter, a second narrowband analyte filter, and luminance filter, respectively. Generally, the individual filters are any optical filter. The individual filters optionally cover a column, row, geometric sector, and/or two-dimensional region of the two-dimensional detector array 134. Optionally, physical edges of the optical filters fall onto unused detector elements, such as a column, row, or line of filter elements.

Referring still to FIG. 17 and referring now to the second detector array 1704, additional detector/filter configurations are described. First, the second detector array 1704 is optionally positioned with a corner proximate the outer border or edge of an illumination point, zone, or array of the photon transport system 120. Rotation of the second detector array 1704 relative to the first detector array 1702 yields a second set of distinct pathlengths and correlated depths of penetration compared to those observed using the first detector array, as described supra. Second, the same filter elements, as used on the first detector array 1702, are optionally used on the second detector array 1704, which reduces manufacturing costs and research and development time understanding finer points, such as temperature stability of the filters. However, the physical mounting configuration of the filters are optionally different, which yields an additional set of measures of state of the subject 170. For example, the first filter, 1, as illustrated is positioned along two diagonals of the second detector array 1704, which yields three optical filter/detector combinations not observed with the first detector array 1702 where the three new combinations relate to three additional sampled pathlengths and depths of penetration of the subject 170. Similarly, the second, third, fourth, and fifth filters, 2, 3, 4, L, are positioned along diagonals across the second detector array 1704 yielding, as illustrated, eighteen additional measurements of the state of the subject 170. Further, in this example, one set of detector elements are not associated with a filter, which yields yet another set of measurements of the state of the subject 170.

Referring still to FIG. 17 and referring now to the third detector array 1706, additional detector/filter configurations are described. First, the first, second, third, and fourth filters, 1, 2, 3, 4, are orientated in yet another set of configurations relative to the photon transport system 120. Notably, in this example, some of the source/detector element distances are intentionally redundant yielding internal precision, outlier, sample inhomogeneity checks, and/or sample interface 150 contact checks. For example, three elements of the second and third detector array 1704, 1706 have redundant positions of the first filter, 1. In addition, one detector element of the third detector array 1706 uses the first filter, 1, in a position not used with the first or second detector arrays 1702, 1704 yielding yet another measure of the state of the subject 170. Similarly, the second filter, 2, is configured with both redundant positions, relative to those used with the second detector array 1704, and with new positions, relative to those used with the second detector array 1704. In this example, the third filter and fourth filter, 3, 4, are configured at larger distances from a mean point of the illumination zone relative to the filter positions configurations of the second detector array 1704. In practice, some of the third and fourth filter/detector positions are optimally probing the glucose containing dermal region 174, while others will yield information on the intervening and underlying epidermis and subcutaneous fat regions, respectively. Generally, the range of information gathered is used in post-processing to generate more accurate and precise analyte concentration information, such as through development and use of the same data used to form a person specific tissue map.

Referring still to FIG. 17 and referring now to the fourth detector array 1708, still additional detector/filter configurations are described. In this example, still further illumination zone to detection zone distances are illustrated for the first, second, and third filters, 1, 2, 3. As illustrated, the second and third filters, 2, 3, such as a first overtone and a second overtone filter, extend to still greater radial distances from the illumination zone yielding still yet another set of measures of the state of the subject 170. Further, in this example, the fourth detector array 1708 is rotated to a non-symmetric orientation relative to the illumination zone, which yields an entirely new set of pathlengths and depths of penetration, as described supra.

Referring still to FIG. 17, for clarity of presentation and without limitation a particular filter/detector combination of the first filter, 1, is described. Here the first filter, 1, is a combination band filter used for short distances between the illumination zone and detection zone. As described supra in the description of the first, second, third, and fourth detector arrays 1702, 1704, 1706, 1708 multiple short distances between the illumination zone and detection zone are probed, some of which will optimally probe the glucose containing dermal layer 174 of the subject 170, some of which will primarily probe the epidermis 173 of the subject 170, and some of which probe into the subcutaneous fat layer 176 of the subject 170. The availability of multiple measures of the state of the subject allows post-processing to derive information about the tissue layer thicknesses, tissue homogeneity, probed pathlengths, probed tissue depth, and/or analyte concentration of the subject 170 with optional use of redundant information, exclusion of outlier information, exclusion of non-optimally sampled tissue, and/or inclusion of optimally measured tissue. Similarly, use of the second, third, fourth, and fifth filter, 2, 3, 4, L, along with use of no filter at a variety of intelligently selected radial distances from the illumination zone based on scattering and absorbance properties of the tissue of the subject 170 yield additional complementary and optionally simultaneous information on the state of the subject 170.

Referring still to FIG. 17, for clarity and without loss of generalization another example of the photon transport system 120 delivering light to the skin of the subject 170 at multiple illumination positions relative to two or more detector arrays is provided. In this example, the first detector array 1702 is illustrated with a plurality of filters along rows of detector elements. For example, a first filter, illustrated as filter 1, is optionally a combination band filter; a second filter, illustrated as filter 2, is optionally a first overtone filter; a third filter, illustrated as filter 3, is optionally a first and second overtone filter; a fourth filter, illustrated as filter 4, is optionally a second overtone filter; and a fifth filter, illustrated as filter L, is optionally a luminance filter/intensity filter. The inventor notes that the filters are arranged in readily manufactured rows, provide a spread of radial distances within a row, and fall in an order of wavelength inversely correlating with mean pathlength as a function of radial distance from the illuminator. Referring now to the second detector array 1704, the third detector array 1706, and the fourth detector array 1708 positioned about the illumination zone from the photon transport system 120, the inventor notes that the same five filters positioned in different configurations and/or orders as a function of radial distance from the illumination zone and/or as a function of rotation angle of the detector array yield a plurality of additional pathlengths. For brevity and clarity of presentation, only the first filter, filter 1, is addressed. In the first detector array 1702, the first filter represents three distinct mean pathlengths from a mean illumination zone using the $1^{st}$ and $5^{th}$ detector elements, the $2^{nd}$ and $4^{th}$ detector elements, and the $3^{rd}$ detector element. Similarly, the second detector array filter 1704 monitors two additional mean pathlengths from the mean illumination zone using the first filter and individual detector elements. The third detector array 1706 could measure the same mean pathlengths as the second detector array 1704; however, preferably the third detector array 1706 measures still two more mean pathlengths using two pairs of detector elements with differing distances from the mean illumination zone. Similarly, the fourth detector array 1708 optionally measures a number of yet still further distinct mean pathlengths, such as by binning all six detector elements, or by binning rows of detector elements. Thus, at a first point in time, the four detector arrays 1702, 1704, 1706, 1708 optionally monitor at least eight mean pathlengths using only the first filter. At a second point in time, an additional distinct eight pathlengths are optionally monitored by illuminating a second pattern of the illustrated illumination points. The inventor notes that even illuminating all of the illumination points or only the first and second rings of illumination points, despite having the same mean point of illumination, will yield eight additional mean pathlengths in the tissue due to tissue inhomogeneity. Clearly, simultaneous use of the other four filters allows for simultaneous collections of spectra having at least forty pathlengths (8×5). Further, filter 1, is optionally different, in terms of a filter parameter such as a cut-on wavelength or a cut-off wavelength, for each detector array 1702, 1704, 1706, 1708 without complicating manufacturing, which yields still additional simultaneously probed optical tissue pathlengths. Generally, any number or detector elements, any number of detector arrays, any number of filters, and/or any geometry of filter layout are optionally used to obtain a desired number of simultaneously probed sample pathlengths. Optionally, signal from groups of common detector elements are binned to enhance a given signal-to-noise ratio.

Further, the two-dimensional detector arrays described herein optionally contain 1, 2, 3, or more detector materials 134 and/or types. For example, a single two-dimensional detector array 134 optionally contains 1.7, 1.9, 2.2, and/or 2.6 µm indium/gallium/arsenide detectors. For example, the 2.6 micrometer indium/gallium/arsenide detector is optionally optically coupled with longpass, shortpass and/or bandpass filters for the combination band 950 spectral region and/or the 1.7, 1.9, 2.2 µm indium/gallium/arsenide detectors are optionally coupled with longpass, shortpass, and/or bandpass filters for the first overtone region 960. Optionally and preferably, different detector types are joined along a joint and/or a seal, where the seal optionally corresponds with a joint or seal between two filter types or simply a set, such as a column, of unused detector elements.

Figure 18A:
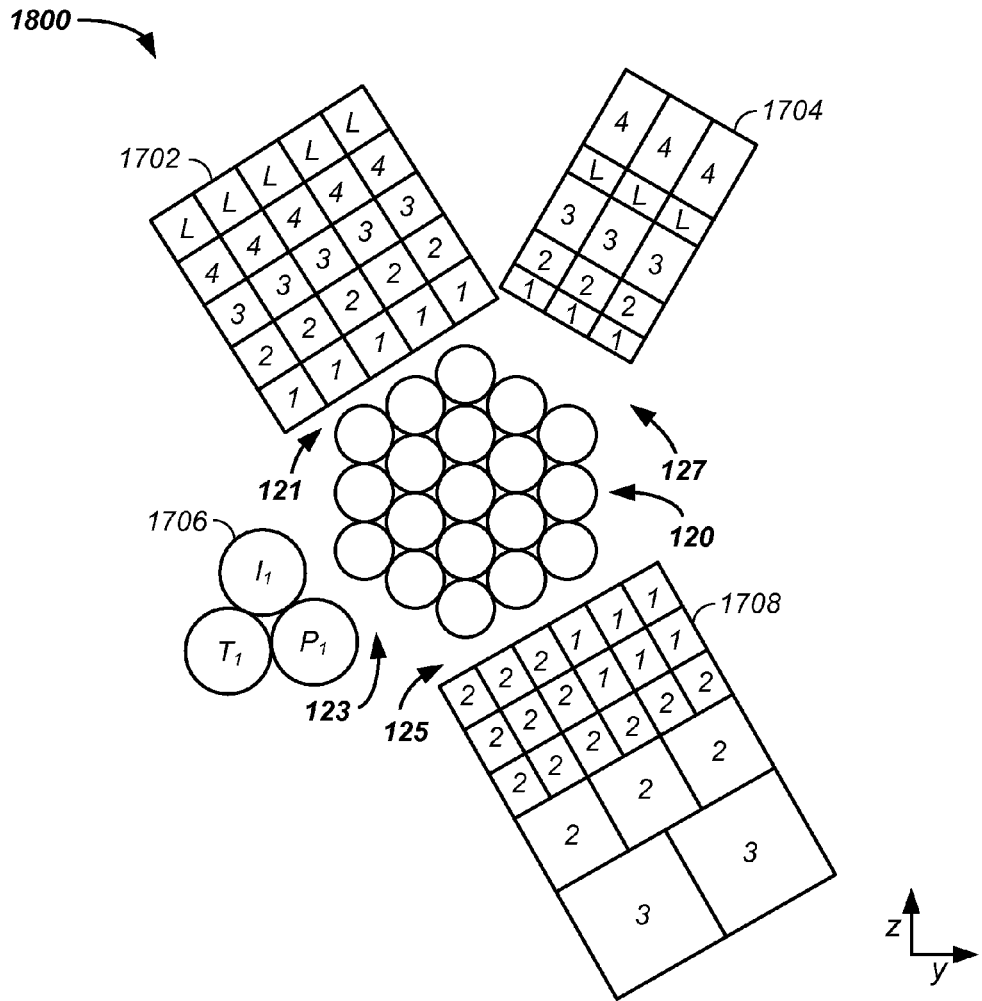
FIG. 18A and FIG. 18B illustrate an illumination array relative to multiple two-dimensional detector array types and rotated two-dimensional detector arrays, respectively.

Referring now to FIG. 18A, a multiple detector array system 1800 is described, which is a further example of a multiple two-dimensional detector array system. In this example, multiple detector types are optionally used, as described infra. Further, in this example, multiple detector sizes are optionally used, as described infra.

Referring still to FIG. 18A, additional examples of two-dimensional detector/filter arrays are provided. Referring now to the first detector array 1702 and the second detector array 1704, the second detector array 1704 relative to the first detector array illustrates:

that two detector arrays optionally vary in length and/or width by at least 5, 10, or 20 percent, which results in an ability to miniaturize a sample probe head and/or to enhance collection efficiency of delivered photons by increasing overall skin surface coverage by the detectors; and that the row and/or columns of detector elements optionally have different single element sizes, which allows control over range of pathlengths monitored with a given detector element.

Referring now to the third detector array 1706, the two-dimensional detector array 134 optionally contains sensors and/or optics to measure a range of parameters, such as a local tissue temperature, $T_1$, a local tissue pressure, $P_1$, and/or a local illumination, $I_1$. Referring now to the fourth detector array 1708, the two-dimensional detector array 134 is optionally designed to be read out in columns or sideways as rows, which allows each row to have a different detector element size. Increasing the detector element size as a function of radial distance away from an illuminator allows an enhanced/tuned signal-to-noise ratio as the detector aperture is larger as the number of photons exiting the skin with increased radial distance decreases. The larger aperture sizes of the detectors enhances signal-to-noise ratios as baseline noise remains constant and thermal noise increases at a smaller, less than linear, rate compared to the linear increase in signal with increased integration time. Referring now to the first through fourth detector arrays 1702, 1704, 1706, 1708, an optional range of illuminator/detector gaps are illustrated 121, 123, 125, 127 for the first through fourth detector arrays 1702, 1704, 1706, 1708, respectively.

Figure 18B:
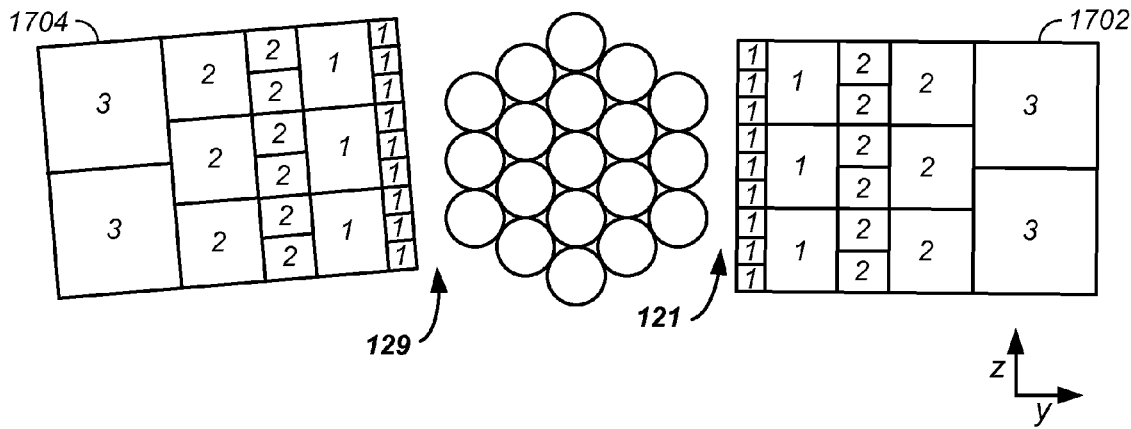

Referring now to FIG. 18B, yet another example of a multiple two-dimensional detector/filter array system is provided. In this example, a first detector array 1702 is configured with zones of regularly shaped filters over multiple individual detector element sizes. For example, the first filter, 1, such as a first overtone filter, covers two rows of detector elements, which aids in filter costs, alignment, masks, and/or installation. The first row of detector elements comprises smaller dimensions than the second row of detector elements, which enhances signal-to-noise ratios in each row as the time to fill detector wells in the first row of detector elements is less than the time to fill detector wells in the second row of detector elements due to the light transport/scattering properties in the 1450 to 1900 nm spectral region. The larger aperture of the second row detector elements gathers more light as a function of time compared to the first row detector elements as an area of a detector element in the second row is at least 2, 3, 4, 5, 6, 7, 8, 9, or 10 times larger than an area of a detector element in the first row. Similarly, the third and fourth rows of detector elements are optionally associated with the second optic, 2, such as the first overtone/second overtone band filter. The third row of detector elements are larger than the first row of detector elements due to fewer photons from an illumination zone exiting the skin at greater distances from the illumination zone and smaller than the second row of detector elements due to the enlarged spectral bandwidth of the first overtone/second overtone band filter. The fifth row of detector elements optionally uses a third, 3, filter, such as a second overtone filter. Generally, the area of detector elements is preferably manufactured to inversely match light density exiting the skin of the subject 170 in each optically filtered wavelength range. Here, the first detector array 1702 in this example is designed to optionally readout in rows, which allows different rows to comprise different sizes of detector elements. Optionally, filters at one or more detector elements positions are matched to wavelengths of an LED of a set of LEDs.

Referring still to FIG. 18B, a second detector array 1704 is presented in a rotated configuration about the x-axis relative to the first detector array 1702. The rotation of the second detector array 1704 yields a continuum of pathlength ranges for a row of detectors. For example, in the first detector array 1702, the first row of detectors monitor four average pathlengths of illuminated tissue due to C2 symmetry of the detector elements in the first row, where for example the inner two detector elements observe a single first mean pathlength and the outer two detector elements observe a single second mean pathlength. However, in stark contrast, the first row of detector elements in the second detector/filter array 1704 monitor eight different mean optical pathlengths of light delivered by the photon transport system 120. Similarly, each row of detector elements in the second detector array 1704 observe, simultaneously, more mean pathlengths of photons from the photon transport system 120 compared to a corresponding row of detector elements in the first detector array 1702 due to the rotation of the second detector array in the y,z-plane relative to a line from a center of the second detector array to a center of the illumination zone.

Detector Array/Guiding Optical Array Combinations

Figure 19A:
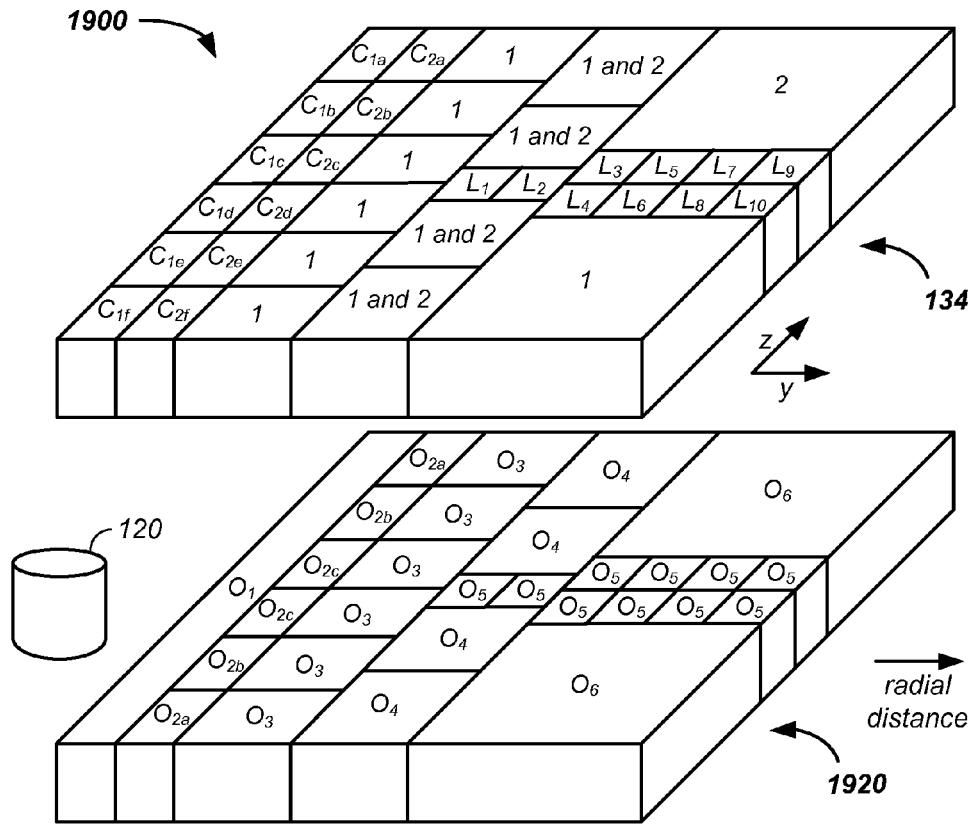
FIG. 19A and FIG. 19B illustrate a two-dimensional detector array relative to an optic array in an expanded and assembled view, respectively.
Figure 19B:
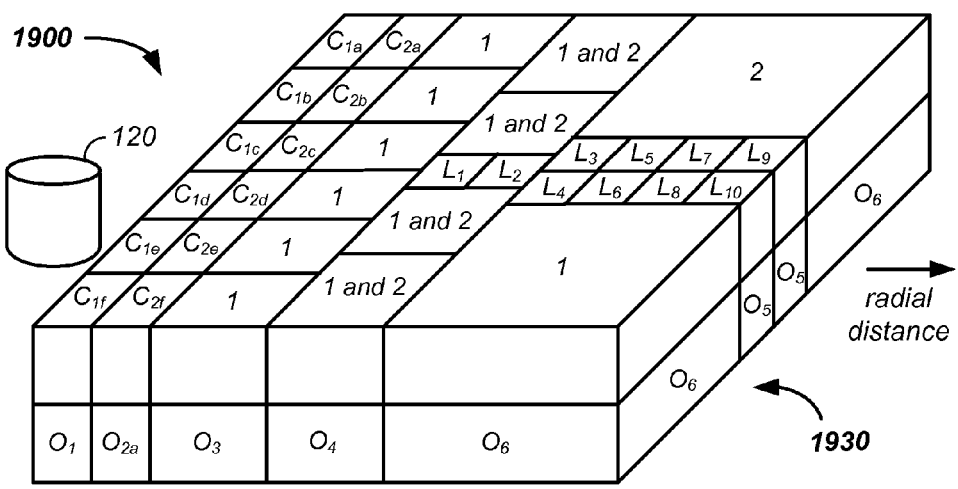

Referring now to FIG. 19A and FIG. 19B, a two-dimensional detector array/guiding optic array assembly 1900 is illustrated proximate output of the photon transport system 120, illustrated as an array of incident light optics proximate skin tissue, where the skin is not illustrated. For clarity of presentation and without limitation, the detector array/guiding optic array assembly 1900 is illustrated and described as a single assembled detector/optic unit 1930. However, optionally, the two-dimensional guiding optic array 1920 is optionally proximate the two-dimensional detector array 134, such as within less than 20, 10, 5, 2, 1, or 0.5 millimeters or is well removed from the two-dimensional detector array 134, such as at any position in the optical train between the skin of the subject 170 and the detector system 130. Further, the two-dimensional guiding optic arrays is optionally on either optical train side of one or more of the optional two-dimensional filter arrays.

Still referring to FIG. 19A and FIG. 19B, varying optional detector shape/optical filter combinations are described.

In a first case, two or more detector elements of the two-dimensional detector array 134 are optically coupled with a single optic. For example, the first column of detectors in the two-dimensional detector array 134 are coupled with a single optic, $O_1$. The single optic, $O_1$, is optionally a pathlength extending optic, which redirects light to include a vector component back toward the illumination zone resulting in a longer mean pathlength and/or depth of penetration. The pathlength extending optic is optionally and preferably used close to the illumination zone, in this case to the left of the two-dimensional/guiding optic array assembly 1900, to yield additional photons in sampling the dermis region and fewer photons sampling solely the epidermis region, as described supra in relation to FIG. 7A. The extending optic is particularly useful with a combination band source/combination band filter/detector combination.

In a second case, 1, 2, 3, 4, or more individual detector elements of the two-dimensional detector array 134 are optionally each optically coupled with discrete individual optics of the two-dimensional optic array 1920. For example, as illustrated, the second column of detectors comprise combination band detectors, $C_{2(a-f)}$, each coupled with standard focusing optics and/or optics redirecting light to comprise a vector back toward the mean radial axis of detected incident photons, $C_{2b,2e}$. Optionally, the further from the mean radial axis of the detected incident photons, the greater the magnitude of the induced vector component redirecting photons back toward the mean radial axis, $C_{2a,2f}$.

In a third case, light gathering areas of individual optics in the two-dimensional optic array 1920 are optionally larger with increasing distance from an illumination zone proximate incident light entering skin of the subject 170 from the photon transport system 120. For example a sixth optic, $O_6$, optionally has a larger surface area along the y/z-plane compared to a fourth optic, $O_4$, which has a larger area than a third optic, $O_3$, which has a larger area than a second optic, $O_{2a}$. For a noninvasive near-infrared spectral measurement, the generally, but not absolutely, larger collection areas as a function of radial distance from the illumination zone aid signal-to-noise ratios due to fewer photons reaching the larger radial distances. The optic size matched to spectral region is further described, infra.

In a fourth case, light gathering areas along the y/z-plane are chosen to enhance signal-to-noise ratios for varying spectral regions, such as the combination band region 950, the first overtone region 960, the second overtone region 970, and/or one or more narrowband analyte specific regions. For example, observed light intensity generally decreases with increased radial distance from an illumination zone in the spectral region of 1100 to 2500 nm. Further, the radial distance needed to obtain quality/high signal-to-noise ratio spectra using dermal layer probing photons generally varies with radial distance from the illumination zone. The inventor has determined that a series of detector types, optical filters, and/or light gathering areas are preferentially used, such as: a combination band region detector, $C_{2a}$, at close radial distance to the source with a first optic collection area, $O_{2a}$; a first overtone detector, 1, at an intermediate radial distance to the source with a second optic collection area, $O_3$; a first and second overtone detector, 1 and 2, at a still further radial distance from the illumination zone with a third collection optic area, $O_4$; and/or a second overtone detector, 2, at a yet still further radial distance from the illumination zone with a fourth optic collection area, $O_6$.

In a fifth case, the two-dimensional detector area 134 contains a greater or first number of detector elements in a given area at a first radial distance from the illumination zone and a lesser or second number of detector elements in a second equally sized area at a second greater radial distance from the illumination zone. For example, the first number of detector elements is optionally 10, 20, 30, 40, 50, 100, 150, 200, or more percent larger than the second number of detector elements.

In a sixth case, more than one optic size, in the y/z-plane is used for a single column or row of detector elements of the two-dimensional detector array 134, such as the fourth and fifth optic, $O_4$ and $O_5$, associated with the fourth detector column in the provided example.

In a seventh case, one or more filters are optically coupled to one or more corresponding elements of the two-dimensional detector array 132 and/or to one or more corresponding elements of the two-dimensional optic array 1920.

In an eighth case, one or more detector elements of the two-dimensional detector array are optically coupled to one or more luminance filters.

Two-Dimensional Detector/Optical Filter/Guiding Optic Combinations

Referring now to FIGS. 20(A&B) and FIGS. 21(A&B), various exemplary combinations of the two-dimensional detector array 134/the two-dimensional filter array 1510/two-dimensional optic array 1920 are provided. Herein, examples are provided for clarity of presentation and without limitation. Generally, the examples represent any combination and/or permutation of the two-dimensional detector array 134, the two-dimensional filter array 1510, and/or the two-dimensional optic array 1920. Further, for clarity of presentation and without limitation, the two-dimensional filter array 1510 is depicted as two optional arrays, a two-dimensional longpass filter array 1512 and a two-dimensional shortpass filter array 1514. Still further, the two-dimensional detector array 134, the two-dimensional longpass filter array 1512, the two-dimensional shortpass filter array 1514, and the two-dimensional optic array 1920 are optionally individually spaced from one another, are optionally contacting each other as in a detector/filter/optic assembly 2050, and/or have gaps between one or more of the individual two-dimensional arrays.

Figure 20A:
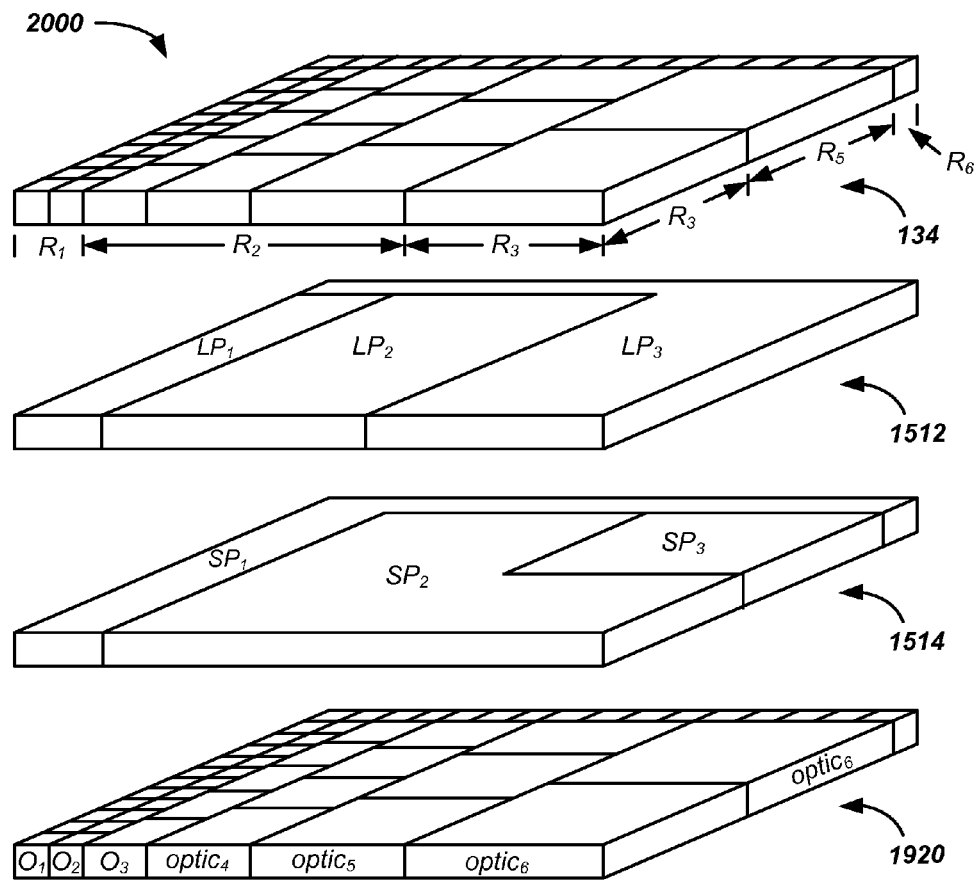
FIG. 20A and FIG. 20B illustrate a detector array, longpass filter array, shortpass filter array, and optic array in an exploded and assembled view, respectively.
Figure 20B:
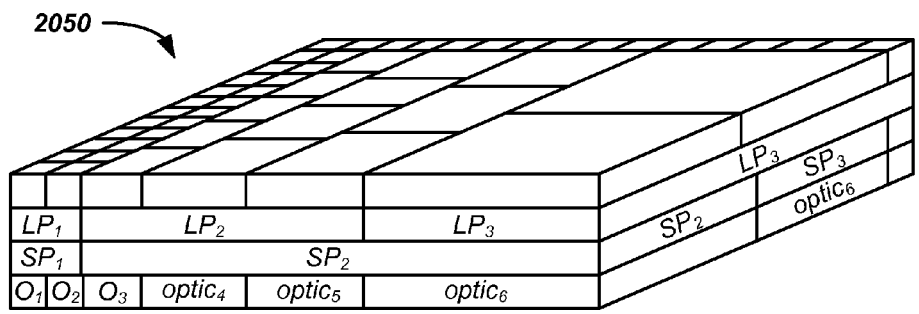

Referring now to FIG. 20A and FIG. 20B, a first example of a two-dimensional detector/filter/optic system 2000 is described. In this first example, the two-dimensional detector array 134 contains a plurality of detectors in any geometric pattern, of one or more sizes. Further, the optional two-dimensional filter array 1510 is depicted as layers of longpass filter elements and/or shortpass filter elements, such as the two-dimensional longpass filter array 1512 and/or the two-dimensional shortpass filter array 1514. The two-dimensional longpass filter array 1512 is optionally 1, 2, 3, or more filter types, $LP_1$, $LP_2$, $LP_3$. Similarly, the two-dimensional shortpass filter array 1514 is optionally 1, 2, 3, or more filter types, $SP_1$, $SP_2$, $SP_3$. Optionally, elements of the two-dimensional shortpass filter array 1514 are present in the two-dimensional longpass filter array 1512 and vise-versa. Still further, the optional two-dimensional optic layer 1920 contains 1, 2, 3, or more optic sizes and/or types, $O_1$, $O_2$, $O_3$ Optionally, one or more of the longpass and/or shortpass filters overlap one or more detectors or optics of the two-dimensional detector array 132 and two-dimensional optic array 1920, respectively. Optionally, one or more edges of a longpass filter element of the two-dimensional longpass filter array 1512 do not align with one or more edges of a shortpass filter of the two-dimensional shortpass filter array 1514 or vise-versa. Generally, multiple configurations of the two-dimensional detector/filter/optic system 2000 are useful in a noninvasive analyte concentration determination, such as a noninvasive spectral determination of glucose concentration. One exemplary configuration is provided, infra.

Figure 21A:
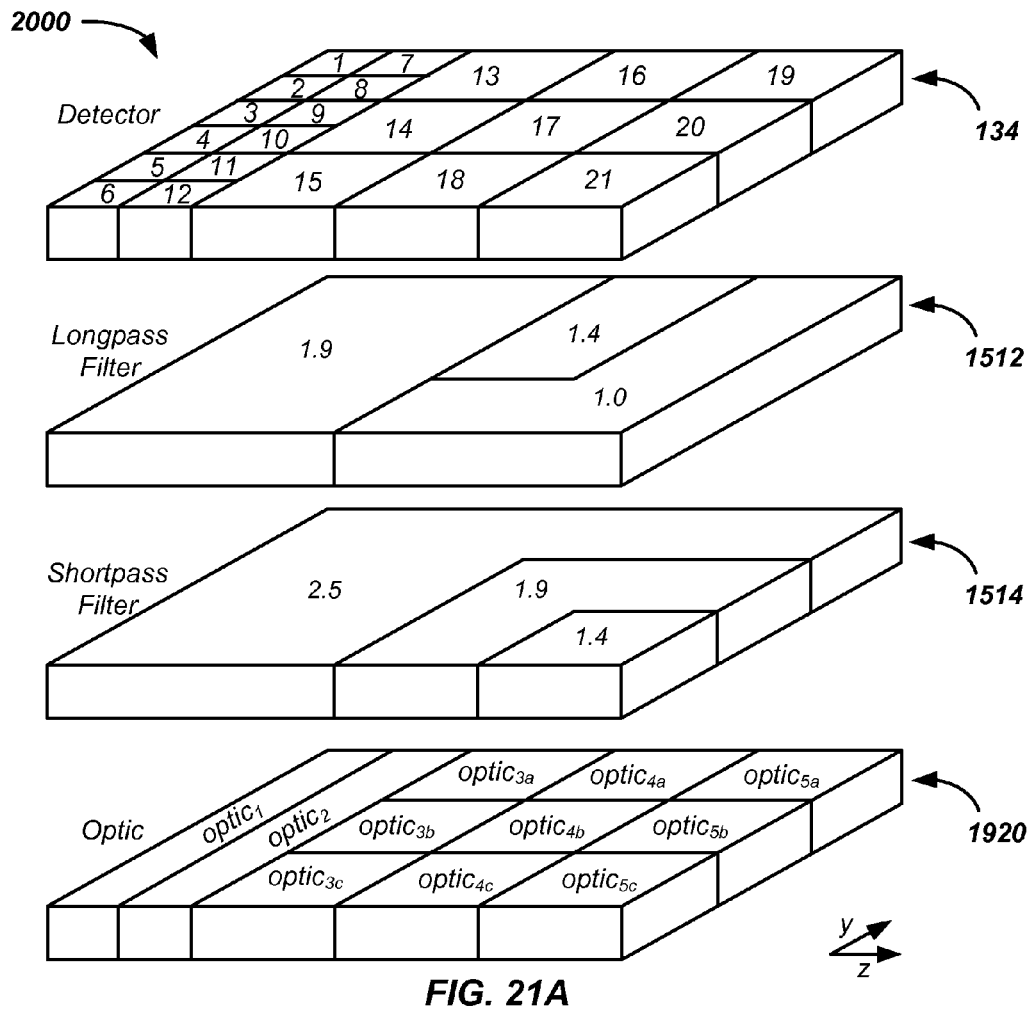
FIG. 21A and FIG. 21B illustrate a detector array, longpass filter array, shortpass filter array, and optic array in an exploded and assembled view, respectively.
Figure 21B:
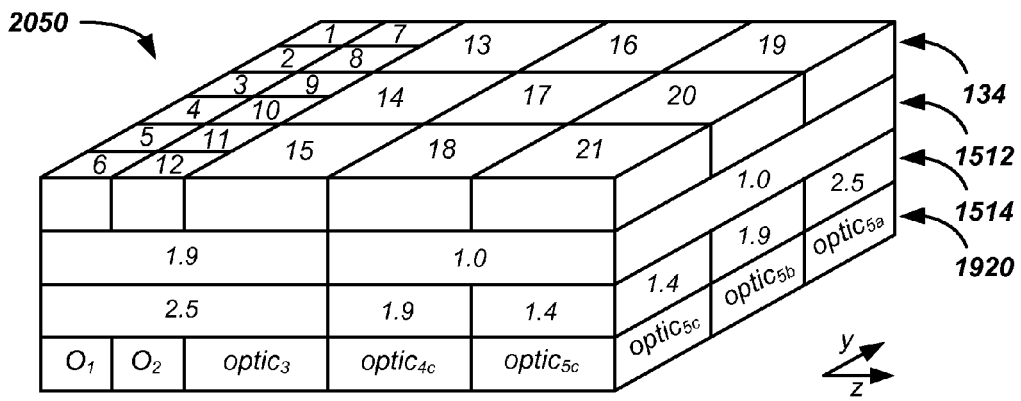

Referring now to FIG. 21A and FIG. 21B, a second example of the two-dimensional detector/filter/optic system 2000 is described. In this second example, for clarity of presentation particular detector types, filter parameters, spectral regions, and/or optics are described that are representative of many possible detector, filter, and/or optical configurations. In this second example, filters and optics for varying spectral regions are provided in Table 1.

TABLE 1

Simultaneous Multiple Region Analysis

| Detector(s) | Detector Type* | Longpass Filter (μm) | Shortpass Filter (μm) | Optic | Region |
|---|---|---|---|---|---|
| 1-6 | 2.5 | 1.9 | 2.5 | Pathlength Extending | Combination Band |
| 7-12 | 2.5 | 1.9 | 2.5 | Standard | Combination Band |
| 13-15 | 2.5 | 1.9 | 2.5 | Focusing | Combination Band |
| 16 | 2.5 | 1.4 | 2.5 | Focusing | Combination Band and $1^{st}$ Overtone |
| 17 | 1.9 | 1.4 | 1.9 | Focusing | $1^{st}$ Overtone |
| 18 | 1.9 | 1.0 | 1.9 | Focusing | $1^{st}$ and $2^{nd}$ Overtone |
| 19 | 2.5 | 1.0 | 2.5 | Pathlength Reducing | Broadband |
| 20 | 1.9 | 1.0 | 1.9 | Pathlength Reducing | $1^{st}$ and $2^{nd}$ Overtone |
| 21 | 1.7 | 1.0 | 1.4 | Pathlength Reducing | $2^{nd}$ Overtone |

*non-limiting examples of InGaAs detector cut-off wavelengths

From Table 1, it is observed that optionally multiple spectral regions are simultaneously observed with a single two-dimensional detector array. It is further noted that observed mean sampled pathlengths and observed mean sampled depths of penetration correspond with filter types changing as a function of relative radial distance from an illumination zone; the illumination zone to the left of the illustrated two-dimensional detector and associated optics. Still further, if additional emphasis is desired for a particular spectral region, more detectors are simply used with the appropriate filter combination. For example, if more first overtone spectra are desired, the area of optics associated with detector 17 is optionally expanded along the y-axis for similar pathlengths and/or along the z-axis for longer and/or shorter mean pathlengths.

Multiple combinations of filter types and/or optic types are optionally used in the noninvasive analyte spectral determination process. Table 2 shows an exemplary configuration for a noninvasive analysis performed using the first overtone 960 and second overtone 970 spectral regions. From Table 2, it is again observed that, optionally, multiple spectral regions are simultaneously observed with a single two-dimensional detector array optically coupled to an array of filter types and/or an array of light directing optics.

TABLE 2

Simultaneous Multiple Region Analysis

| Detector Column | Longpass Filter (μm) | Shortpass Filter (μm) | Optic | Region |
|---|---|---|---|---|
| 1 | 1.4 | 1.9 | Pathlength Extending | First Overtone |
| 2 | 1.6 | 1.4 | Standard | Analyte Band |
| 3 | 1.4 | 1.9 | Focusing | First Overtone |
| 4 | 1.6 | 1.4 | Focusing | Analyte Band |
| 5 | 1.1 | 1.9 | Standard | $1^{st}$ and $2^{nd}$ Overtone |
| 6 | 1.1 | 1.9 | Focusing | $1^{st}$ and $2^{nd}$ Overtone |
| 7 | 1.0 | 1.7 | Focusing | Extended $2^{nd}$ Overtone |
| 8 | 1.0 | 1.4 | Focusing | $2^{nd}$ Overtone |
| 9 | 1.0 | 1.4 | Pathlength Reducing | $2^{nd}$ Overtone |

Temporal Resolution

The second method of temporal resolution is optionally performed in a number of manners. For clarity of presentation and without limitation, a temporal resolution example is provided where photons are timed using a gating system and the elapsed time is used to determine photon paths in tissue.

Referring now to FIGS. 22(A-D), an example of a temporally resolved gating system 2200 is illustrated. Generally, in the temporal gating system 2200 the time of flight of a photon is used to determine the pathlength, b. Referring now to FIG. 22A, at an initial time, $t_0$, an interrogation pulse 2210 of one or more photons is introduced to the sample, which herein is skin of the subject 170. The interrogation pulse 2210 is also referred to as a pump pulse or as a flash of light. At one or more subsequent gated detection times 2220, after passing through the sample the interrogation pulse 2210 is detected. As illustrated, the gated detection times are at a first time 2222, $t_1$; a second time 2224, $t_2$; a third time 2226, $t_3$; and at an $n^{th}$ time 2228, $t_n$, where n is a positive number. Optionally, the gated detection times 2220 overlap. For the near-infrared spectral region, the elapsed time used to detect the interrogation photons 2210 is on the order of picoseconds, such as less than about 100, 10, or 1 picosecond. The physical pathlength, b, is determined using equation 2:

$$OPD = \frac{c}{n}(b) \qquad (eq.\ 2)$$

where OPD is the optical path distance, c is the speed of light, n is the index of refraction of the sample, and b is the physical pathlength. Optionally, n is a mathematical representation of a series of indices of refraction of various constituents of skin and/or skin and surrounding tissue layers. More generally, observed pathlength is related to elapsed time between photon launch and photon detection where the pathlength of photons in the sample is related to elapsed time, optionally with one or more additional variables related to one or more refractive indices.

Referring now to FIG. 22B, illustrative paths of the photons for the first gated detection time 2222 are provided. A first path, $p_{1a}$; second path, $p_{1b}$; and third path, $p_{1c}$, of photons in the tissue are illustrated. In each case, the total pathlength, for a constant index of refraction, is the same for each path. However, the probability of each path also depends on the anisotropy of the tissue and the variable indices of refraction of traversed tissue voxels.

Referring now to FIG. 22C, illustrative paths of the photons for the second gated detection time 2224 are provided. A first path, $p_{2a}$; second path, $p_{2b}$; and third path, $p_{2c}$, of photons in the tissue are illustrated. Again, in each case the total pathlength for the second elapsed time, $t_2$, is the same for each path. Generally, if the delay to the second gated detection time 2224 is twice as long as the first gated detection time 2222, then the second pathlength, $p_2$, for the second gated detection time 2224 is twice as long as the first pathlength, $p_1$, for the first gated detection time 2222. Knowledge of anisotropy is optionally used to decrease the probability spread of paths observed in the second set of pathlengths, $p_{ea}$, $p_{2b}$, $p_{2c}$. Similarly a-priori knowledge of approximate physiological thickness of varying tissue layers, such as an epidermal thickness of a patient, an average epidermal thickness of a population, a dermal thickness of a patient, and/or an average dermal thickness of a population is optionally used to reduce error in an estimation of pathlength, a product of pathlength and a molar absorptivity, and/or a glucose concentration by limiting bounds of probability of a photon traversing different pathways through the skin layers and still returning to the detection element with the elapsed time. Similarly, knowledge of an index of refraction of one or more sample constituents and/or a mathematical representation of probable indices of refraction is also optionally used to reduce error in estimation of a pathlength, molar absorptivity, and/or an analyte property concentration estimation. Still further, knowledge of an incident point or region of light entering she skin of the subject relative to a detection zone is optionally used to further determine probability of a photon traversing dermal or subcutaneous fat layers along with bounding errors of pathlength in each layer.

Referring now to FIG. 22D, mean pathlengths and trajectories are illustrated for three elapsed times, $t_1$, $t_2$, $t_3$. As with the spatially resolved method, generally, for photons in the near-infrared region from 1100 to 2500 nanometers, both a mean depth of penetration of the photons, $d_n$; the total radial distance traveled, $r_m$; and the total optical pathlength increases with increasing time, where the fiber optic-to-detector distance is less than about three millimeters. Preferably, elapsed times between a pulse of incident photon delivery and time gated detection are in a range between 100 nanoseconds and 100 picoseconds, such as about 1, 5, 10, and 50 picoseconds.

Spatial and Temporal Resolution

Hence, both the spatial resolution method and temporal resolution method yield information on pathlength, b, which is optionally used by the data processing system 140 to reduce error in the determined concentration, C.

Analyzer and Subject Variation

As described, supra, Beer's Law states that absorbance, A, is proportional to pathlength, b, times concentration, C. More precisely, Beer's Law includes a molar absorbance, $\epsilon$, term, as shown in equation 3:

$$A = \epsilon b C \quad \text{(eq. 3)}$$

Typically, spectroscopists consider the molar absorbance as a constant due to the difficulties in determination of the molar absorbance for a complex sample, such as skin of the subject 170. However, information related to the combined molar absorbance and pathlength product for skin tissue of individuals is optionally determined using one or both of the spatially resolved method and time resolved method, described supra. In the field of noninvasive glucose concentration determination, the product of molar absorbance and pathlength relates at least to the dermal thickness of the particular individual or subject 170 being analyzed. Examples of spatially resolved analyzer methods used to provide information on the molar absorbance and/or pathlength usable in reduction of analyte property estimation and/or uncertainty determination are provided infra.

Spatially Resolved Analyzer

Herein, an analyzer 100 using fiber optics is used to describe obtaining spatially resolved information, such as pathlength and/or molar absorbance, of skin of an individual, which is subsequently used by the data processing system 140. The use of fiber optics in the examples is used without limitation, without loss of generality, and for clarity of presentation. More generally, photons are delivered in quantities of one or more through free space, through optics, and/or off of reflectors to the skin of the subject 170 as a function of distance from a detection zone.

Figure 23A:
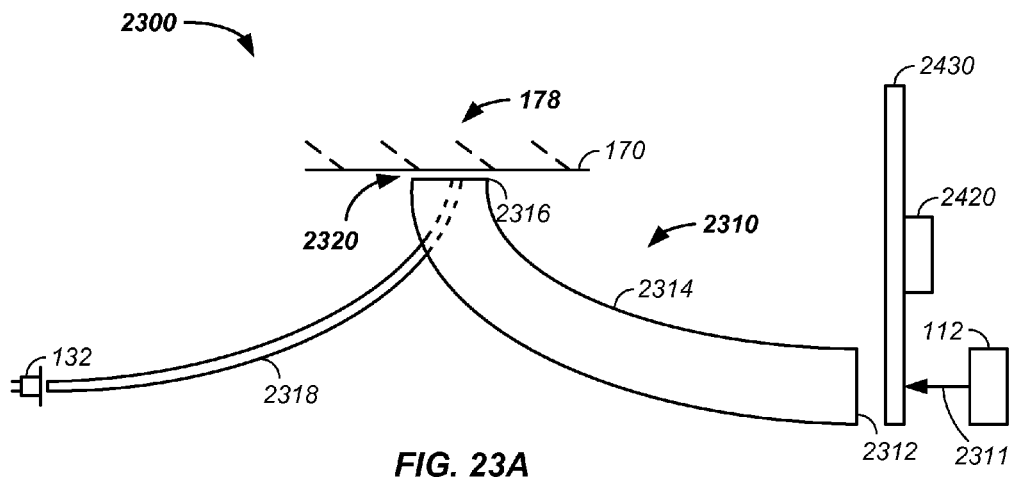
FIGS. 23(A-C) illustrate a fiber optic bundle, FIG. 23A; a first example sample interface end of the fiber optic bundle, FIG. 23B; and a second example sample interface end of the fiber optic bundle, FIG. 23C.

Referring again to FIG. 1 and referring now to FIG. 23A, an example of a fiber optic interface system 2300 of the analyzer 100 to the subject 170 is provided, which is an example of the sample interface system 150. Light from the source system 110 of the analyzer 100 is coupled into a fiber optic illumination bundle 2314 of a fiber optic bundle 2310. The fiber optic illumination bundle 2314 guides light to a sample site 178 of the subject 170. The sample site 178 has a surface area and a sample volume. In a first case, a sample interface tip 2316 of the fiber optic bundle 2310 contacts the subject 170 at the sample site 178. In a second case, the sample interface tip 2316 of the fiber optic bundle 2310 proximately contacts the subject 170 at the sample site 178, but leaves a sample interface gap 2320 between the sample interface tip 2316 of the fiber optic bundle 2310 and the subject 170. In one instance, the sample interface gap 2320 is filled with a contact fluid and/or an optical contact fluid. In a second instance, the sample interface gap 2320 is filled with air, such as atmospheric air. Light transported by the fiber optic bundle 2310 to the subject 170 interacts with tissue of the subject 170 at the sample site 178. A portion of the light interacting with the sample site is collected with one or more fiber optic collection fibers 2318, which is optionally and preferably integrated into the fiber optic bundle 2310. As illustrated, a single collection fiber 2318 is used. The collection fiber 2318 transports collected light to the detector 132 of the detection system 130.

Figures 23B, 23C:
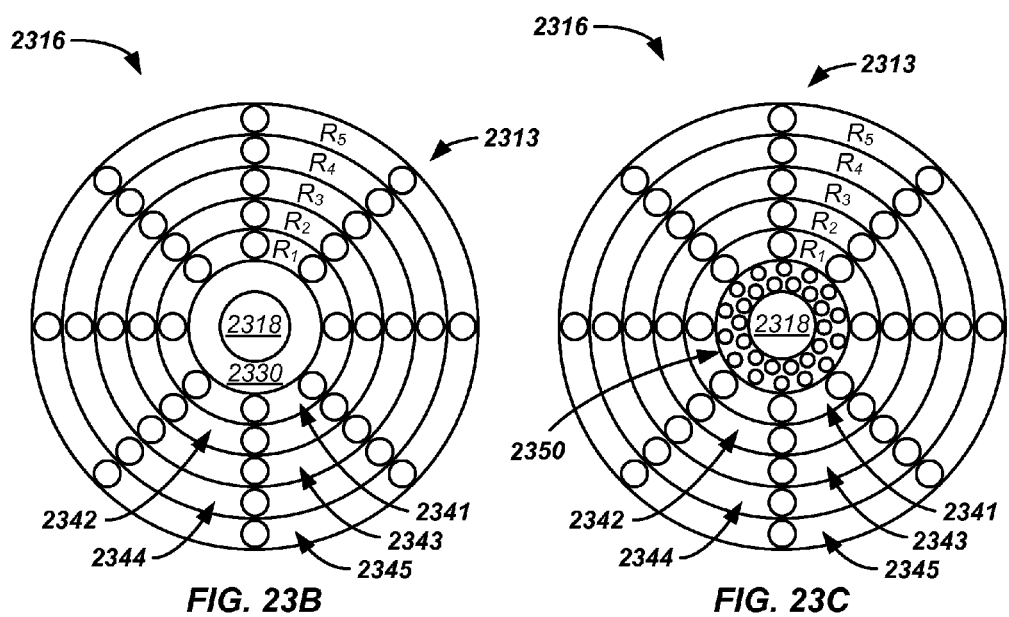

Referring now to FIG. 23B, a first example of a sample side light collection end 2316 of the fiber optic bundle 2310 is illustrated. In this example, the single collection fiber 2318 is circumferentially surrounded by an optional spacer 2330, where the spacer has an average radial width of less than about 200, 150, 100, 50, or 25 micrometers. The optional spacer 2330 is circumferentially surrounded by a set of fiber optic elements 2313. As illustrated, the set of fiber optic elements 2313 are arranged into a set of radial dispersed fiber optic rings, such as a first ring 2341, a second ring 2342, a third ring 2343, a fourth ring 2344, and an $n^{th}$ ring 2345, where n comprises a positive integer of at least 2, 3, 4, 5, 6, 7, 8, 9, or 10. Optionally, the fiber optic elements 2313 are in any configuration, such as in a close-packed configuration about the collection fiber 2318 or in an about close-packed configuration about the collection fiber 2318. The distance of each individual fiber optic of the set of fiber optic elements 2313, or light collection element, from the center of the collection fiber 2318 is preferably known.

Referring now to FIG. 23C, a second example of the sample side light collection end 2316 of the fiber optic bundle 2310 is provided. In this example, the centrally positioned collection fiber 2318 is circumferentially surrounded by a set of spacer fibers 2350. The spacer fibers combine to cover a radial distance from the outside of the collection fiber of less than about 300, 200, 150, 100, 75, 60, 50, or 40 micrometers. The spacer fibers 2350 are circumferentially surrounded by the radially dispersed fiber optic rings, such as the first ring 2341, the second ring 2342, the third ring 2343, the fourth ring 2344, and the $n^{th}$ ring 2345. Optionally, fiber diameters of the spacer fibers 2350 are at least ten, twenty, or thirty percent larger or smaller than fiber diameters of the set of fiber optic elements 2313. Further, optionally the fiber optic elements 2313 are arranged in any spatial configuration radially outward from the spacer fibers 2350. More generally, the set of fiber optic elements 2313 and/or spacer fibers 2350 optionally contain two, three, four, or more fiber optic diameters, such as any of about 40, 50, 60, 80, 100, 150, 200, or more micrometers. Optionally, smaller diameter fiber optics, or light collection optics, are positioned closer to any detection fiber and progressively larger diameter fiber optics are positioned, relative to the smaller diameter fiber optics, further from the detection fiber.

Radial Distribution System

Referring now to FIG. 24A, FIG. 24B, FIG. 25, and FIGS. 26 A-D a system for spatial illumination 2400 of the sample site 178 of the subject 170 is provided. The spatial illumination system 2400 is used to control distances between illumination zones and detection zones as a function of time. In a first case, light is distributed radially relative to a detection zone using a fiber optic bundle. In a second case, light is distributed radially relative to a detection zone using a reflective optic system and/or a lens system. Generally, the first case and second case are non-limiting examples of radial distribution of light about one or more detection zones as a function of time.

Radial Position Using Fiber Optics

Referring now to FIG. 24A, a third example of the sample side light collection end 2316 of the fiber optic bundle 2310 is provided. In this example, the collection fiber 2318 or collection optic is circumferentially surrounded by the set of fiber optic elements 2313 or irradiation points on the skin of the subject 170. For clarity of presentation and without loss of generality, the fiber optic elements 2313 are depicted in a set of rings radially distributed from the collection fiber 2318. However, it is understood that the set of fiber optics 2313 are optionally close packed, arranged in a random configuration, or arranged according to any criterion. Notably, the distance of each fiber optic element of the set of fiber optic elements 2313 from the collection fiber 2318 is optionally determined using standard measurement techniques through use of an algorithm and/or through use of a dynamically adjustable optic used to deliver light to the sample, such as through air. Hence, the radial distribution approach, described infra, is optionally used for individual fiber optic elements and/or groups of fiber optic elements arranged in any configuration. More generally, the radial distribution approach, described infra, is optionally used for any set of illumination zone/detection zone distances using any form of illuminator and any form of detection system, such as through use of the spatially resolved system and/or the time resolved system.

Referring now to FIG. 24B, an example of a light input end 2312 of the fiber optic bundle 2310 is provided. In this example, individual fibers of the set of fiber optics 2313 having the same or closely spaced radial distances from the collection fiber 2318 are grouped into a set of fiber optic bundles or a set of fiber optic bundlets 2410. As illustrated, the seven fibers in the first ring circumferentially surrounding the collection fiber 2318 are grouped into a first bundlet 2411. Similarly, the sixteen fibers in the second ring circumferentially surrounding the collection fiber 2318 are grouped into a second bundlet 2412. Similarly, the fibers from the third, fourth, fifth, and sixth rings about the collection fiber 2318 at the sample side illumination end 2316 of the fiber bundle 2310 are grouped into a third bundlet 2413, a fourth bundlet 2414, a fifth bundlet 2415, and a sixth bundlet 2416, respectively. For clarity of presentation, the individual fibers are not illustrated in the second, third, fourth, fifth, and sixth bundlets 2412, 2413, 2414, 2415, 2416. Individual bundles and/or individual fibers of the set of fiber optic bundlets 2410 are optionally selectively illuminated using a mask 2420, described infra.

Referring now to FIG. 25 and FIG. 23A, a mask wheel 2430 is illustrated. Generally, the mask wheel 2430 rotates, such as through use of a wheel motor 2420. As a function of mask wheel rotation position, holes or apertures through the mask wheel 2430 selectively pass light from the source system 110 to the fiber optic input end 2312 of the fiber optic bundle 2310. In practice, the apertures through the mask wheel are precisely located to align with (1) individual fiber optic elements of the set of fiber optics at the input end 2312 of the fiber optic bundle or (2) individual bundlets of the set of fiber optic bundlets 2410. Optionally an encoder or marker section 2440 of the mask wheel 2430 is used for tracking, determining, and/or validating wheel position in use.

Still referring to FIG. 25, an example of use of the mask wheel 2430 to selectively illuminate individual bundlets of the set of fiber optic bundlets 2410 is provided. Herein, for clarity of presentation the individual bundlets are each presented as uniform size, are exaggerated in size, and are repositioned on the wheel. For example, as illustrated a first mask position, $p_1$, 2421 is illustrated at about the seven o'clock position. The first mask position 2421 figuratively illustrates an aperture passing light from the source system 110 to the first bundlet 2411 while blocking light to the second through sixth bundlets 2412-2416. At a second point in time, the mask wheel 2430 is rotated such that a second mask position, $p_2$, 2422 is aligned with the input end 2312 of the fiber optic bundle 2310. As illustrated, at the second point in time, the mask wheel 2430 passes light from the illumination system 110 to the second bundlet 2412, while blocking light to the first bundlet 2411 and blocking light to the third through six bundlets 2413-2416. Similarly, at a third point in time the mask wheel uses a third mask position, $p_3$, 2423 to selectively pass light into only the fifth bundlet 2415. Similarly, at a fourth point in time the mask wheel uses a fourth mask position, $p_4$, 2424 to selectively pass light into only the sixth bundlet 2416.

Still referring to FIG. 25, thus far the immediately prior example has only shown individual illuminated bundlets as a function of time. However, combinations of bundlets are optionally illuminated as a function of time. In this continuing example, at a fifth point in time, the mask wheel 2430 is rotated such that a fifth mask position, $p_5$, 2425 is aligned with the input end 2312 of the fiber optic bundle 2310. As illustrated, at the fifth point in time, the mask wheel 1130 passes light from the illumination system 110 to all of (1) the second bundlet 2412, (2) the third bundlet 2413, and (3) the fourth bundlet 2414, while blocking light to all of (1) the first bundlet 2411, (2) the fifth bundlet 2415, and (3) the sixth bundlet 2416. Similarly, at a sixth point in time a sixth mask position, $p_6$, 2426 of the mask wheel 2430 passes light to the second through fifth bundlets 2412-2415 while blocking light to both the first bundlet 2411 and sixth bundlet 2416.

In practice, the mask wheel 2430 contains an integral number of n positions, where the n positions selectively illuminate and/or block any combination of: (1) the individual fibers of the set of fiber optics 2313 and/or (2) bundlets 2410 of the set of fiber optic optics 2313. Further, the filter wheel is optionally of any shape and uses any number of motors to position mask position openings relative to selected fiber optics. Still further, in practice the filter wheel is optionally any electromechanical and/or electro-optical system used to selectively illuminate the individual fibers of the set of fiber optics 2313. Yet still further, in practice the filter wheel is optionally any illumination system that selectively passes light to any illumination optic or illumination zone, where various illumination zones illuminate various regions of the subject 170 as a function of time. The various illumination zones alter the effectively probed sample site 178 or region of the subject 170.

Radial Position Using a Mirror and/or Lens System

Referring now to FIGS. 26(A-D), a dynamically positioned optic system 2300 for directing incident light to a radially changing position about a collection zone is provided.

Figure 26A:
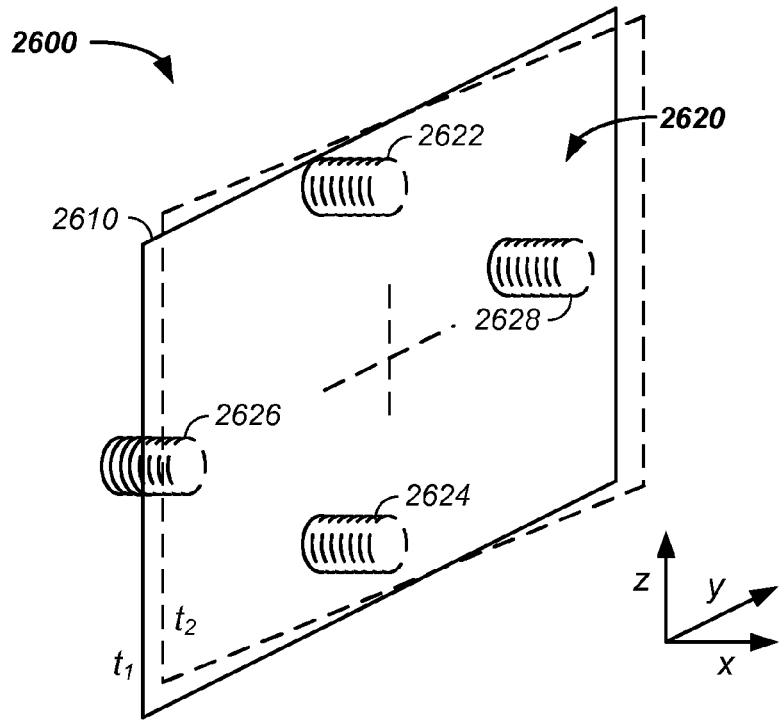
FIG. 26A illustrates a position selection optic.

Referring now to FIG. 26A, a mirror 2610 is illustrative of any mirror, lens, mirror system, and/or lens system used to dynamically and positionally direct incident light to one or more illumination zones of the subject 170 relative to one or more detection zones and/or volumes monitored by the photon transport system 120 and/or the detector system 130.

Still more generally, the data processing system 140 and/or the system controller 180 optionally control one or more optics, figuratively illustrated as the mirror 2310, to dynamically control incident light 2311 on the subject 170 relative to a detection zone on the subject 170 that combine to form the sample site 178 through control of one or more of:

x-axis position of the incident light on the subject 170;
y-axis position of the incident light on the subject 170;
solid angle of the incident light on a single fiber of the fiber bundle 2410;
solid angle of incident light on a set of fibers of the fiber bundle 2410;
a cross-sectional diameter or width of the incident light;
an incident angle of the incident light on the subject 170 relative to an axis perpendicular to skin of the subject 170 where the incident light interfaces to the subject 170;
focusing of the incident light; and/or
depth of focus of the incident light on the subject 170.

Several examples are provided, infra, to further illustrate the use of the system controller 180 to control shape, position, and/or angle of the incident light 2311 reaching a fiber optic bundle, skin of the subject 170, and/or an element of the photon transport system 120.

Referring again to FIG. 26A, an example is provided of light directed by the photon transport system 120 from the source system 110 to the subject directly, through one or more fiber optic of the fiber optic bundle 2410, and/or through the photon transport system 120. However, orientation of the mirror 2610 is varied as a function of time relative to an incident set of photons pathway. For example, the mirror 2610 is translated along the x-axis of the mean optical path, is rotated about the y-axis of the mean optical path, and/or is rotated about the z-axis of the mean optical path of the analyzer 100. For example, a first mirror movement element 2622, such as a first spring or piezoelectric device, and a second mirror movement element 2624, such as a second spring, combine to rotate the mirror about a first axis, such as the y-axis as illustrated. Similarly, a third mirror movement element 2626, such as a third spring, and a fourth mirror movement element 2628, such as a fourth spring, combine to rotate the mirror about a second axis, such as the z-axis as illustrated, in the second time position, $t_2$, relative to a first time position, $t_1$.

Figure 26B:
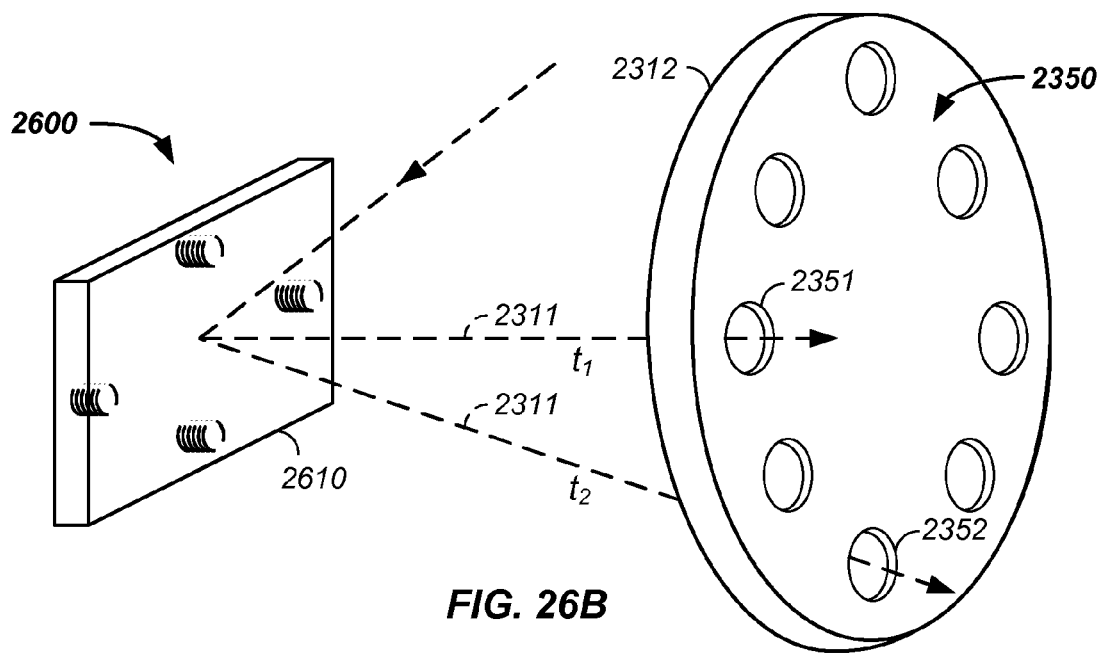
FIG. 26B illustrates the position selection optic selecting position.

Referring now to FIG. 26B, an example of the dynamically positioned optic system 2600 directing the incident light 2311 to a plurality of positions as a function of time is provided. As illustrated, the mirror 2610 directs light to the light input end 2312 of the fiber bundle 2310. Particularly, the incident light 2311 is directed at a first time, $t_1$, to a first fiber optic 2351 and the incident light 2311 is directed at a second time, $t_2$, to a second fiber optic 2352 of a set of fiber optics 2350. However, more generally, the dynamically positioned optic system 2600 directs the incident light using the mirror 2600 to any y-, z-axis position along the x-axis of the incident light as a function of time, such as to any optic and/or to a controlled position of skin of the subject 170.

Figure 26C:
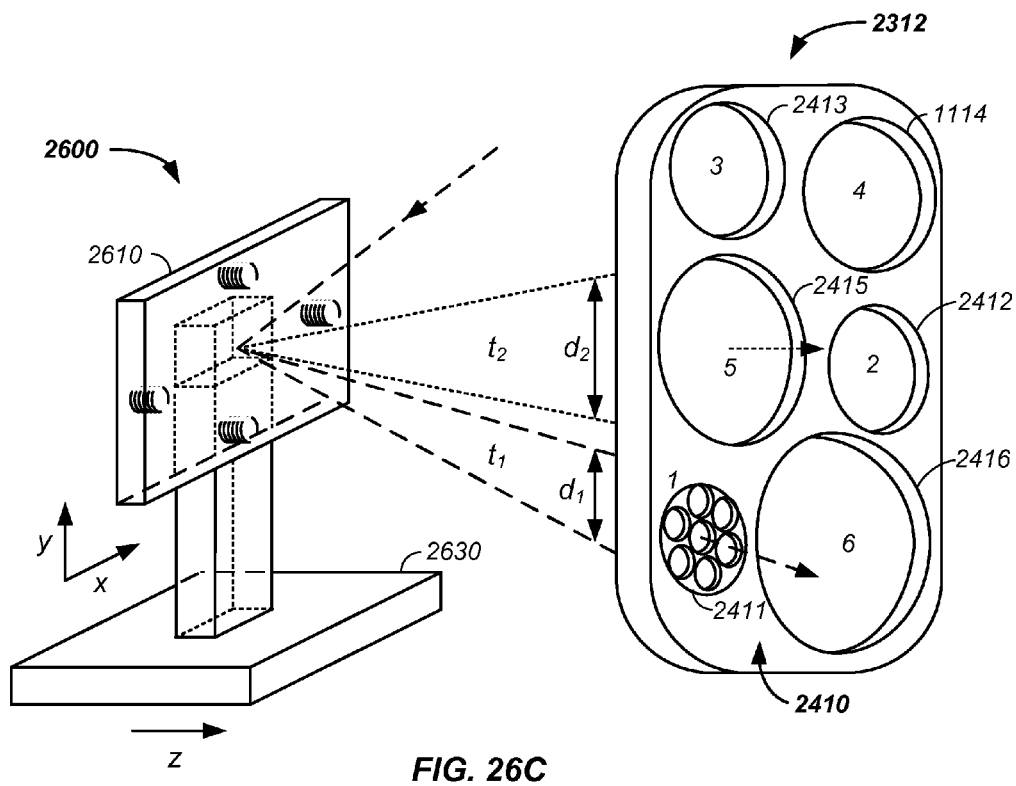
FIG. 26C illustrates solid angle selection using the position selection optic.

Referring now to FIG. 26C, an example of the dynamically positioned optic system 2300 directing the incident light to a plurality of positions with a controllable and varying as a function of time solid angle is provided. Optionally, the solid angle is fixed as a function of time and the position of the incident light 2311 onto the light input end 2312 of the fiber bundle 2310 is varied as a function of time. As illustrated, the mirror 2610 directs light to the light input end 2312 of the fiber bundle 2310 where the fiber bundle 2310 includes one or more bundlets, such as the set of fiber optic bundlets 2410. In this example, the incident light is directed at a first time, $t_1$, with a first solid angle to a first fiber optic bunch or group, such as the first bundlet 2411, described supra, and at a second time, $t_2$, with a second solid angle to a second fiber optic bunch, such as the second bundlet 2412, described supra. In one case, the first solid angle and second solid angle do not overlap, such as at the fiber optic interface. In another case, the first solid angle and the second solid angle overlap by less than 20, 40, 60, or 80 percent. However, more generally, the dynamically positioned optic system 2600 directs the incident light to any y-, z-axis position along the x-axis of the incident light as a function of time at any solid angle or with any focusing angle, such as to any optic, any group of optics, and/or to a controlled position and/or size of skin of the subject 170 relative to a detection zone.

Figure 26D:
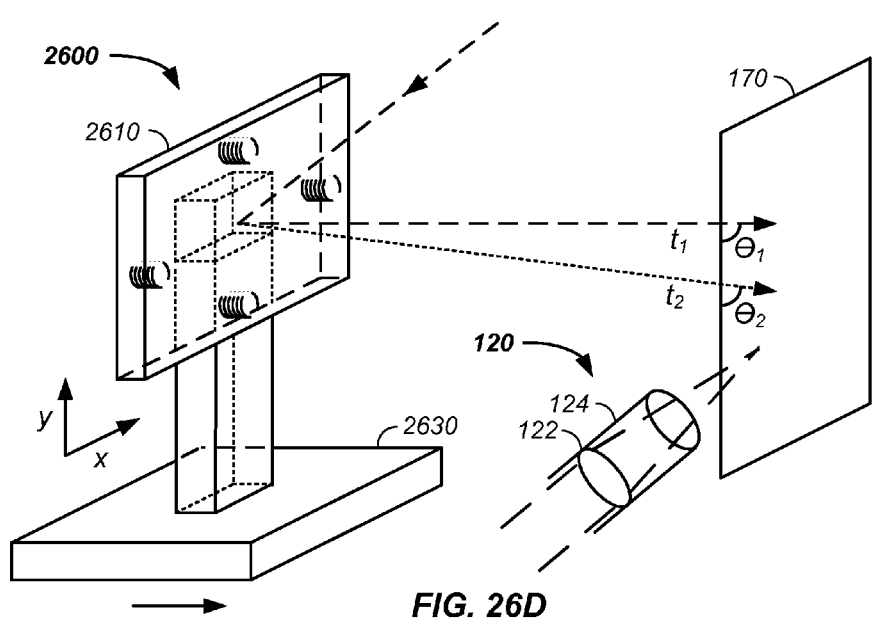
FIG. 26D illustrates radial control of incident light relative to a detection zone.

Referring now to FIG. 26D, an example is provided of the dynamically positioned optic system 2600 directing the incident light to a plurality of positions with a varying incident angle onto skin of the subject 170. As illustrated, the mirror 2610 directs light directly to the subject 170 without an optic touching the subject 170 or without touching a coupling fluid on the subject 170. However, alternatively the light is redirected after the mirror 2610, such as with a grins lens on a fiber optic element of the fiber optic bundle 2310. In this example, the incident light is directed at a first time, $t_1$, with a first incident angle, $\theta_1$, and at a second time, $t_2$, with a second incident angle, $\theta_2$. However, more generally, the dynamically positioned optic system 2600 directs the incident light to any y-, z-axis position along the x-axis of the incident light as a function of time at any solid angle, with any focusing depth, and/or an any incident angle, such as to any optic and/or to a controlled position and/or size of skin of the subject 170 relative to a detection zone. In this example, the detection zone is a volume of the subject monitored by the photon transport system 120 and/or a lens or mirror of the photon transport system 120 as interacting with the detector system 130 and a detector therein.

Adaptive Subject Measurement

Delivery of the incident light 2311 to the subject 170 is optionally varied in time in terms of position, radial position relative to a point of the skin of the subject 170, solid angle, incident angle, depth of focus, energy, and/or intensity. Herein, without limitation a spatial illumination system is used to illustrate the controlled and variable use of incident light.

Figure 27A:
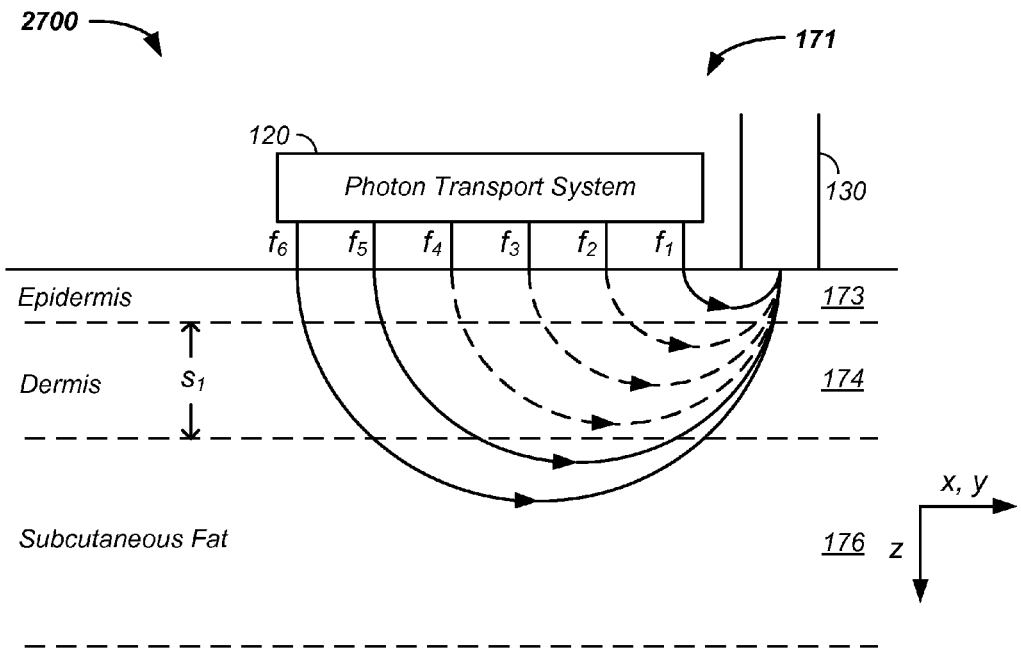
FIG. 27A and FIG. 27B illustrate a pathlength resolved sample interface for a first subject and a second subject, respectively.
Figure 27B:
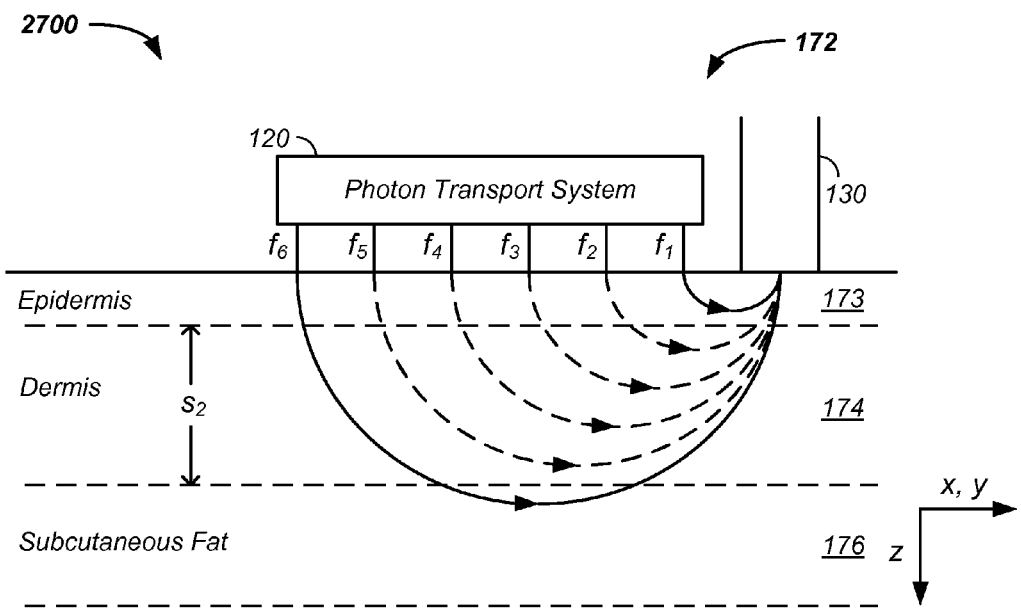

Referring now to FIG. 27A and FIG. 27B, examples of use of a spatial illumination system 2700 are illustrated for a first subject 171 and a second subject 172. However, while the examples provided in this section use a fiber optic bundle to illustrate radially controlled irradiation of the sample, the examples are also illustrative of use of the dynamically positioned optic system 2600 for directing incident light to a radially changing position about a collection zone. Still more generally the photon transport system 120 in FIGS. 27A and 27B is used in any spatially resolved system and/or in any time resolved system to deliver photons as a function of radial distance to a detector and/or to a detection zone.

Referring now to FIG. 27A and FIG. 25, an example of application of the spatial illumination system 2400 to the first subject 171 is provided. At a first point in time, the first position, $p_1$, 2421 of the filter wheel 2430 is aligned with the light input end 2312 of the fiber bundle 2310, which results in the light from the first bundlet 2411, which corresponds to the first ring 2341, irradiating the sample site 178 at a first radial distance, $r_1$, and a first depth, $d_1$, which as illustrated in FIG. 24A has a mean optical path through the epidermis. Similarly, at a second point in time, the filter wheel 2430 at the second position 2422 passes light to the second bundlet 2412, which corresponds to the second ring, irradiating the sample site 178 at a second increased distance and a second increased depth, which as illustrated in FIG. 27A has a mean optical path through the epidermis and dermis. The dynamically positioned optic system 2600 is optionally used to direct light as a function of time to the first position 2421 and subsequently to the second position 2422. Similarly, results of interrogation of the subject 170 with light passed through the six illustrative fiber illumination rings in FIG. 24A is provided in Table 3. The results of Table 3 demonstrate that for the first individual, the prime illumination rings for a blood analyte concentration determination are rings two through four as the first ring, sampling the epidermis, does not sample the blood filled dermis layer; rings two through four probe the blood filled dermis layer; and rings five and six penetrate through the dermis into the subcutaneous fat where photons are lost and the resultant signal-to-noise ratio for the blood analyte decreases.

TABLE 3

Subject 1

| Illumination Ring | Deepest Tissue Layer Probed |
|---|---|
| 1 | Epidermis |
| 2 | Dermis |
| 3 | Dermis |
| 4 | Dermis |
| 5 | Subcutaneous Fat |
| 6 | Subcutaneous Fat |

Referring now to FIG. 27B and FIG. 24A, an example of application of the spatial illumination system 2400 to the second subject 172 is provided. Again, the dynamically positioned optic system 2600 is optionally used to deliver light to the spatial illumination system 2400. Results of interrogation of the subject 170 with light passed through the six illustrative fiber illumination rings in FIG. 24A is provided in Table 4. For the second subject, it is noted that interrogation of the sample with the fifth radial fiber ring, $f_5$, results in a mean optical path through the epidermis and dermis, but not through the subcutaneous fat. In stark contrast, the mean optical path using the fifth radial fiber ring, $f_5$, for the second subject 172 has a deepest penetration depth into the dermis 174. Hence, the fifth radial fiber ring, $f_5$, yields photons probing the subcutaneous fat 176 for the first subject 171 and yields photons probing the dermis 174 of the second subject 172. Hence, for a water soluble analyte and/or a blood borne analyte, such as glucose, the analyzer 100 is more optimally configured to not use both the fifth fiber ring, $f_5$, and the sixth fiber ring, $f_6$, for the first subject 171. However, analyzer 100 is more optimally configured to not use only the sixth fiber ring, $f_6$, for the second subject 172, as described infra.

TABLE 4

Subject 2

| Illumination Ring | Deepest Tissue Layer Probed |
|---|---|
| 1 | Epidermis |
| 2 | Dermis |
| 3 | Dermis |
| 4 | Dermis |
| 5 | Dermis |
| 6 | Subcutaneous Fat |

In yet another example, light is delivered with known radial distance to the detection zone, such as with optics of the analyzer, without use of a fiber optic bundle and/or without the use of a filter wheel. Just as the illumination ring determines the deepest tissue layer probed, control of the irradiation zone/detection zone distance determines the deepest tissue layer probed.

Incident Light Control

Referring again to FIGS. 26A-D, the dynamically positioned optic system 2600 is optionally used as a function of time to control one or more of:

delivery of the incident light 2311 to a single selected fiber optic of the fiber optic bundle 2310;

delivery of the incident light 2311 to a selected bundlet of the set of fiber optic bundlets 2410, such as to the first bundlet 2411 at a first point in time and to the second bundlet 2412 at a second point in time;

variation of solid angle of the incident light 2311 to an optic and/or to the subject 170;

variation of radial position of delivery of the incident light 2311 relative to a fixed location, such as a center of an optic, a target point on skin of the subject 170, or a center of the sample site 178;

incident angle of the incident light 2311 relative to a plane tangential to the skin of the subject 170 and/or an axis normal to the skin of the subject 170 at the sample site 178;

apparent focus depth of the incident light 2311 into the skin of the subject 170;

energy; and intensity, such as number of photon per second varying from one point in time to another by greater than 1, 10, 50, 100, 500, 1000, or 5000 percent.

Time Resolved Spectroscopy

In still yet another example, referring again to time resolved spectroscopy, instead of delivering light through the filter wheel to force radial distance, photons are optionally delivered to the skin and the time resolved gating system is used to determine probably photon penetration depth. For example, Table 5 shows that at greater elapsed time to the $n^{th}$ gated detection period, the probability of the deepest penetration depth reaching deeper tissue layers increases.

TABLE 5

| Time Resolved Spectroscopy | |
| --- | --- |
| Elapsed Time (picoseconds) | Deepest Tissue Layer Probed |
| 1 | Epidermis |
| 10 | Dermis |
| 50 | Dermis |
| 100 | Subcutaneous Fat |

Data Processing

Figure 28:
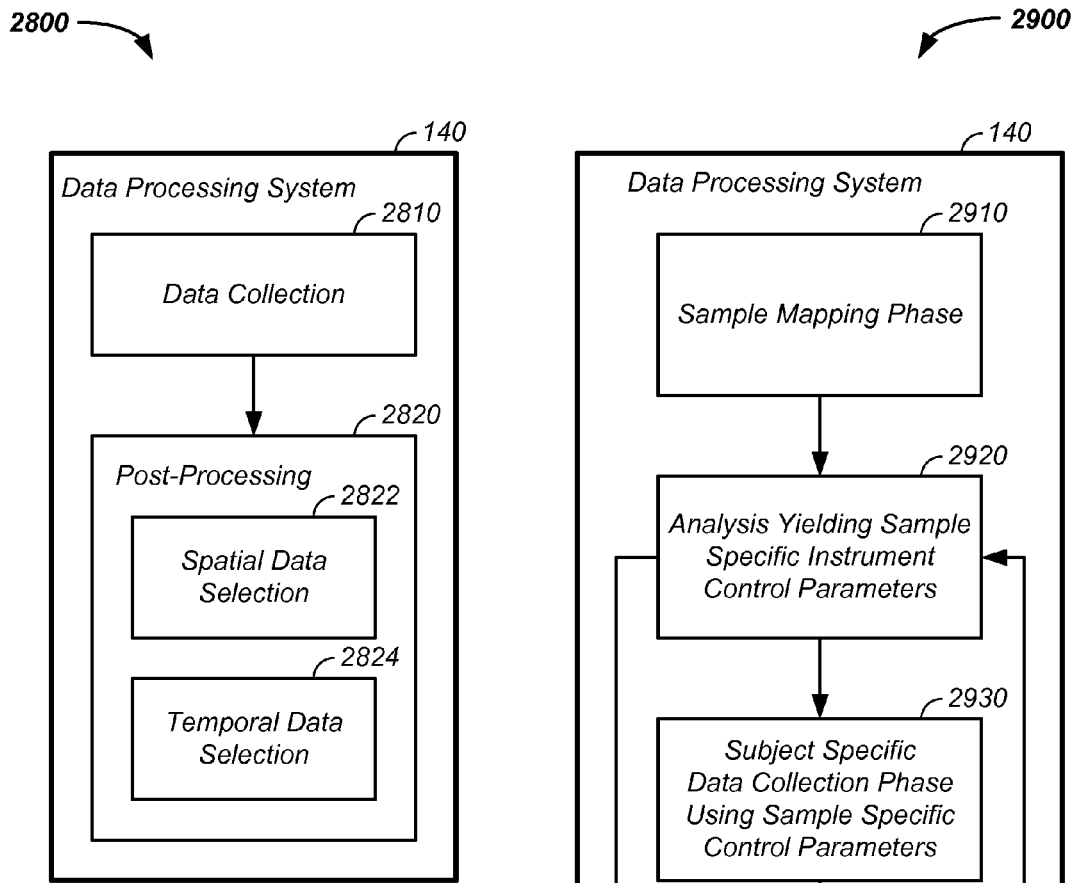
FIG. 28 provides a method of use of a data processing system.

Referring now to FIG. 28, the data processing system 140 is further described. The data processing system 140 optionally uses a step of post-processing 2820 to process a set of collected data 2810. The post-processing step 2420 optionally operates on data collected as a function of any of: radial distance of the incident light 2311 to a reference point, such as a detector; solid angle of the incident light 2311 relative to the subject 170; angle of the incident light 2311 relative to skin of the subject 170; and/or depth of focus of the incident light 2311 relative to a surface of the skin of the subject 170.

Two-Phase Measurement(s)

Figure 29:
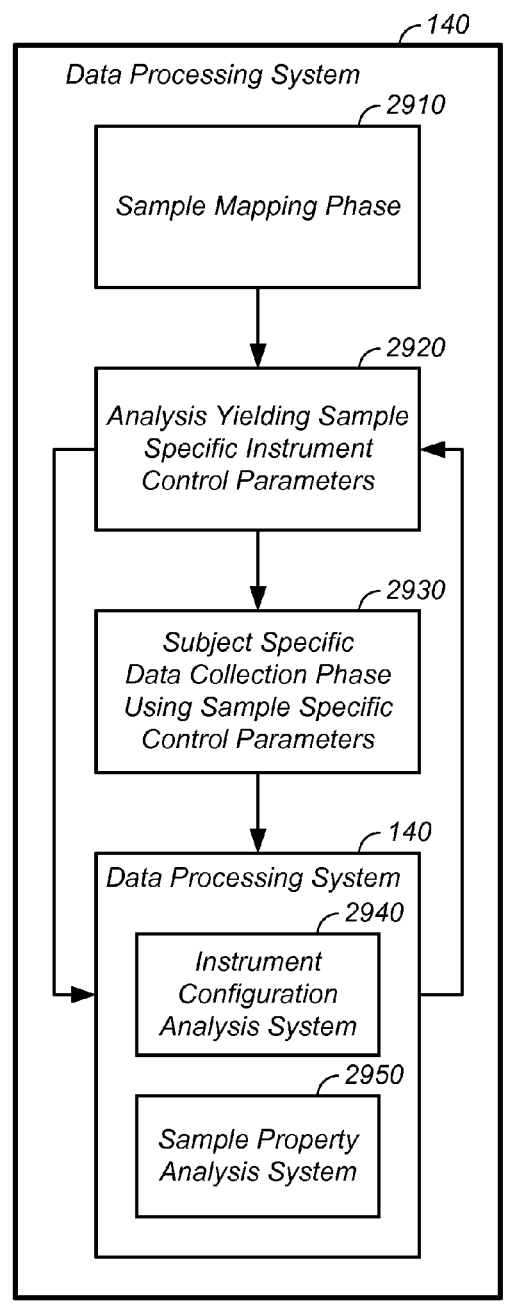
FIG. 29 provides a method of using a sample mapping phase and a subsequent subject specific data collection phase.

Referring now to FIG. 29, in another embodiment, the analyzer 100 is used in two phase system 2900: (1) a sample mapping phase 2910, such as a subject or group mapping phase and (2) a subject specific data collection phase 2930/data analysis phase. In one example, in the first mapping phase 2910, skin of the subject 170 is analyzed with the analyzer 100 using a first optical configuration. Subsequently, the mapping phase spectra are analyzed 2920. In the second subject specific data collection phase 2930, the analyzer 100 is setup in a second optical configuration based upon data collected in the sample mapping phase 2910. The second optical configuration is preferably configured to enhance performance of the analyzer 100 in terms of accuracy and/or precision of estimation and/or determination of an analyte property, such as a noninvasive glucose concentration. Examples provided, infra, use a single subject 170. However, more generally the sample mapping phase 2910 is optionally used to classify the subject into a group or cluster and the analyzer 100 is subsequently setup in a second optical configuration for the group or cluster, which represents a subset of the human population, such as by gender, age, skin thickness, water absorbance, fat absorbance, protein absorbance, epidermal thickness, dermal thickness, depth of a subcutaneous fat layer, and/or a model fit parameter. For clarity of presentation, several examples are provided, infra, describing use of a sample mapping phase 2910 and a subsequent subject specific data collection phase 2930.

In a first example, referring again to FIG. 27A and FIG. 27B, a first optional two-phase measurement approach is herein described. Optionally, during the first sample mapping phase 2910, the photon transport system 120 provides interrogation photons to a particular test subject at controlled, but varying, radial distances from the detection system 130. One or more spectral markers, or an algorithmic/mathematical representation thereof, are used to determine the radial illumination distances best used for the particular test subject. An output of the first phase is the data processing system 140 selecting how to illuminate/irradiate the subject 170. Subsequently, during the second subject specific data collection phase 130, the system controller 180 controls the photon transport system 120 to deliver photons over selected conditions and/or optical configuration to the subject 170.

In a second example, a first spectral marker is optionally related to the absorbance of the subcutaneous fat 176 for the first subject 171. During the first sample mapping phase 2710, the fifth and sixth radial positions of the fiber probe illustrated in FIG. 24A, yield collected signals for the first subject 171 that contain larger than average fat absorbance features, which indicates that the fifth and sixth fiber rings of the example fiber bundle should not be used in the subsequent second data collection phase, which more generally establishes an outer radial distance for subsequent illumination. Still in the first sample mapping phase 130, probing the tissue of the subject with photons from the fourth fiber ring yields a reduced signal for the first spectral marker and/or a larger relative signal for a second spectral marker related to the dermis 174, such as a protein absorbance band or an algorithmic/mathematical representation thereof. Hence, the data processing system 140 yields a result that the fifth and sixth radial fiber optic rings or distance of the fiber bundle 170 should not be used in the second subject specific data collection phase 2930 and that the fourth radial fiber optic ring or distance should be used in the second subject specific data collection phase 2930. Subsequently, in the second subject specific data collection phase 2930, data collection for analyte determination ensues using the first through fourth radial positions of the fiber bundle, which yields a larger signal-to-noise ratio for dermis constituents, such as glucose, compared to the use of all six radial positions of the fiber bundle. Optionally, data already collected in the mapping phase is subsequently re-used in the data analysis phase.

In a third example, the first sample mapping phase 2910 of the previous example is repeated for the second subject 172. The first sample mapping phase 2910 indicates that for the second subject, the sixth radial illumination ring of the fiber bundle illustrated in FIG. 24A should not be used, but that the fourth and fifth radial illumination ring should be used.

In a fourth example, the first mapping phase 2910 determines positions on the skin where papillary dermis ridges are closest to the skin surface and positions on the skin where the papillary dermis valleys are furthest from the skin surface. In the subsequent subject specific data collection phase 2930, the incident light is optionally targeted at the papillary dermis valleys, such as greater than 50, 60, or 70 percent of the incident light is targeted at the papillary dermis valley and less than 30, 40, or 50 percent of the incident light is targeted at the papillary dermis ridge. The increased percentage of the incident light striking the papillary dermis valley increases the number of photons sampling the underlying dermis layer, where blood borne analytes reside, which increases the signal-to-noise ratio of collected data and lowers resultant errors in blood borne analyte property determination.

Generally, a particular subject is optionally probed in a sample mapping phase 2910 and results from the sample mapping phase 2910 are optionally used to configure analyzer parameters in a subsequent subject specific data collection phase 2930. While for clarity of presentation, and without loss of generality, radial distance was varied in the provided examples, any optical parameter of the analyzer is optionally varied in the sample mapping phase 2910, such as sample probe position, incident light solid angle, incident light angle, focal length of an optic, position of an optic, energy of incident light, and/or intensity of incident light. Optionally, the sample mapping phase 2910 and sample specific data collection phase 2930 occur within less than 1, 5, 10, 20, or 30 seconds of each other. Optionally, the subject 170 does not move away from the sample interface 150 between the sample mapping phase 2910 and the subject specific data collection phase 130. Further, generally each of the spatial and temporal methods yield information on pathlength, b, and/or a product of the molar absorptivity and pathlength, which is not achieved using a standard spectrometer.

In yet another embodiment, the sample interface tip 2316 of the fiber optic bundle 2310 includes optics that change the mean incident light angle of individual fibers of the fiber optic bundle 2316 as they first hit the subject 170. For example, a first optic at the end of a fiber in the first ring 1041 aims light away from the collection fiber optic 2318; a second optic at the end of a fiber in the second ring 2342 aims light nominally straight into the sample; and a third optic at the end of a fiber in the third ring 2342 aims light toward the collection fiber 2318. Generally, the mean direction of the incident light varies by greater than 5, 10, 15, 20, or 25 degrees.

In still another embodiment, the two-dimensional detector array is used in the mapping phase to determine positions of best signal and/or positions of interference, such as a hair follicle. In the data analysis phase, the determined sub-optimal regions, such as those related to the detected hair follicle, are not used in the analyte determination phase.

Data Processing System

The data processing system 140 is further described herein. Generally, the data processing system uses an instrument configuration analysis system 2940 to determine an optical configuration of the analyzer 100 and/or a software configuration of the analyzer 100 while the sample property analysis system 2950 is used to determine a chemical, a physical, and/or a medical property, such as an analyte concentration, measured or represented by collected spectra. Further, the data processing system 140 optionally uses a preprocessing step and a processing step to determine an instrument configuration and/or to determine an analyte property.

In one embodiment, the data processing system 140 uses a preprocessing step to achieve any of: lower noise and/or higher signal. Representative and non-limiting forms of preprocessing include any of: use of a digital filter, use of a convolution function, use of a derivative, use of a smoothing function, use of a resampling algorithm, and/or a form of assigning one or more spectra to a cluster of a whole. The data processing system subsequently uses any multivariate technique, such as a form of principal components regression, a form of partial least squares, and/or a form of a neural network to further process the pre-processed data.

In another embodiment, the data processing system 140 and/or the sample property analysis system 2950 operates on spectra collected by the analyzer 100, such as in the subject specific data collection phase 2930, using a first step of defining finite width channels and a second step of feature extraction, which are each further described, infra.

Finite Width Channels

In one example, the sample property analysis system 2950 defines a plurality of finite width channels, where the channels relate to changes in an optical parameter, software setting of the analyzer 100, a chemical condition, a physical property, a distance, and/or time. Still further, the channels optionally relate to radial distance between the incident light from the analyzer 100 entering skin of the subject 170 and detected light exiting the skin of the subject 170 and detected by the detector system 130, a focal length of an optic, a solid-angle of a photon beam from the source system 110, an incident angle of light onto skin of the subject, and/or a software setting, such as control over spectral resolution. For clarity of presentation, the channels are described herein in terms of wavelength channels. For example, a spectrum is collected over a range of wavelengths and the finite width channels represent finite width wavelength channels within the spectrum. Generally, the channels are processed to enhance localized signal, to decrease localized noise, and/or are processed using a cross-wavelet transform.

In one case, the sample property analysis system 2950 defines a plurality of finite width wavelength channels, such as more than 3, 5, 10, 15, 20, 30, 40, or 50 wavelength channels contained in a broader spectral region, such as within a spectrum from 900 to 2500 nanometers or within a sub-range therein, such as within 1100 to 1800 nanometers. The plurality of multiple finite width wavelength channels enhance accessibility to content related to: (1) a target analyte, such as a glucose concentration, and (2) a measurement context, such as the state of skin of the subject 170, which is used as information in a self-correcting background.

Feature Extraction

In one case, feature extraction determines and/or calculates coherence between channels, which is referred to herein as cross-coherence, to identify and/or enhance information common to the analytical signal, such as frequency, wavelength, shift, and/or phase information. Subsequently, cross-coherence terms are selected using a metric, such as to provide maximum contrast between: (1) the target analyte or signal and (2) the measurement context or background. Examples of background include, but are not limited to: spectral interference, instrument drift impacting the acquired signal, spectral variation resultant from physiology and/or tissue variation, temperature impact on the analyzer, mechanical variations in the analyzer as a function of time, and the like. Generally, the cross-coherence terms function to reduce toward or to monotonicity detected variation as a function of analyte concentration. In a particular instance, an N×N grid is generated per spectrum, which is symmetric about the diagonal of the N×N grid, with each grid element representing an M term coherence estimate versus frequency, where N is a positive integer of at least three.

Model

Typically, a model, such as a nonlinear model, is constructed to map the extracted features to the analyte property, such as a glucose concentration. For example, the total differential power of the cross-coherence estimate is determined between features related to the analyte versus the background and a separate nonlinear function is calculated for multiple analyte ranges.

Absorbance Spectra

The data processing system 140 optionally uses absorbance spectra of skin and/or blood constituents, such as water absorbance peaks at about 1450 nm or in the range of 1350 to 1500 nm.

Personal Communication Device

Herein, a personal communication device comprises any of a wireless phone, a cell phone, a smart phone, a tablet, a phablet, a wearable internet connectable accessory, a wearable internet connectable garment, and/or a smart wearable accessory, such as a watch with internet and/or phone communication ability. Optionally, the analyzer 100 has no display screen and results are transmitted to a personal communication device of the user, which allows a smaller analyzer 100 and/or the analyzer to be semi-continuously worn in a non-conspicuous location, such as under a shirt or around the torso of the individual.

Optionally, the personal communication device and/or the analyzer communicate with a data processing center. For example, the data processing center received data from the analyzer 100 through use of at least one wireless step, processes the data, and sends a result and/or a model parameter to the personal communication device of the user, resulting in one or more of: a displayed analyte concentration, a description of detection of an analyzer error, and/or an alert, such as a rapidly falling glucose concentration, an abnormally high glucose concentration, and/or a request for use of an alternative glucose determination method.

Still yet another embodiment includes any combination and/or permutation of any of the analyzer and/or sensor elements described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Herein, a set of fixed numbers, such as 1, 2, 3, 4, 5, 10, or 20 optionally means at least any number in the set of fixed number and/or less than any number in the set of fixed numbers.

Herein, specific wavelengths are used to facilitate communication of key spectroscopic points. However, the specific wavelengths presented are optionally plus and/or minus 10, 20, 30, 40, 50, 75, or 100 nm.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for noninvasive analyte property estimation of a constituent of a human subject, comprising:
    a near-infrared analyzer, comprising:
        a near-infrared source;
        a detector array;
        a photon transport system configured to transport photons along an optical train from said near-infrared source to said detector array via an analyzer-subject interface;
        a first planar two-dimensional filter array comprising a first set of optical filters, said first set of optical filters comprising at least two optical filters; and
        a second planar two-dimensional filter array comprising a second set of optical filters,
        said optical train sequentially passing through said first planar two-dimensional filter array and said second planar two-dimensional filter array,
        said first planar two-dimensional filter array substantially parallel to said second planar two-dimensional filter array.

2. The apparatus of claim 1, said first set of optical filters further comprising:
    a first optical filter optically linked to a first set of at least three detector elements of said detector array; and
    a second optical filter optically linked to a second set of at least three detector elements of said detector array,
    a first portion of said first optical filter overlapping said second optical filter, and
    a second portion of said first optical filter not-overlapping said second optical filter.

3. The apparatus of claim 2, said first set of optical filters and said second set of optical filters further comprising:
    a first optical connection to a common detector element of said detector array.

4. The apparatus of claim 1, said detector array comprising a larger surface area detector element positioned further from a center of said analyzer-subject interface than a smaller surface area detector element.

5. The apparatus of claim 1, said first set of optical filters further comprising at least one longpass filter substantially blocking visible light.

6. The apparatus of claim 5, said second set of optical filters further comprising at least one shortpass filter overlapping said at least one longpass filter.

7. The apparatus of claim 6, said first set of optical filters further comprising:
    a square filter; and
    a non-square, rectangular filter.

8. The apparatus of claim 1, further comprising:
    a two-dimensional focusing optic array in said optical train.

9. The apparatus of claim 8, said two-dimensional focusing optic array further comprising:
    a first optic comprising a mean optical path tilted away from a photon illumination zone of said analyzer-subject interface.

10. The apparatus of claim 8, said two-dimensional focusing optic array further comprising:

a second optic comprising a mean optical path tilted toward a vector passing perpendicular to the subject through said analyzer-subject interface.

11. The apparatus of claim 1, said first set of optical filters further comprising:
a first filter comprising a first fifty percent transmission cut-on wavelength;
a second filter comprising a second fifty percent transmission cut-on wavelength at least one hundred nanometers less than said first fifty percent transmission cut-on wavelength; and
a third filter comprising a third fifty percent transmission cut-on wavelength at least one hundred nanometers less than said second fifty percent transmission cut-on wavelength.

12. A method for noninvasive analyte property estimation of a constituent of a human subject, comprising the steps of:
providing a near-infrared analyzer, comprising:
a near-infrared source;
a detector array;
a first planar two-dimensional filter array comprising a first set of optical filters, said first set of optical filters comprising at least two optical filters;
a second planar two-dimensional filter array comprising a second set of optical filters; and
a photon transport system; and
transporting photons along an along an optical train from said near-infrared source to said detector array via an analyzer-subject interface using said photon transport system, said optical train sequentially passing through said first planar two-dimensional filter array and said second planar two-dimensional filter array,
said first planar two-dimensional filter array substantially parallel to said second planar two-dimensional filter array.

13. The method of claim 12, further comprising:
a first filter of said first two-dimensional filter array, said first filter comprising an edge; and
a second filter of said second two-dimensional filter array, said second filter comprising a non-edge, surface filter area,
wherein said edge of said first filter optically overlaps said non-edge, surface filter area of said second filter.

14. The method of claim 12, further comprising the step of:
transmitting the photons through both a first combination of filter elements and a second combination of filter elements, said second combination of filter elements passing a second mean wavelength at least one hundred nanometers longer than a first mean wavelength passed by said first combination of filter elements; and
positioning said second combination of filter elements closer to a center of said analyzer-subject interface compared to a position of said first combination of filter elements.

15. The method of claim 12, further comprising the step of:
using said detector array to detect light passing through at least twenty distinct combinations of filters of said first two-dimensional filter array and said second two-dimensional filter array.

* * * * *